US008975404B2

(12) United States Patent
Pillai et al.

(10) Patent No.: US 8,975,404 B2
(45) Date of Patent: Mar. 10, 2015

(54) LABELING REAGENTS FOR ANALYTE DETERMINATION AND METHODS AND COMPOUNDS USED IN MAKING THE SAME

(75) Inventors: Sasi K. Pillai, Littleton, MA (US); Subhakar Dey, North Billerica, MA (US); Subhasish Purkayastha, Acton, MA (US); Darryl J. C. Pappin, Boxborough, MA (US)

(73) Assignee: DH Technologies Development Pte. Ltd., Singapore (SG)

( * ) Notice: Subject to any disclaimer, the term of this patent is extended or adjusted under 35 U.S.C. 154(b) by 1264 days.

(21) Appl. No.: 11/625,688

(22) Filed: Jan. 22, 2007

(65) Prior Publication Data

US 2007/0218560 A1     Sep. 20, 2007

Related U.S. Application Data

(60) Provisional application No. 60/764,216, filed on Feb. 1, 2006, provisional application No. 60/761,711, filed on Jan. 24, 2006.

(51) Int. Cl.
| | |
|---|---|
| *C07D 295/15* | (2006.01) |
| *C07D 403/12* | (2006.01) |
| *G01N 33/58* | (2006.01) |
| *G01N 33/68* | (2006.01) |

(52) U.S. Cl.
CPC ............ *C07D 295/15* (2013.01); *C07D 403/12* (2013.01); *G01N 33/58* (2013.01); *G01N 33/6848* (2013.01)
USPC ........................................................ 544/357

(58) Field of Classification Search
None
See application file for complete search history.

(56) References Cited

U.S. PATENT DOCUMENTS

| | | | |
|---|---|---|---|
| 5,705,610 A | 1/1998 | Zuckermann et al. | |
| 5,800,992 A | 9/1998 | Foder et al. | |
| 6,027,890 A | 2/2000 | Van Ness et al. | |
| 6,270,976 B1 | 8/2001 | Schmidt et al. | |
| 6,287,780 B1 | 9/2001 | Schmidt et al. | |
| 6,475,807 B1 | 11/2002 | Geysen et al. | |
| 7,056,942 B2 * | 6/2006 | Hildesheim et al. | 514/411 |
| 2005/0049406 A1 | 3/2005 | Lerchen et al. | |
| 2005/0148774 A1 | 7/2005 | Dey et al. | |

FOREIGN PATENT DOCUMENTS

| | | | | |
|---|---|---|---|---|
| WO | WO 98/31830 A | | 7/1998 | |
| WO | WO 9902163 | * | 1/1999 | ........... A61K 31/535 |
| WO | WO 2004/019000 A | | 3/2004 | |
| WO | WO 2004/070352 A | | 8/2004 | |
| WO | WO2005054871 | | 6/2005 | |
| WO | WO 2005/068446 A | | 7/2005 | |
| WO | WO2005085869 | | 9/2010 | |

OTHER PUBLICATIONS

Hennard et al. Journal of Medicinal Cheimistry, 2001, 44(13), pp. 2139-2151.*
Stenlake. European Journal of Medicinal Chemistry, 1992, 27(5), 463-77.*
Schleogl et al., Pharmacodynamically Active, 3,4,5-Trimethoxybenzoates and Related Esters of Symmetrical Bis (Hydroxyalkyl) Piperazines and Dialkypolymethylenediamines. Monatshefte Fuer Chemie, 1964, vol. 95(3), pp. 922-941, especially p. 924.
Bottari P et al: "Design and Synthesis of Visible Isotope-Coded Affinity Tags for the Absolute Quantification of Specific proteins in Complex Mixtures" Bioconjugate Chemistry, ACS, Washington, D.C., U.S. vol. 15, No. 2, Feb. 21, 2004, pp. 380-388.
Dunayevskiy, Yuriy M.: "Application of Capillary Electrophoresis-Electrospray ionization Mass Spectrometry in the Determination of Molecular Diversity"; PNAS 1996, Proc. Natl. Acad. Sci. USA 93—Boston, MA, Jan. 30, 1996, pp. 6152-6157.
Gygi S P et al: "Quantitative Analysis of Complex Protein Mixtures using Isotope-Coded Affinity Tags" Nature Biotechnology, nature Publishing Group, New York, NY, U.S. vol. 17, No. 10, Oct. 1, 1999, pp. 994-999.
Office Action for Japan Patent Application 2008-552544 (and translation) Oct. 2, 2012.

* cited by examiner

*Primary Examiner* — Noble Jarrell

(57) ABSTRACT

Provided herein are labeling reagents for analyte determination in a sample, and methods of manufacturing the labeling reagents. By way of non-limiting example, analytes may include one or more of peptides, proteins, nucleic acid molecules, carbohydrates, lipids, steroids and/or small molecules. Also provided are labeled analytes themselves after one or more labeling reagents binds to an analyte. Analytes may be labeled for determination of the analyte by mass analysis, such as by mass spectrometry. Further provided are compounds that may be used in making the labeling reagents and labeled analytes, such as reporter group compounds. Also provided are kits that include at least one labeling reagent, and may further include or more other reagents, containers, enzymes, buffers, a labeled analyte (e.g., as a standard) and/or instructions. Further examples are also possible.

14 Claims, 51 Drawing Sheets

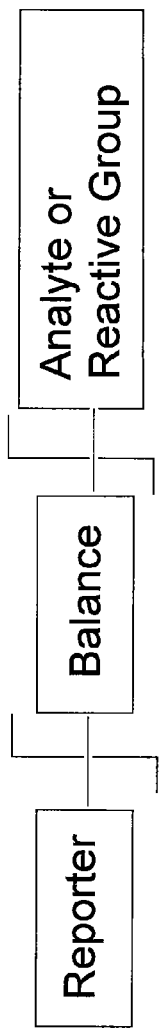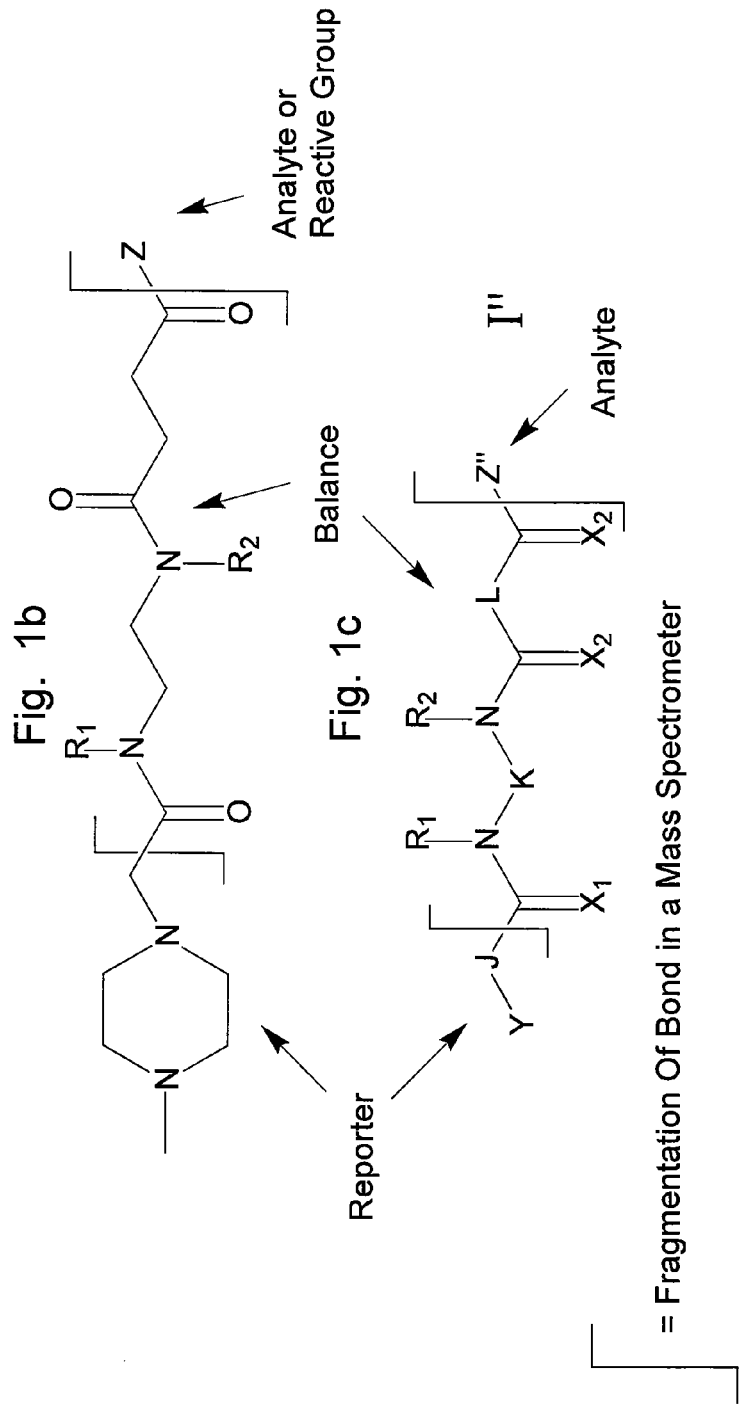

General Formulas of Some Isobaric Labeling Reagents

Each * indicates where a $^{13}C$ is substituted of $^{12}C$ or $^{15}N$ is subsituted for $^{14}N$, as appropriate Fig. 2b
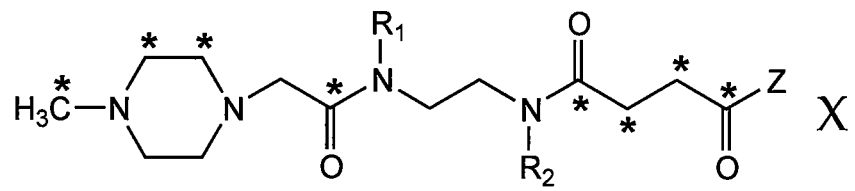
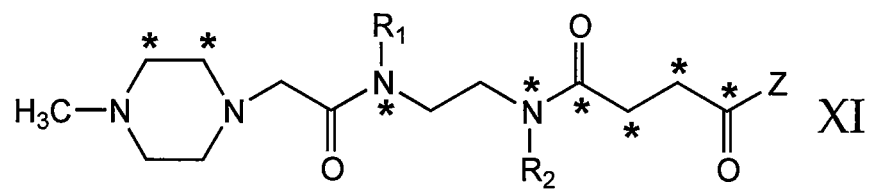
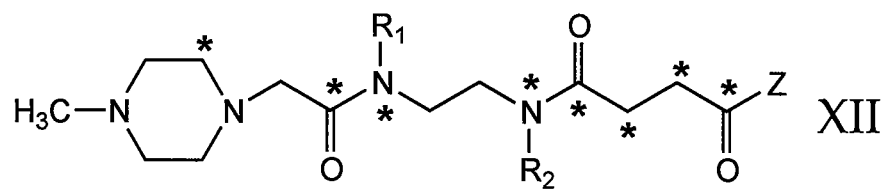
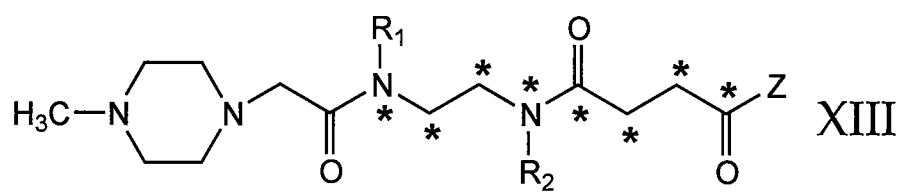
Each * indicates where a $^{13}C$ is substituted of $^{12}C$
or $^{15}N$ is subsituted for $^{14}N$, as appropriate Fig. 3a
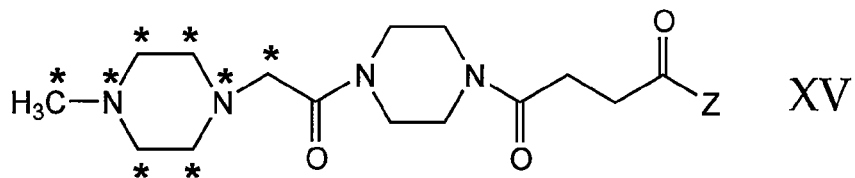 XV
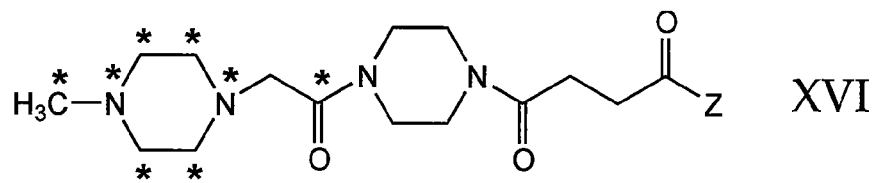 XVI
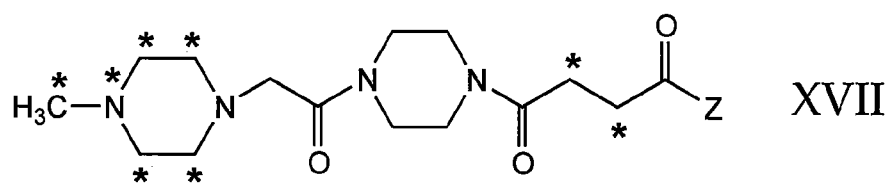 XVII
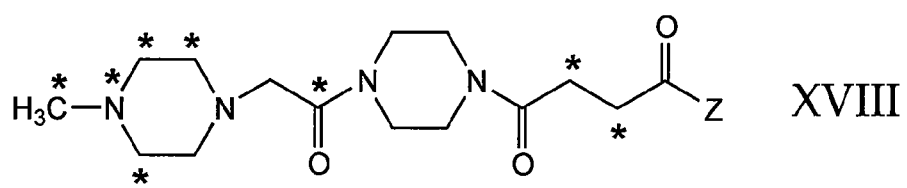 XVIII
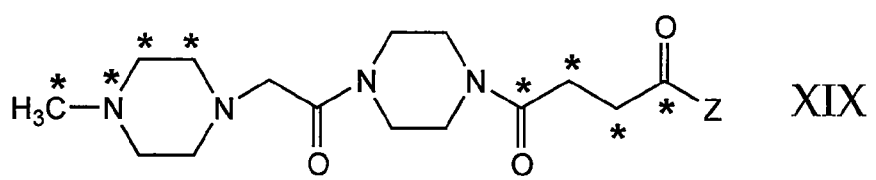 XIX
Each * indicates where a $^{13}$C is substituted of $^{12}$C
or $^{15}$N is subsituted for $^{14}$N, as appropriate Each * indicates where a $^{13}C$ is substituted of $^{12}C$
or $^{15}N$ is subsituted for $^{14}N$, as appropriate

Fig. 4a
Exemplary Isobars
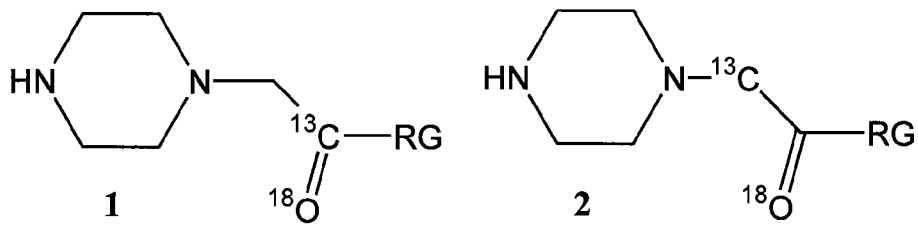
Mass Of Compounds 1 and 2 = 130.095
Mass Of Compounds 3 and 4 = 130.085
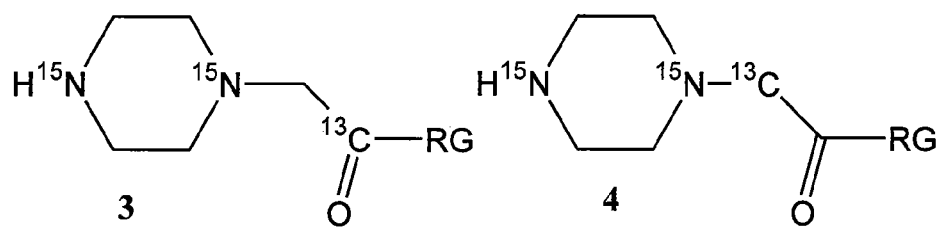
Fig. 4b
Exemplary Isomeric Isobars
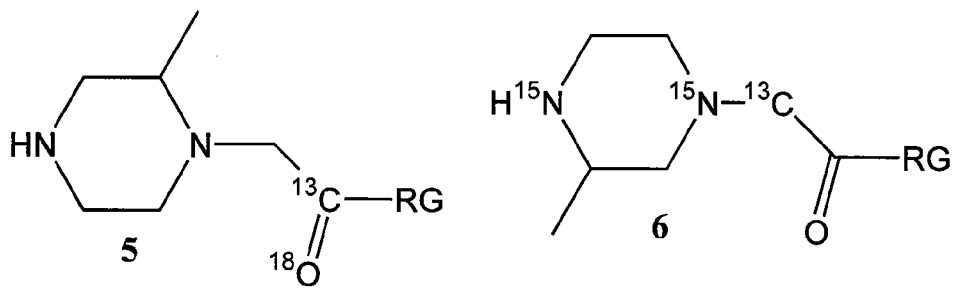
Mass of Compound 5 = 144.111
Mass of Compound 6 = 144.100
Notes: RG = Reactive Group
The Mass Stated Is Only For The
Reporter/Linker Combination

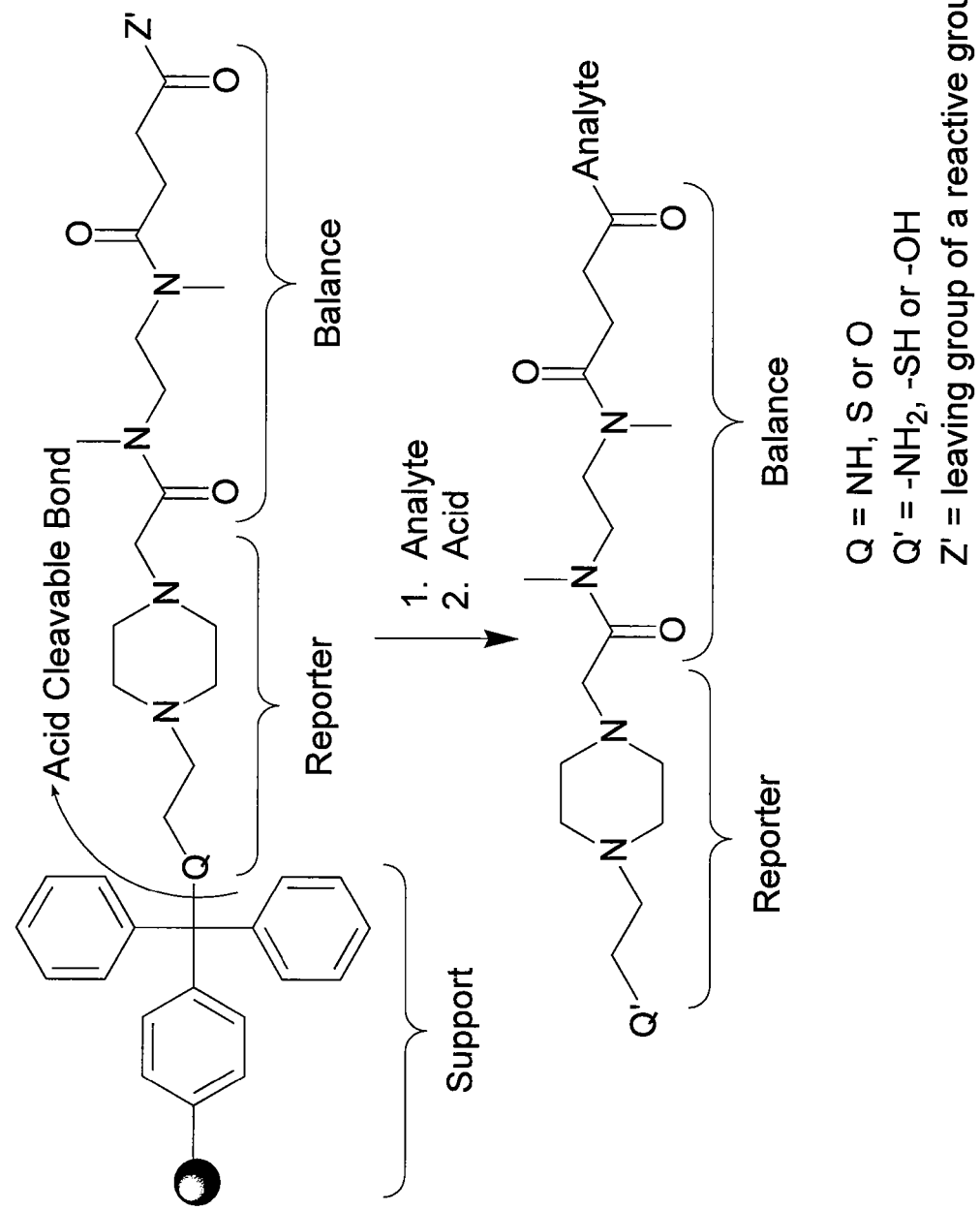

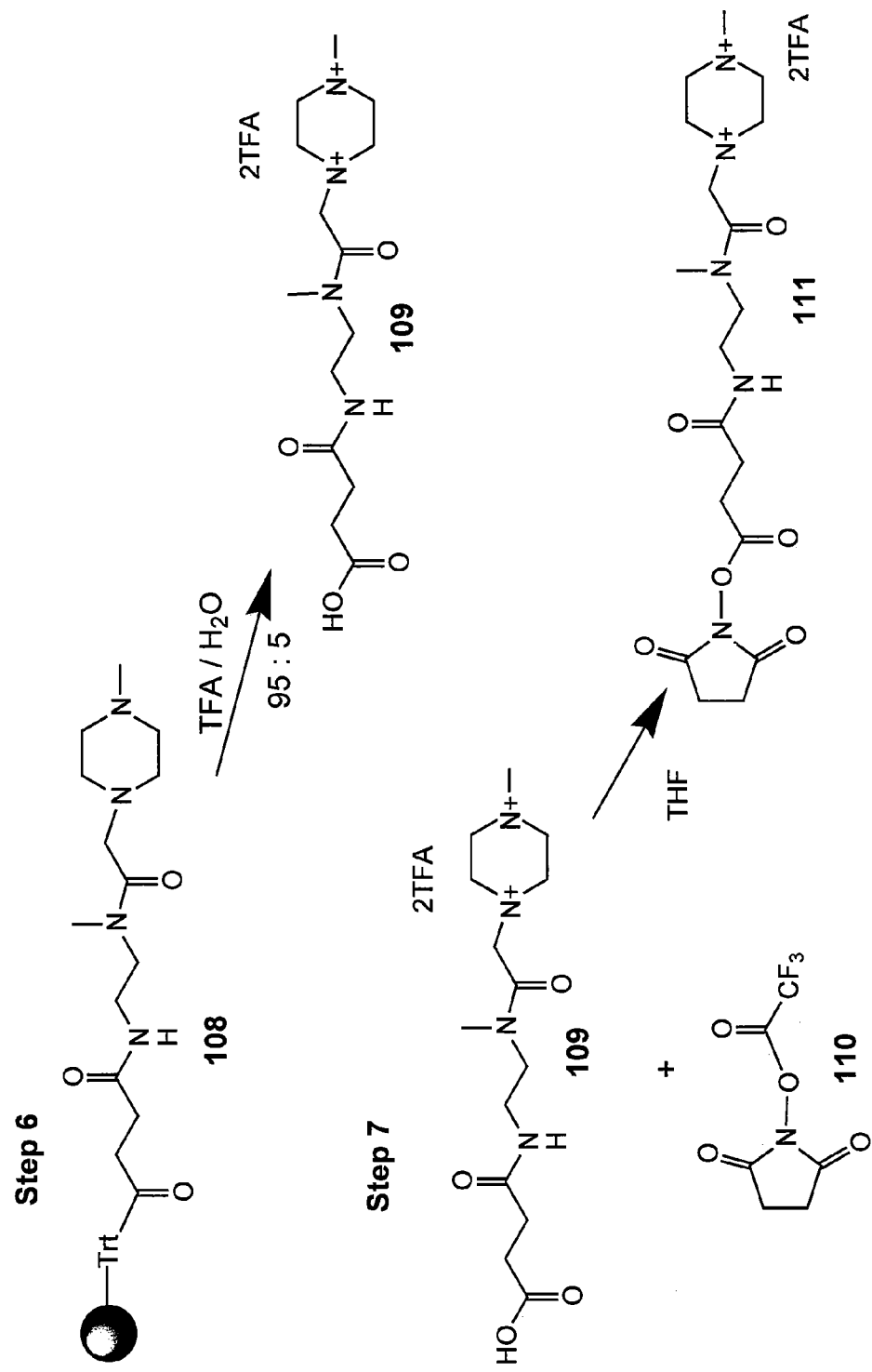

Scheme For The Synthesis Of Various Active Esters

Fig. 9a

Possible Source Materials For Compounds V - XIII

| Cpd | Piperazine Acetic Acid | Diamine | Anhydride |
|---|---|---|---|
| V | H$_3$$^{13}$C-$^{15}$N($^{13}$C-$^{13}$C)($^{13}$C-$^{13}$C)N-$^{15}$N-$^{13}$C-COOH<br>See Note Below | R$_1$-HN-CH$_2$CH$_2$-NH-R$_2$ with Fmoc | succinic anhydride |
| VI | H$_3$$^{13}$C-$^{15}$N($^{13}$C-$^{13}$C)($^{13}$C-$^{13}$C)N-CH$_2$-$^{13}$C-COOH<br>See Note Below | R$_1$-HN-CH$_2$CH$_2$-NH-R$_2$ with Fmoc | succinic anhydride |
| VII | H$_3$$^{13}$C-$^{15}$N($^{13}$C-$^{13}$C)($^{13}$C-$^{13}$C)N-CH$_2$-COOH<br>See Note Below | R$_1$-HN-CH$_2$CH$_2$-NH-R$_2$ with Fmoc | $^{13}$C-$^{13}$C labeled anhydride<br>P/N = 603902 Isotec, Inc. |

Note: See US Pat. Publ. Nos. US 2004-0219685 A1, US 2004-0147982 A1 and US 2005-1048774 A1

Fig. 9b

Possible Source Materials For Compounds V - XIII

| Cpd | N-Methyl Piperazine Acetic Acid | Diamine | Anhydride |
|---|---|---|---|
| VIII | [structure with $^{13}C$-$^{13}C$, $^{15}N$, $^{13}C$ labels] See Note Below | [Fmoc-N(R$_1$)-CH$_2$CH$_2$-NH-R$_2$] | [structure] P/N = 603902 Isotec, Inc. |
| IX | [structure with $^{13}C$-$^{13}C$, $^{15}N$ labels] See Note Below | [Fmoc-N(R$_1$)-CH$_2$CH$_2$-NH-R$_2$] | [structure] P/N = 578517 Isotec, Inc. |
| X | [structure with $^{13}C$-$^{13}C$ labels] See Note Below | [Fmoc-N(R$_1$)-CH$_2$CH$_2$-NH-R$_2$] | [structure] P/N = 578517 Isotec, Inc. |

Note: See US Pat. Publ. Nos. US 2004-0219685 A1, US 2004-0147982 A1 and US 2005-1048774 A1

Fig. 10a
Possible Source Materials For Compounds XV-XXXIII

| Cpd | Piperazine Acetic Acid | Diamine | Anhydride |
|---|---|---|---|
| XV | (structure with $^{13}C$, $^{15}N$ labels)<br>See Note Below | piperazine (NH/HN) | succinic anhydride |
| XVI | (structure with $^{13}C$, $^{15}N$ labels)<br>See Note Below | piperazine (NH/HN) | succinic anhydride |
| XVII | (structure with $^{13}C$ labels)<br>See Note Below | piperazine (NH/HN) | $^{13}C$-labeled anhydride<br>P/N = 603902<br>Isotec, Inc. |

Note: See US Pat. Publ. Nos. US 2004-0219685 A1, US 2004-0147982 A1 and US 2005-1048774 A1

Fig. 10b
Possible Source Materials For Compounds XV-XXIII

| Cpd | Piperazine Acetic Acid | Diamine | Anhydride |
|---|---|---|---|
| XVIII | See Note Below | | P/N = 603902 Isotec, Inc. |
| XIX | See Note Below | | P/N = 578517 Isotec, Inc. |
| XX | See Note Below | | P/N = 578517 Isotec, Inc. |

Note: See US Pat. Publ. Nos. US 2004-0219685 A1, US 2004-0147982 A1 and US 2005-1048774 A1

Fig. 10c
Possible Source Materials For Compounds XV-XXIII

| Cpd | N-Methyl Piperazine Acetic Acid | Diamine | Anhydride |
|---|---|---|---|
| XXI | $^{13}C-^{13}C$ structure with $H_3C$ group<br>See Note Below | Diamine with $^{13}C-^{13}C$ label, 46<br>See Note Below | $^{13}C$-labeled anhydride<br>P/N = 578517, Isotec, Inc. |
| XXII | $^{13}C$ structure with $H_3C$ group<br>See Note Below | Diamine with $^{13}C-^{13}C$ label, 46<br>See Note Below | $^{13}C$-labeled anhydride<br>P/N = 578517, Isotec, Inc. |
| XXIII | Structure with $H_3C$ group<br>See Note Below | Diamine with $^{13}C-^{13}C$ label, 44<br>See Note Below | $^{13}C$-labeled anhydride<br>P/N = 578517, Isotec, Inc. |

Note: See US Pat. Publ. Nos. US 2004-0219685 A1, US 2004-0147982 A1 and US 2005-1048774 A1

Synthetic Route to Encoded Sarcosine Comprising Four Isotopically Encoded Sites

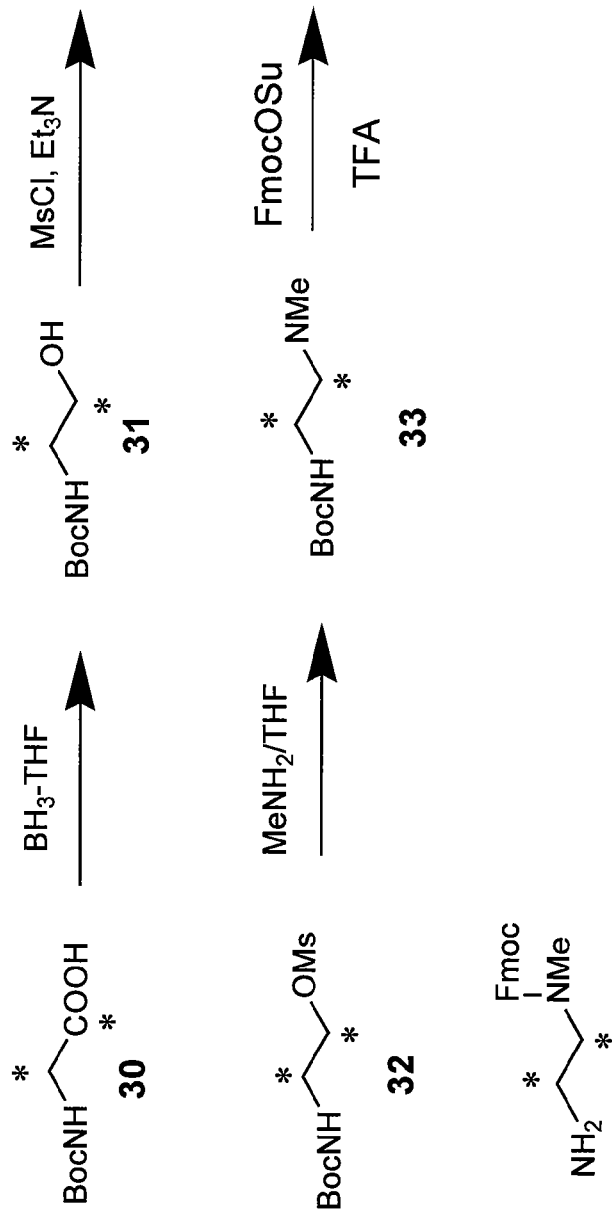

Synthetic Route to Encoded N-methyl ethylene diamine comprising four isotopically encoded sites Each * indicates where a $^{13}C$ is substituted of $^{12}C$ or $^{15}N$ is subsituted for $^{14}N$, as appropriate Synthetic Route to Encoded N-methyl ethylene diamine comprising four isotopically encoded sites Each * indicates where a $^{13}C$ is substituted of $^{12}C$ or $^{15}N$ is subsituted for $^{14}N$, as appropriate; $R^{12}$ is -H, -$CH_3$ or -$^{13}CH_3$ Synthetic Route to Encoded Piperazine Compounds Synthetic Route to Encoded Piperazine Compounds

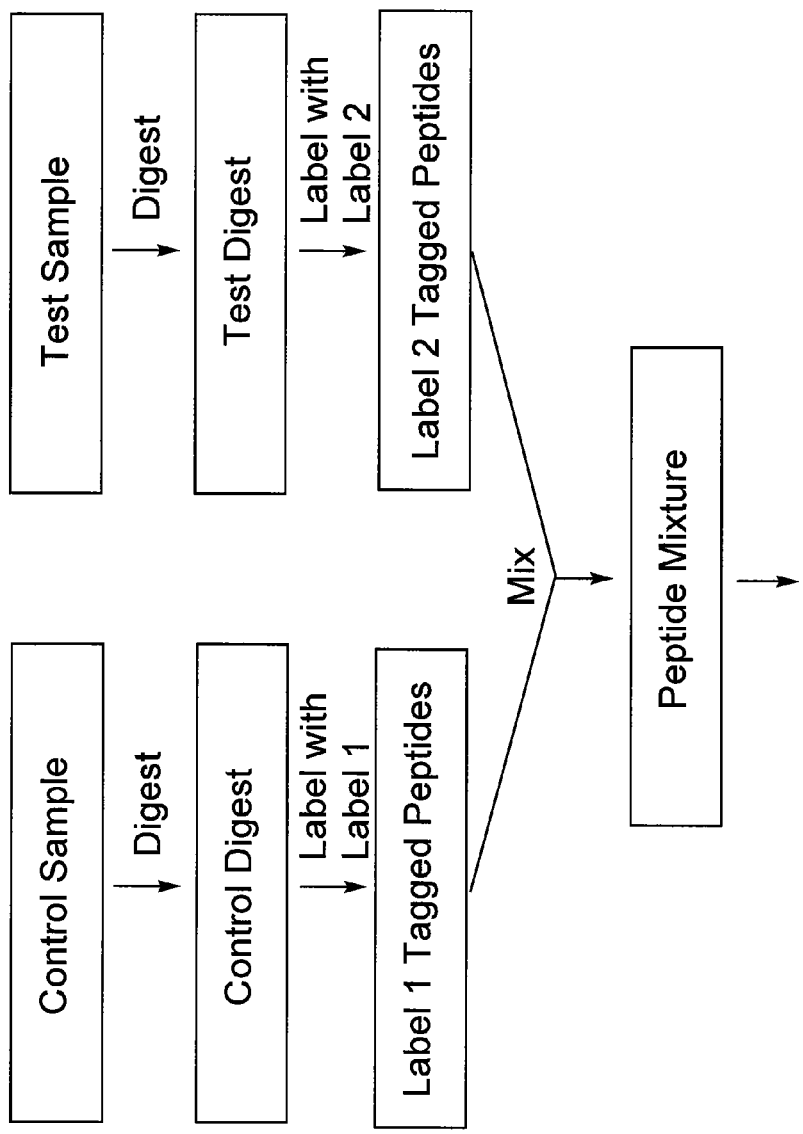

Elements of a Capture Support

Exemplary Capture Support

PEGA = Polyethylene glycolic acid

Possible Route to Some Exemplary Labeling Reagents

The variables Y, J, K, L, X$_1$, X$_2$, X$_3$, R$_1$, R$_2$ and Z' are as defined in the specification Possible Route to Some Exemplary Labeling Reagents The variables Y, J, K, L, X₁, X₂, X₃, R₁, R₂ and Z' are as defined in the specification MS Analysis of Uncoded Labeled Peptide MS/MS Analysis of Uncoded Labeled Peptide MS Analysis of Uncoded Labeled Peptide MS/MS Analysis of Uncoded Labeled Peptide MS Analysis of Uncoded Labeled Peptide MS/MS Analysis of Uncoded Labeled Peptide Fig. 25b
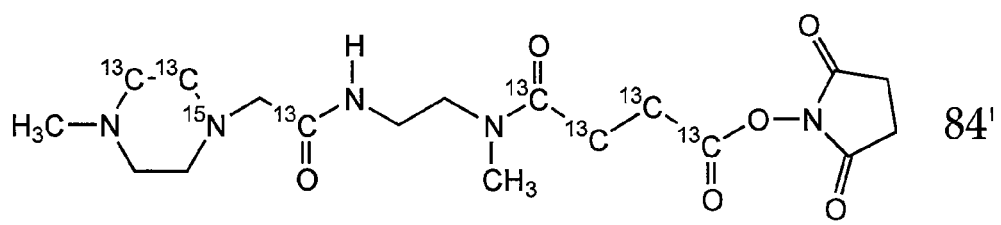
84'
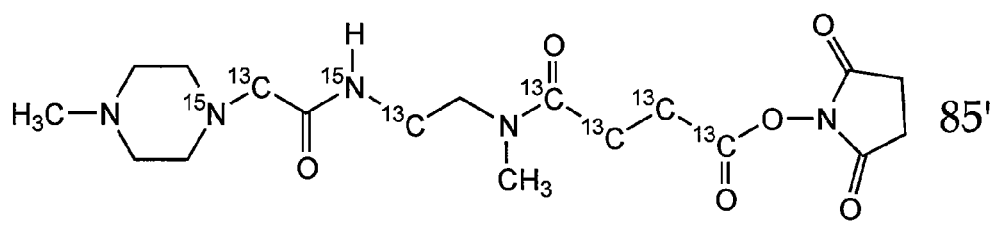
85'
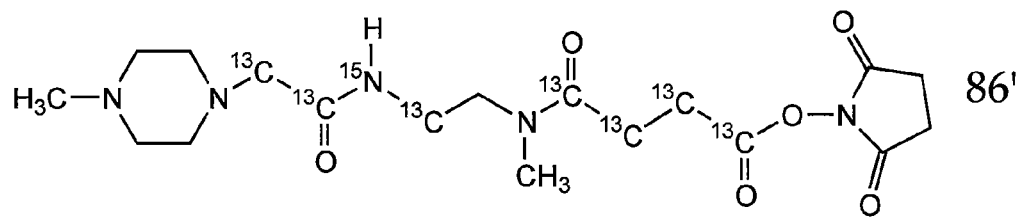
86'
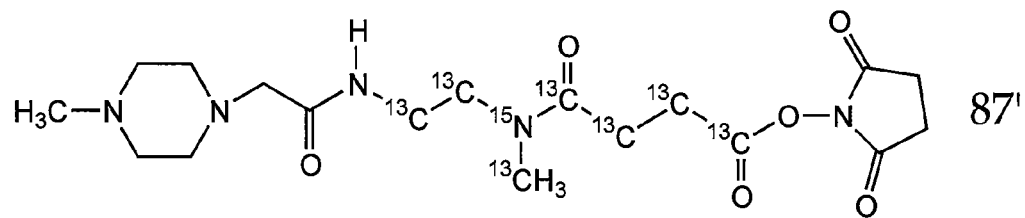
87'

Fig. 26a
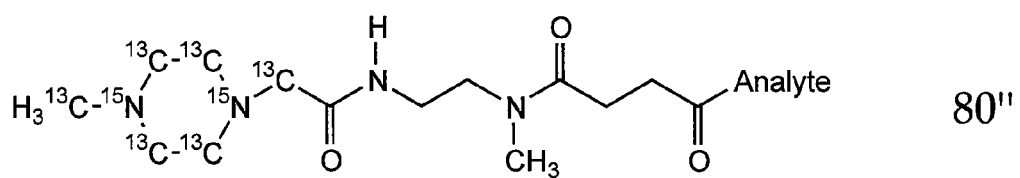 80"
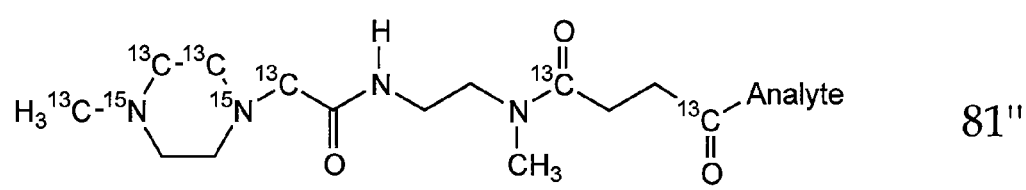 81"
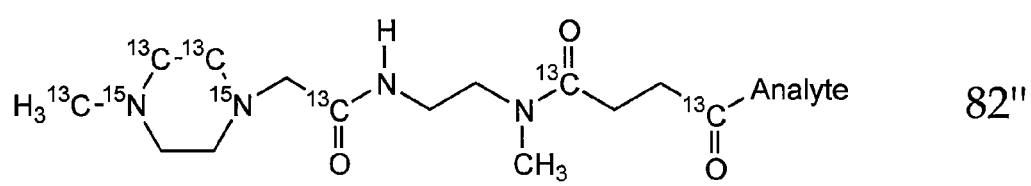 82"
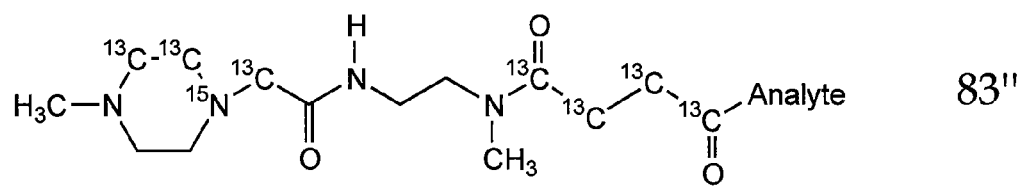 83"

Fig. 26b
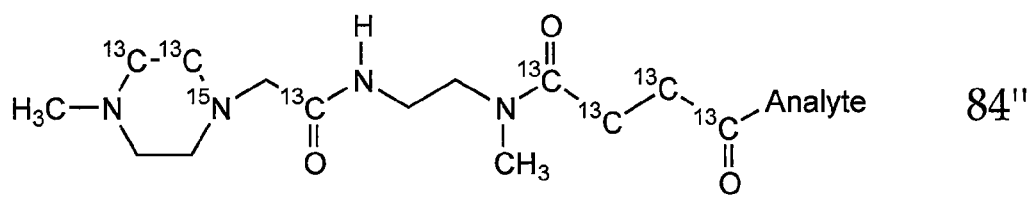 84"
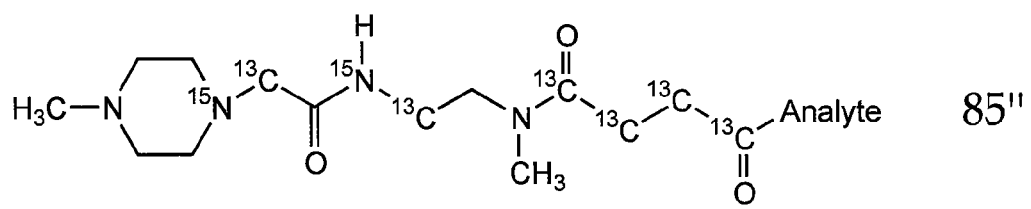 85"
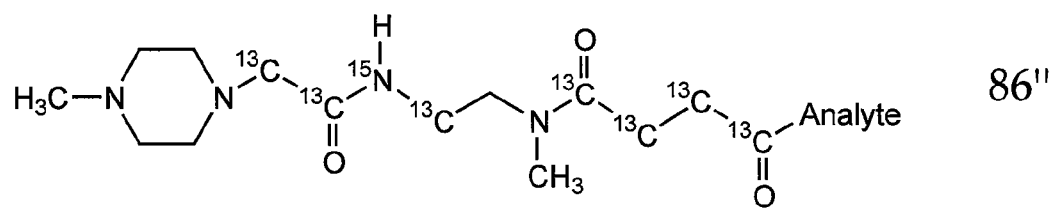 86"
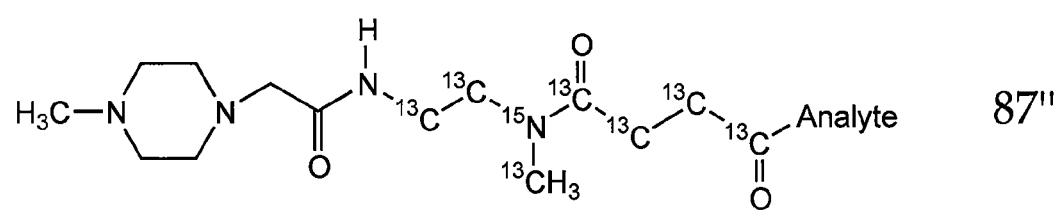 87"

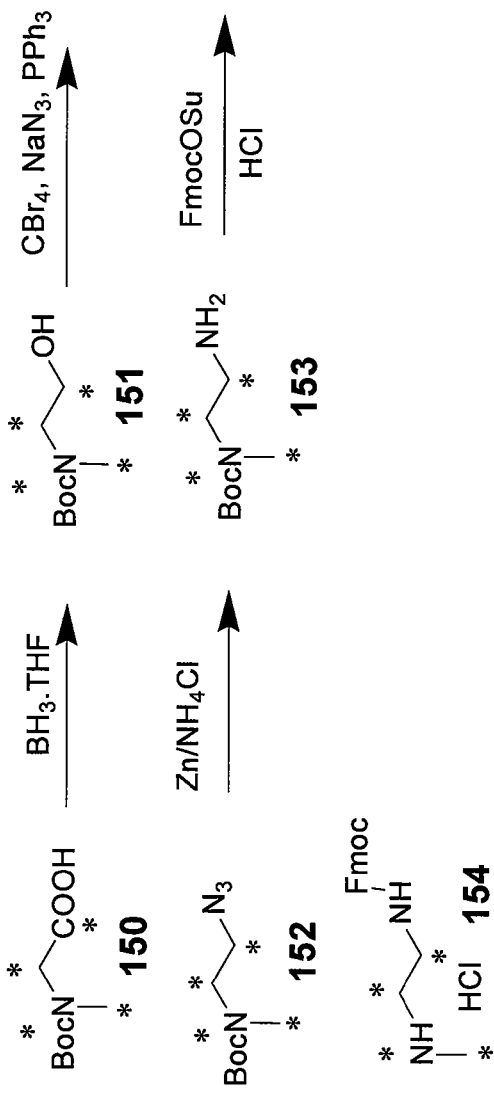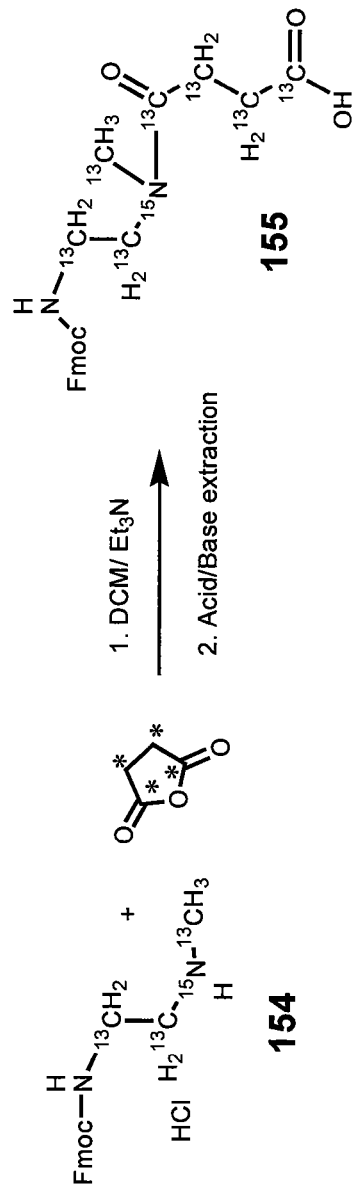
Fig. 29a
Fig. 29b

LABELING REAGENTS FOR ANALYTE DETERMINATION AND METHODS AND COMPOUNDS USED IN MAKING THE SAME

CROSS REFERENCE TO RELATED APPLICATIONS

This application claims to the benefit of U.S. Provisional Patent Application Ser. No. 60/761,711 filed Jan. 24, 2006 and U.S. Provisional Patent Application Ser. No. 60/764,216 filed Feb. 1, 2006, both incorporated herein by reference.

The section headings used herein are for organizational purposes only and should not be construed as limiting the subject matter described in any way.

FIELD

This invention pertains to methods, mixtures, kits and compositions pertaining to analyte determination by mass spectrometry.

INTRODUCTION

This invention pertains the determination of an analyte or analytes by mass analysis. An analyte can be any molecule of interest. Non-limiting examples of analytes include, but are not limited to, proteins, peptides, nucleic acids, carbohydrates, lipids, steroids and small molecules having a mass of less than 1500 daltons. Analytes can be determined using unique labeling reagents that permit the relative and/or absolute quantification of the analytes in complex mixtures. The labeling reagents can be used in sets for the analysis of complex sample mixtures wherein the labeling reagents can be isomeric and/or isobaric.

With reference to FIG. 1a, labeling reagents comprise a reporter moiety, a balance (or linker) moiety and a reactive group wherein the reactive group is substituted by the analyte in the analyte reacted form of the composition. Examples of labeling reagents and labeled analytes of this general formula have been disclosed in, for example, published copending and commonly owned United States Patent Application Serial Nos. US 2004-0219685 A1, US 2005-0114042 A1, US 2005-0147982 A1, US 2005-0147985 A1, US 2005-0147987 A1, US 2005-0148771 A1, US 2005-0148773 A1 and US 2005-0148774 A1. As discussed in the cited published United States Patent Applications, sets of isomeric and/or isobaric labeling reagents can be used to label, for example, the analytes of two or more different samples wherein the different labeling reagents of a set all have the same gross mass but wherein each reporter moiety can be uniquely encoded such that each reporter moiety of the set has a unique mass. Because all the reagents of the set can have the same gross mass but can comprise a reporter moiety of unique mass, the balance (or linker) will generally (but not necessarily) also comprise one or more heavy atom isotopes to thereby "balance" the mass of each unique reporter such that the reporter/linker combination of each labeling reagent of the set has the same gross mass.

An example of a new labeling reagent (or labeled analyte), as discussed more thoroughly herein, is illustrated in FIG. 1b. Although illustrated in unsubstituted form (except for $R_1$ and $R_2$), it is to be understood that the labeling reagent can be substituted or unsubstituted. In the illustration, certain bonds are shown as being fragmented to thereby release at least the unique reporter moiety, and typically but not necessarily the balance moiety, from the labeling reagent or labeled analyte. For the labeled analytes, each unique reporter ion (sometimes referred to as the signature ion) observed in the mass spectrometer can then be used to quantify the amount of analyte in a sample and/or sample mixture.

FIGS. 2a and 2b illustrate 9 different encoded versions of the basic structure illustrated in FIG. 1b (for example $R_1$ and $R_2$ can be, independently of the other, hydrogen or methyl) that can be used to facilitate at least a 9-plex experiment, wherein the asterisk (*) is used to illustrate where a $^{13}C$ atom is substituted for a $^{12}C$ atom or for where a $^{15}N$ atom is substituted for a $^{14}N$ atom, as appropriate. Proposed structures for the various reporter/signature ions are illustrated in FIG. 2c. However, if, for example, deuterium is also used to substitute for one or more hydrogen atoms and/or $^{18}O$ is substituted for $^{16}O$ in the reporter moiety and/or balance moiety, more than 9 different compounds can be envisioned such that greater than a 9-plex experiment could be performed. Such possibilities for further substitution of labeling reagents/labeled analytes of this general structure are discussed in more detail below with reference to FIGS. 6a and 6b.

An alternative set of isobaric compounds similar to those represented in FIGS. 2a and 2b, wherein $R_1$ and $R_2$ can be used to form a 6-membered ring, are illustrated in FIGS. 3a and 3b. These labeling reagents can form the same set of 9 different reporter/signature ions whose proposed structures are illustrated in FIG. 2c. The ease with which alternative structures having the requisite properties for analyte analysis can be prepared illustrates the general applicability of the embodiments of this invention.

Generally, labeling reagents, labeled analytes and some intermediates to the labeling reagents and/or labeled analytes can be represented by compounds of formula I;

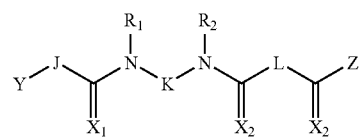

including a salt form thereof and/or a hydrate form thereof, wherein Z can be —OH, —SH, —O⁻V⁺, —S⁻V⁺, a reactive group that is capable of reacting with a functional group of the analyte to thereby form the labeled analyte, a leaving group of a reactive group wherein the leaving group leaves upon reaction of the labeling reagent with a nucleophilic functional group of an analyte or a covalently linked analyte and wherein the atoms or groups V⁺, $X_1$, $X_2$, $R_1$, $R_2$, Y, J, K and L are described in more detail below.

Accordingly, in some embodiments analytes can be labeled by reaction of the analyte with a labeling reagent represented by compounds of formula I';

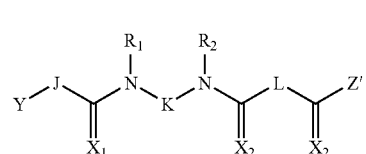

including a salt form thereof and/or a hydrate form thereof, wherein Z' represents the reactive group, or the leaving group of the reactive group, that is capable of reacting with a functional group of the analyte to thereby form the labeled analyte and wherein the atoms or groups $X_1$, $X_2$, $R_1$, $R_2$, Y, J, K and L are described in more detail below. The labeling reagents can be used in sets, wherein the sets comprise isomeric and/or isobaric compounds, whereby the labeled analytes can likewise be isomeric and/or isobaric.

Further, in some embodiments a labeled analyte therefore can be represented by formula I″;

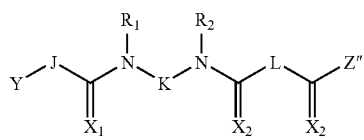

including a salt form thereof and/or a hydrate form thereof, wherein Z″ represents the analyte covalently linked to the labeling reagent (possibly through additional atoms or groups of the reactive group) and wherein the atoms or groups $X_1$, $X_2$, $R_1$, $R_2$, Y, J, K and L are described in more detail below.

Moreover, in some embodiments, intermediates of the labeling reagents can be represented by formula I‴;

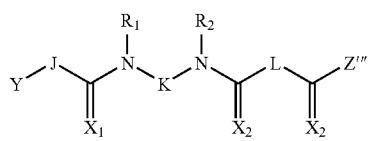

including a salt form thereof and/or a hydrate form thereof, wherein Z‴ represents —OH, —SH, —O⁻V⁺ or —S⁻V⁺ and wherein the atoms or groups V⁺, $X_1$, $X_2$, $R_1$, $R_2$, Y, J, K and L are described in more detail below. Said intermediates can be used, for example, to produce the labeling reagents disclosed herein, including in-situ generation of the labeling reagent(s), wherein said in-situ generated labeling reagents can be used to label analytes.

In the illustrated compounds, the group Y-J- represents the reporter moiety. Consequently, labeling reagents of an isomeric and/or isobaric set can be encoded such that each different labeling reagent of the set has the same gross mass but wherein the group Y-J- of each different labeling reagent of the set is uniquely encoded, for example by using one or more isotopically enriched sites, such that when the bond between the group J, of the group Y-J-, and the remainder of the labeled analyte (or a fragment thereof) fragments in a mass spectrometer (see FIG. 1c), a reporter ion of unique mass can be produced. The peak intensity for the ion associated with the reporter moiety (i.e. the signature ion or reporter ion) can be correlated with the amount (often expressed as a concentration and/or quantity) of the labeled analyte in the sample analyzed. Thus, sets of isomeric and/or isobaric labeling reagents can be used to label the analytes of two or more different samples wherein the labeling reagent can be different for each different sample and wherein the labeling reagent can comprise a reporter moiety of unique mass that can be associated with the sample from which the labeled analyte originated. Hence, information, such as the presence and/or amount of each reporter moiety, can be correlated with the analyte in two or more different samples even from the analysis of a complex mixture of labeled analytes derived by mixing the products of the labeling of a plurality of different samples.

As described herein, sets of nine, or more, isomeric and/or isobaric labeling reagents can be made thereby permitting experiments of 9-plex or greater (An illustration of one exemplary analysis can be found in FIGS. 19a and 19b). For example, it is possible to simultaneously identify and/or quantify an analyte in 9 (or more) different samples that have each been differentially labeled and then mixed. Such an analysis can be achieved by determination of the unique reporter ions (that may have the structures illustrated in FIG. 2c) from the mixture of 9 different samples each labeled with a different labeling reagent of the set illustrated in either of FIGS. 2a/2b or 3a/3b. Thus, embodiments of this invention are particularly well suited for the multiplex analysis of complex sample mixtures. For example, some embodiments of this invention can be used in proteomic analysis and/or genomic analysis as well as for correlation studies related to genomic and proteomic analysis. Some embodiments of this invention can also be used for small molecule analysis, such as for lipid, steroid or amino acid analysis. Experimental analysis for which the isomeric and/or isobaric reagents can be used includes, but is not limited to, time course studies, biomarker analysis, multiplex proteomic analysis, mudpit experiments, affinity pull-downs, determination of post-translational modifications (PTMs) (see for example published United States Patent Application No. US 2005-0208550 A1) and multiple control experiments.

BRIEF DESCRIPTION OF THE DRAWINGS

The skilled artisan will understand that the drawings, described below, are for illustration purposes only. The drawings are not intended to limit the scope of the present teachings in any way.

FIG. 1a is an illustration of the elements of a labeling reagent or labeled analyte and their fragmentation characteristics.

FIG. 1b is an illustration of the general elements of an exemplary N-methyl piperazine based labeling reagent or labeled analyte and its fragmentation characteristics.

FIG. 1c is an illustration of the general elements of a labeled analyte of the identified general formula and its fragmentation characteristics.

FIG. 2b is an illustration of various isobaric compounds that, when considered with the compounds illustrated in FIG. 2a, can form a 9-plex set.

FIG. 3a is an illustration of various isobaric compounds that, when considered with the compounds illustrated in FIG. 3b, can form a 9-plex set, wherein the balance comprises a ring structure.

FIG. 4a is an illustration of exemplary isobaric compounds.

FIG. 4b is an illustration of exemplary isomeric isobaric compounds.

FIG. 5 is an illustration of the process of cleaving an exemplary support bound labeled analyte from a support.

FIG. 7c is an illustration of Steps 6-7 of an exemplary synthesis of an exemplary labeling reagent.

FIG. 9a is a Table illustrating the isotopically encoded source materials that can be used to prepare various isobaric compounds by practice of the invention(s) disclosed herein.

FIG. 9b is a Table illustrating the isotopically encoded source materials that can be used to prepare various isobaric compounds by practice of the invention(s) disclosed herein.

FIG. 10a is a Table illustrating the isotopically encoded source materials that can be used to prepare various isobaric compounds by practice of the invention(s) disclosed herein.

FIG. 10b is a Table illustrating the isotopically encoded source materials that can be used to prepare various isobaric compounds by practice of the invention(s) disclosed herein.

FIG. 10c is a Table illustrating the isotopically encoded source materials that can be used to prepare various isobaric compounds by practice of the invention(s) disclosed herein.

FIG. 12a is an illustration of one possible synthetic route to an encoded N-methyl ethylene diamine comprising two isotopically encoded sites.

FIG. 13 is an illustration of one possible workflow for processing a test sample and a control sample using a set of isobaric labeling reagents (i.e. Label 1 and Label 2).

FIG. 19b is an illustration of the result of MS/MS analysis of the 9 differentially labeled peptides (of a particular m/z value) selected from the MS analysis depicted in FIG. 19a.

FIG. 25b is an illustration of various isobaric labeling reagents that, when considered with the compounds illustrated in FIG. 25a, can form an 8-plex set.

FIG. 26a is an illustration of various isobaric labeled analytes that, when considered with the compounds illustrated in FIG. 26b, can form an 8-plex set.

FIG. 26b is an illustration of various isobaric labeled analytes that, when considered with the compounds illustrated in FIG. 26a, can form an 8-plex set.

FIG. 29a is an illustration of one possible synthetic route to an encoded N-methyl ethylene diamine comprising four isotopically encoded sites.

FIG. 29b is an illustration of the synthesis of Fmoc-NH—CH$_2$CH$_2$—N(Me)-CO—CH$_2$CH$_2$—COOH comprising eight isotopically encoded sites.

Figure 1D:
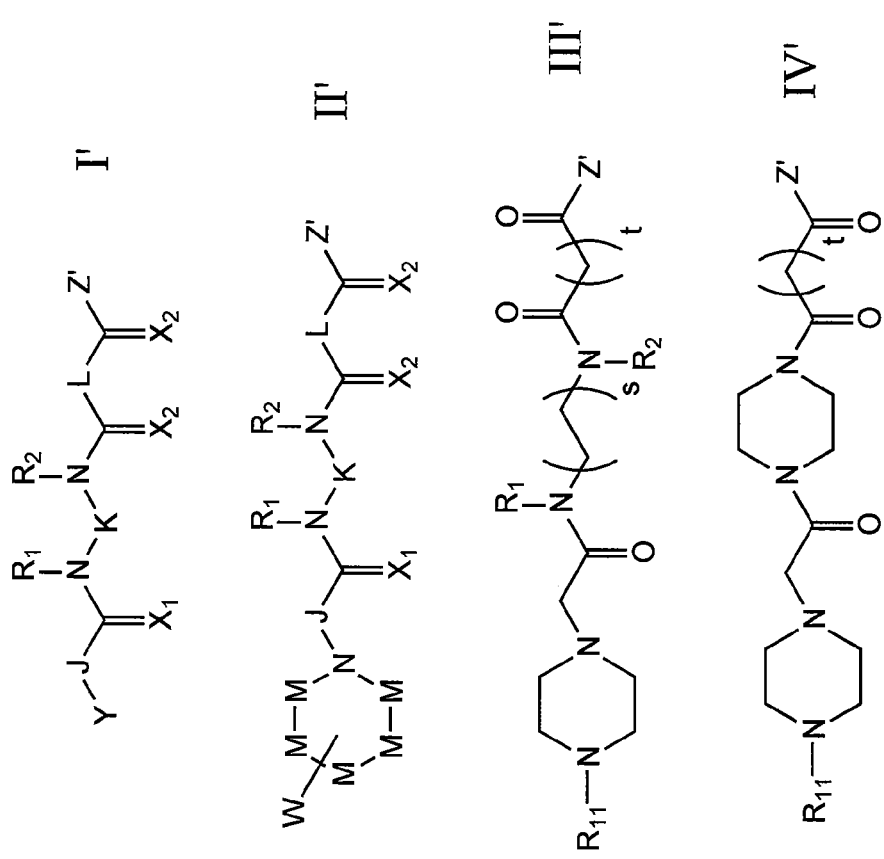
FIG. 1d is an illustration of the general formulas of some exemplary isobaric labeling reagents.

All literature and similar materials cited in this application, including but not limited to, patents, patent applications, articles, books, treatises, and internet web pages, regardless of the format of such literature and similar materials, are expressly incorporated by reference herein in their entirety for any and all purposes.

Definitions:

For the purposes of interpreting of this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used). The use of "or" herein means "and/or" unless stated otherwise or where the use of "and/or" is clearly inappropriate. The use of "a" herein means "one or more" unless stated otherwise or where the use of "one or more" is clearly inappropriate. The use of "comprise," "comprises," "comprising" "include," "includes," and "including" are interchangeable and not intended to be limiting. Furthermore, where the description of one or more embodiments uses the term "comprising," those skilled in the art would understand that in some specific instances, the embodiment or embodiments can be alternatively described using language "consisting essentially of" and/or "consisting of."

a.) As used herein, "analyte" refers to a molecule of interest that may be determined. Non-limiting examples of analytes include, but are not limited to, proteins, peptides, nucleic acids (either DNA or RNA), carbohydrates, lipids, steroids and other small molecules with a molecular weight of less than 1500 daltons (Da). The source of the analyte, or the sample comprising the analyte, is not a limitation as it can come from any source. The analyte or analytes can be natural or synthetic. Non-limiting examples of sources for the analyte, or the sample comprising the analyte, include cells or tissues, or cultures (or subcultures) thereof. Other non-limiting examples of analyte sources include, but are not limited to, crude or processed cell lysates, body fluids, tissue extracts, cell extracts or fractions (or portions) from a separations process such as a chromatographic separation, a 1 D electrophoretic separation, a 2D electrophoretic separation or a capillary electrophoretic separation. Body fluids include, but are not limited to, blood, urine, feces, spinal fluid, cerebral fluid, amniotic fluid, lymph fluid or a fluid from a glandular secretion. By processed cell lysate we mean that the cell lysate is treated, in addition to the treatments needed to lyse the cell, to thereby perform additional processing of the collected material. For example, the sample can be a cell lysate comprising one or more analytes that are peptides formed by treatment of the cell lysate with one or more proteolytic enzymes to thereby digest precursor peptides and/or proteins.

b.) Except as when clearly not intended based upon the context in which it is being used (e.g. when made in reference to a specific structure that dictates otherwise), "ester" refers to both an ester and/or a thioester.

c.) As used herein, "fragmentation" refers to the breaking of a covalent bond.

d.) As used herein, "fragment" refers to a product of fragmentation (noun) or the operation of causing fragmentation (verb).

e.) As used herein, "hydrate form" refers to any hydration state of a compound or a mixture or more than one hydration state of a compound. For example, a labeling reagent discussed herein can be a hemihydrate, a monohydrate, a dihydrate, etc. Moreover, a sample of a labeling reagent described herein can comprise monohydrate, dihydrate and hemihydrate forms simultaneously.

f.) As used herein, a halogen group refers to —F, —Cl, —Br, or —I.

g.) As used herein with respect to a compound, "isotopically enriched" refers to a compound (e.g. labeling reagent) that has been enriched with one or more heavy atom isotopes (e.g. stable isotopes such as Deuterium, $^{13}$C, $^{15}$N, $^{18}$O, $^{37}$Cl or $^{81}$Br). In some embodiments, unstable isotopes can also be used (e.g. $^{14}$C or $^{3}$H). By "enriched" we mean that the amount of heavy atom isotope exceeds natural isotopic abundance. In various embodiments, the isotopically enriched compound can comprise 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more isotopically enriched sites. Because isotopic enrichment is not 100% effective, there can be impurities in a sample of the compound that are of lesser states of enrichment and these will have a lower mass. Likewise, because of over-enrichment (e.g. undesired enrichment) and because of natural isotopic abundance, there can be impurities in a sample of the compound that are of greater mass. In some embodiments, each incorporated heavy atom isotope can be present at an isotopically enriched site in at least 80 percent isotopic purity. In some embodiments, each incorporated heavy atom isotope can be present at an isotopically enriched sited in at least 93 percent isotopic purity. In some embodiments, each incorporated heavy atom isotope can be present at an isotopically enriched site in at least 96 percent isotopic purity. In some embodiments, each incorporated heavy atom isotope can be present at an isotopically enriched site in at least 98 percent purity.

h.) As used herein, "isotopically enriched site" refers to the position in a compound where a heavy atom isotope is substituted for a light version of the atom (e.g. substitution of $^{13}$C for $^{12}$C, $^{18}$O for $^{16}$O, $^{15}$N for $^{14}$N or deuterium for hydrogen).

i.) As used herein with respect to a compound, "light" refers to the compound as not being enriched with a heavy atom isotope. As used herein with respect to an atom, "light" refers to the lowest mass isotope of the atom. As used herein with respect to a compound, "heavy" refers to the compound as being enriched with at least one heavy atom isotope. As used herein with respect to an atom, "heavy" refers to a heavy mass isotope of the atom.

j.) As used herein, "labeling reagent" refers to a moiety suitable to mark an analyte for determination. The term label is synonymous with the terms tag and mark and other equivalent terms and phrases. For example, a labeled analyte can also be referred to as a tagged analyte or a marked analyte. Accordingly the terms "label", "tag", "mass tag", "mark" and derivatives of these terms, are equivalent and interchangeable and refer to a moiety suitable to mark, or that has marked, an analyte for determination. Sometimes a labeling reagent can be referred to a tagging reagent or a mass-tagging reagent.

k.) As used herein, "natural isotopic abundance" refers to the level (or distribution) of one or more heavy isotopes found in a compound based upon the natural prevalence of an isotope or isotopes in nature. For example, a natural compound obtained from living plant matter will typically contain about 1.08% $^{13}$C relative to $^{12}$C.

l.) As used herein, isobars are structurally indistinguishable compounds (except for isotopic content and/or distribution of heavy atom isotopes) of the same nominal gross mass. For the avoidance of any doubt, compounds 1-4 of FIG. 4a are isobaric by the definition set forth herein. By comparison, as used herein isomers are structurally distinguishable compounds of the same nominal gross mass. Exemplary isomeric isobars are illustrated in FIG. 4b.

m.) As used herein, "support", "solid support", "solid carrier" or "resin" means any solid phase material. Solid support encompasses terms such as "support", "synthesis support", "solid phase", "surface" "membrane" and/or "support". A solid support can be composed of organic polymers such as polystyrene, polyethylene, polypropylene, polyfluoroethylene, polyethyleneoxy, and polyacrylamide, as well as co-polymers and grafts thereof. A solid support can also be inorganic, such as glass, silica, controlled-pore-glass (CPG), or reverse-phase silica. The configuration of a solid support can be in the form of beads, spheres, particles, granules, a gel, a membrane or a surface. Surfaces can be planar, substantially planar, or non-planar. Solid supports can be porous or non-porous, and can have swelling or non-swelling characteristics. A solid support can be configured in the form of a well, depression or other container, vessel, feature or location. A plurality of solid supports can be configured in an array at various locations, addressable for robotic delivery of reagents, or by detection methods and/or instruments.

n.) As used herein, "sample, or a fraction thereof" or "sample fraction" can be used to refer to a fraction of a sample. The fraction of the sample can be generated either by simply withdrawing a fraction of a sample else it can be generated by performing a separations process that results in the sample being fractionated into two or more fractions. Unless the content of the description indicates otherwise, these phrases are equivalent and interchangeable and refer to either type of creation of a fraction (or portion) of a sample.

o.) As used herein, "signature ion" and "reporter ion" are interchangeable and both refer to the reporter ion of unique mass produced from the reporter moiety by fragmentation of a labeling reagent or labeled analyte. The signature ion or reporter ion identifies the unique labeling reagent used to label an analyte and its peak intensity in MS/MS analysis can be correlated with the amount of labeled analyte present in the sample that is analyzed. As used herein, the signature ion or reporter ion is sometimes merely referred to as a reporter. As used herein, the reporter moiety is also sometimes merely referred to a reporter. It is to be understood that the reporter moiety refers to the group attached to a labeling reagent, labeled analyte or fragment thereof and the reporter ion refers to the fragment ion generated upon fragmentation of the bond that links the reporter moiety to the labeling reagent, labeled analyte or a fragment thereof. Accordingly, the context in which the word "reporter" is used will indicate its intended meaning. It also is to be understood that the phrase "unique reporter moiety" is equivalent to, and interchangeable with, "reporter moiety of unique mass" and that "unique reporter ion" is equivalent to, and interchangeable with, "reporter ion of unique mass".

p.) As used herein, the term "salt form" includes a salt of a compound or a mixture of salts of a compound. In addition, zwitterionic forms of a compound are also included in the term "salt form." Salts of compounds having an amine, or other basic group can be obtained, for example, by reaction with a suitable organic or inorganic acid, such as hydrogen chloride, hydrogen bromide, acetic acid, perchloric acid and the like. Compounds with a quaternary ammonium group may also contain a counteranion such as chloride, bromide, iodide, acetate, perchlorate and the like. Salts of compounds having a carboxylic acid, or other acidic functional group, can be prepared by reacting the compound with a suitable base, for example, a hydroxide base. Accordingly, salts of acidic functional groups may have a countercation, such as sodium, potassium, magnesium, calcium, etc.

q.) As used herein, "synthetic compound" refers to a compound that is created by manipulation of processes including the manipulation of naturally occurring pathways. Thus, a synthetic compound can be produced using synthetic chemistry techniques. However, as used herein, "synthetic compound" is also intended to include compounds that are produced, for example, by enzymatic methods, including for example, feeding isotopically enriched compounds to organisms, such as bacteria or yeast, that alter them to thereby produce the isotopically enriched labeling reagents, or intermediates of the labeling reagents, described herein.

r.) As used herein, "synthetically enriched" or "enriched synthetically" refers to the manipulation of a synthetic or natural process to thereby produce the isotopically enriched labeling reagents, or intermediates to the labeling reagents, described herein.

s.) It is well accepted that the mass of an atom or molecule can be approximated, often to the nearest whole number atomic mass unit or the nearest tenth or hundredth of an atomic mass unit. As used herein, "gross mass" refers to the absolute mass as well as to the approximate mass within a range where the use of isotopes of different atom types are so close in mass that they are the functional equivalent for the purpose of balancing the mass of the reporter and/or linker moieties (so that the gross mass of the reporter/linker combination is the same within a set or kit of isomeric and/or isobaric labeling reagents) whether or not the very small difference in mass of the different isotopes types used can be detected.

For example, the common isotopes of oxygen have a gross mass of 16.0 (actual mass 15.9949) and 18.0 (actual mass 17.9992), the common isotopes of carbon have a gross mass of 12.0 (actual mass 12.00000) and 13.0 (actual mass 13.00336) and the common isotopes of nitrogen have a gross mass of 14.0 (actual mass 14.0031) and 15.0 (actual mass 15.0001). Whilst these values are approximate, one of skill in the art will appreciate that if one uses the $^{18}$O isotope at an isotopically enriched site within one label of a set, the additional 2 mass units (over the isotope of oxygen having a gross mass of 16.0) can, for example, be compensated for in a different label of the set comprising $^{16}$O by incorporating, elsewhere in the label, two carbon $^{13}$C atoms, instead of two $^{12}$C atoms, two $^{15}$N atoms, instead of two $^{14}$N atoms or even one $^{13}$C atom and one $^{15}$N atom, instead of a $^{12}$C and a $^{14}$N, to compensate for the $^{18}$O. In this way the two different labels of the set can have the same gross mass since the very small actual differences in mass between the use of two $^{13}$C atoms (instead of two $^{12}$C atoms), two $^{15}$N atoms (instead of two $^{14}$N atoms), one $^{13}$C and one $^{15}$N (instead of a $^{12}$C and $^{14}$N) or one $^{18}$O atom (instead of one $^{16}$O atom), to thereby achieve an increase in mass of two Daltons in all of the labels of the set or kit, is not an impediment to the nature of the analysis.

This can be illustrated with reference to FIG. 4a. In FIG. 4a, the reporter/linker combination of compound 3 (FIG. 4a;

molecular formula: $C_5{}^{13}CH_{11}{}^{15}N_2O$) has two $^{15}N$ atoms and one $^{13}C$ atom and a total theoretical mass of 130.085. By comparison, the reporter/linker moiety of isobar 1 (FIG. 4a; molecular formula $C_5{}^{13}CH_{11}N_2{}^{18}O$) has one $^{18}O$ atom and one $^{13}C$ atom and a total theoretical mass of 130.095. Compounds 1 and 3 can be isobars that are structurally indistinguishable, except for heavy atom isotope content, although there can be a slight absolute mass difference of the reporter/linker moiety (mass 130.095 vs. mass 130.085 respectively). However, the gross mass of the reporter/linker moiety of compounds 1 and 3 is 130.1 for the purposes of this invention since this is not an impediment to the analysis whether or not the mass spectrometer is sensitive enough to measure the small difference between the absolute mass of the reporter ions generated from isobars 1 and 3.

Similarly with reference to FIG. 4b, two isomeric isobars are illustrated wherein the mass of the reporter/linker moiety of compounds 5 and 6 is 144.111 and 144.100, respectively. The gross mass of the reporter/linker moiety of these compounds is 144.1 for the purposes of this invention since it is not an impediment to the analysis whether or not the mass spectrometer is sensitive enough to measure the small difference between the absolute mass of the reporter ions generated from compounds 5 and 6.

From FIGS. 4a and 4b, it is clear that the distribution of the same heavy atom isotopes within a structure is not the only consideration for the creation of sets of isomeric and/or isobaric labeling reagents. It is possible to mix heavy atom isotope types to achieve isomers and/or isobars of a desired gross mass. In this way, both the selection (combination) of heavy atom isotopes as well as their distribution is available for consideration in the production of the isomeric and/or isobaric labeling reagents useful for embodiments of this invention.

t.) As used herein, the term "alkyl" refers to a straight chained or branched $C_2$-$C_8$ hydrocarbon or a cyclic $C_3$-$C_8$ hydrocarbon (i.e. a cycloalkyl group such as a cyclopropyl group, a cyclobutyl group, a cyclopentyl group, a cyclohexyl group or a cyclohexylmethylene group) that can be completely saturated. When used herein, the term "alkyl" refers to a group that may be substituted or unsubstituted. The term "alkyl" is also intended to refer to those compounds wherein one or more methylene groups in the alkyl chain can be replaced by a heteroatom such as —O—, —Si— or —S—. In some embodiments, alkyl groups can be straight chained or branched $C_2$-$C_6$ hydrocarbons or cyclic $C_3$-$C_6$ hydrocarbons that can be completely saturated.

u.) As used herein, the term "alkylene" refers to a straight or branched alkyl chain or a cyclic alkyl group that comprises at least two points of attachment to at least two moieties (e.g., —{CH$_2$}— (methylene), —{CH$_2$CH$_2$}—, (ethylene),

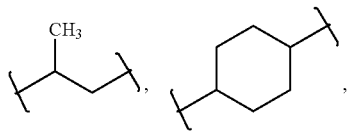

etc., wherein the brackets indicate the points of attachment. When used herein the term "alkylene" refers to a group that may be substituted or unsubstituted. The term "alkylene" is also intended to refer to those compounds wherein one or more methylene groups, if any, in an alkyl chain of the alkylene group can be replaced by a heteroatom such as —O—, —Si— or —S—. In some embodiments, an alkylene group can be a $C_1$-$C_{10}$ hydrocarbon. In some embodiments, an alkylene group can be a $C_2$-$C_6$ hydrocarbon.

v.) As used herein, the term "alkenyl" refers to a straight chained or branched $C_2$-$C_8$ hydrocarbon or a cyclic $C_3$-$C_8$ hydrocarbon that comprises one or more double bonds. When used herein, the term "alkenyl" refers to a group that can be substituted or unsubstituted. The term "alkenyl" is also intended to refer to those compounds wherein one or more methylene groups, if any, in an alkyl chain of the alkenyl group can be replaced by a heteroatom such as —O—, —Si— or —S—. In some embodiments, alkenyl groups can be straight chained or branched $C_2$-$C_6$ hydrocarbons or cyclic $C_3$-$C_6$ hydrocarbons that comprise one or more double bonds.

w.) As used herein, the term "alkenylene" refers to an alkenyl group that comprises two points of attachment to at least two moieties. When used herein the term "alkenylene" refers to a group that may be substituted or unsubstituted. The term "alkenylene" is also intended to refer to those compounds wherein one or more methylene groups, if any, in an alkyl chain of the alkenylene group can be replaced by a heteroatom such as —O—, —Si— or —S—.

x.) As used herein, the term "alkynyl" refers to a straight chained or branched $C_2$-$C_8$ hydrocarbon or a cyclic $C_3$-$C_8$ hydrocarbon that comprises one or more triple bonds. When used herein, the term "alkynyl" refers to a group that may be substituted or unsubstituted. The term "alkynyl" is also intended to refer to those compounds wherein one or more methylene groups, if any, in an alkyl chain of the alkynyl group can be replaced by a heteroatom such as —O—, —Si— or —S—. In some embodiments, alkynyl groups can be straight chained or branched $C_2$-$C_6$ hydrocarbons or cyclic $C_3$-$C_6$ hydrocarbons that have one or more triple bonds.

y.) As used herein, the term "alkynylene" refers to an alkynyl group that comprises two points of attachment to at least two moieties. When used herein the term "alkynylene" refers to a group that may be substituted or unsubstituted. The term "alkynylene" is also intended to refer to those compounds wherein one or more methylene groups, if any, in an alkyl chain of the alkynylene group can be replaced by a heteroatom such as —O—, —Si— or —S—.

z.) As used herein, the term "aliphatic" refers to any of the straight, branched, or cyclic alkyl, alkenyl, and alkynyl moieties as defined above. When used herein the term "aliphatic" refers to a group that may be substituted or unsubstituted.

aa.) As used herein, the term "aryl", either alone or as part of another moiety (e.g., arylalkyl, etc.), refers to carbocyclic aromatic groups such as phenyl. Aryl groups also include fused polycyclic aromatic ring systems in which a carbocyclic aromatic ring is fused to another carbocyclic aromatic ring (e.g., 1-naphthyl, 2-naphthyl, 1-anthracyl, 2-anthracyl, etc.) or in which a carbocyclic aromatic ring is fused to one or more carbocyclic non-aromatic rings (e.g., tetrahydronaphthylene, indan, etc.). As used herein, the term "aryl" refers to a group that may be substituted or unsubstituted.

ab.) As used herein, the term "heteroaryl," refers to an aromatic heterocycle that comprises 1, 2, 3 or 4 heteroatoms selected, independently of the others, from nitrogen, sulfur and oxygen. As used herein, the term "heteroaryl" refers to a group that may be substituted or unsubstituted. A heteroaryl may be fused to one or two rings, such as a cycloalkyl, an aryl, or a heteroaryl ring. The point of attachment of a heteroaryl to a molecule may be on the heteroaryl, cycloalkyl, heterocycloalkyl or aryl ring, and the heteroaryl group may be attached through carbon or a heteroatom. Examples of heteroaryl groups include imidazolyl, furyl, pyrrolyl, thienyl, thiazolyl, isoxazolyl, isothiazolyl, thiadiazolyl, oxadiazolyl, pyridinyl, pyrimidyl, pyrazinyl, pyridazinyl, quinolyl, isoquinolinyl, indazolyl, benzoxazolyl, benzisooxazolyl, benzofuryl, benzothiazolyl, indolizinyl, imidazopyridinyl, pyrazolyl, triazolyl, oxazolyl, tetrazolyl, benzimidazolyl, benzoisothiazolyl, benzothiadiazolyl, benzoxadiazolyl, indolyl, tetrahydroindolyl, azaindolyl, imidazopyridyl, quinazolinyl, purinyl, pyrrolo[2,3]pyrimidyl, pyrazolo[3,4]pyrimidyl or benzo (b)thienyl, each of which can be optionally substituted.

ac.) As used herein, the term "arylene" refers to an aryl or heteroaryl group that comprises at least two points of attachment to at least two moieties (e.g., phenylene, etc.). The point of attachment of an arylene fused to a carbocyclic, non-aromatic ring may be on either the aromatic, non-aromatic ring. As used herein, the term "arylene" refers to a group that may be substituted or unsubstituted.

ad.) As used herein, the term "arylalkyl" refers to an aryl or heteroaryl group that is attached to another moiety via an alkylene linker. As used herein, the term "arylalkyl" refers to a group that may be substituted or unsubstituted. The term "arylalkyl" is also intended to refer to those compounds wherein one or more methylene groups, if any, in the alkyl chain of the arylalkyl group can be replaced by a heteroatom such as —O—, —Si— or —S—.

ae.) As used herein, the term "arylalkylene" refers to an arylalkyl group that has at least two points of attachment to at least two moieties. The second point of attachment can be on either the aromatic ring or the alkylene group. As used herein, the term "arylalkylene" refers to a group that may be substituted or unsubstituted. The term "arylalkylene" is also intended to refer to those compounds wherein one or more methylene groups, if any, in the alkyl chain of the arylalkylene group can be replaced by a heteroatom such as —O—, —Si— or —S—. When an arylalkylene is substituted, the substituents may be on either or both of the aromatic ring or the alkylene portion of the arylalkylene.

af.) As used herein, the terms "optionally substituted" and "substituted or unsubstituted" are equivalent and interchangeable. Suitable substituents for any an alkyl, an alkylene, an alkenyl, an alkenylene, an alkynyl, an alkynylene, an aryl, an aryl alkyl, an arylene, a heteroaryl or an arylalkylene group includes any substituent that is stable under the reaction conditions used in embodiments of this invention. Non limiting examples of suitable substituents can include: an alkyl (e.g., methyl, ethyl, n-propyl, isopropyl, n-butyl, isobutyl, sec butyl, t-butyl, cyclohexyl, etc.) group, a haloalkyl (e.g., trifluoromethyl, 2,2,2-trifluoroethyl-, etc.) group, an alkoxy (e.g., methoxy, ethoxy, etc.) group, an aryl (e.g., phenyl) group, an arylalkyl (e.g., benzyl) group, a nitro group, a cyano group, a quaternized nitrogen atom or a halogen group (e.g., fluorine, chlorine, bromine and/or iodine) group.

In addition, any portion of an alkyl, an alkylene, an alkenyl, an alkenylene, an alkynyl, an alkynylene, an aryl, an aryl alkyl, an arylene, a heteroaryl or an arylalkylene group may also be substituted with =O or =S.

ah.) As used herein, the term "active ester" refers to compounds that can react readily under basic conditions with amines, alcohols and certain thiols to provide amides, esters and thioesters, respectively. Additional reference is made to: Leo A Paquette, *Encyclopedia of Reagents for Organic Synthesis, Vol. 2*, John Wiley and Sons, New York, 1995 as evidence that active ester is a term well-established in field of organic chemistry.

ai.) As used herein, the term "heterocyclic ring" refers to any cyclic molecular structure comprising atoms of at least two different elements in the ring or rings. Additional reference is made to: *Oxford Dictionary of Biochemistry and Molecular Biology*, Oxford University Press, Oxford, 1997 as evidence that heterocyclic ring is a term well-established in field of organic chemistry.

aj.) As used herein, the term "leaving group" refers to any atom or group, charged or uncharged, that departs during a substitution or displacement reaction from what is regarded as the residual or main part of the substrate of the reaction. Additional reference is made to: *Oxford Dictionary of Biochemistry and Molecular Biology*, Oxford University Press, Oxford, 1997 as evidence that leaving group is a term well-established in field of organic chemistry.

ak.) As used herein, the term "protecting group" refers to a chemical group that is reacted with, and bound to, a functional group in a molecule to prevent the functional group from participating in subsequent reactions of the molecule but which group can subsequently be removed to thereby regenerate the unprotected functional group. Additional reference is made to: *Oxford Dictionary of Biochemistry and Molecular Biology*, Oxford University Press, Oxford, 1997 as evidence that protecting group is a term well-established in field of organic chemistry.

Description of Various Embodiments of the Invention:

It is to be understood that the discussion set forth below in this "General" section can pertain to some, or to all, of the various embodiments of the invention described herein.

I. General

The Labeling Reagent:

As discussed previously, a labeling reagent generally comprises a reporter moiety, a balance moiety (or linker moiety) and a reactive group (FIG. 1a). Some novel labeling reagents disclosed herein can be represented by the general formula I';

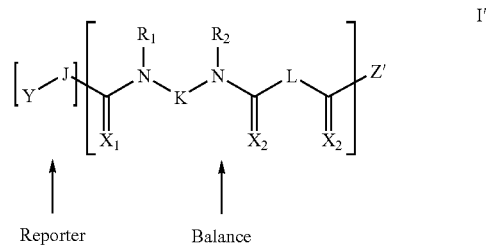

including a salt form thereof and/or a hydrate form thereof, wherein Z' represents the reactive group, or the leaving group of the reactive group, and wherein the atoms or groups $X_1$, $X_2$, $R_1$, $R_2$, Y, J, K and L are described in more detail below. For the compound represented by formula I', the reporter portion and the balance portion of the molecule are indicated. The formulas for other isobaric labeling reagents can be found in FIG. 1d.

The Reactive Group:

The reactive group (sometimes represented by use of the shorthand "RG") of the labeling reagent or reagents used in the method, mixture, kit and/or composition embodiments can be either any electrophilic or a nucleophilic group that is capable of reacting with one or more functional groups of one or more reactive analytes of a sample. It is to be understood that in some embodiments, the reactive group may be considered to include an atom or group associated with the linker (balance). For example, if the reactive group is an active ester or acid halide group, the carbonyl group of the active ester or acid halide may, in some embodiments, also be considered to be associated with the linker for purposes of balancing the mass of the reporter moiety within a set of isomeric and/or isobaric labeling reagents where the carbonyl carbon is present in both the labeling reagent and in the labeled analyte. Consequently, in some embodiments, the reactive group can be understood to merely represent the leaving group of a reactive group.

It is also to be understood that when the reactive group is represented by some of the specific moieties discussed below, the analyte may be linked to the linker (balance) through one or more additional atoms or groups that may, or may not, be considered to be part of the linker (balance).

The reactive group can be preexisting or it can be prepared in-situ. In-situ preparation of the reactive group can proceed in the absence of the reactive analyte or it can proceed in the presence of the reactive analyte. For example, a carboxylic acid group can be modified in-situ with water-soluble carbodiimide (e.g. 1-(3-dimethylaminopropyl)-3-ethylcarbodiimide hydrochloride; EDC) to thereby prepare an electrophilic group that can be reacted with a nucleophile such as an alkyl or aryl amine group of the analyte. In some embodiments, activation of the carboxylic acid group of a labeling reagent with EDC can be performed in the presence of an amine (nucleophile) containing analyte. In some embodiments, the amine (nucleophile) containing analyte can also be added after the initial reaction with EDC is performed. In other embodiments, the reactive group can be generated in-situ by the in-situ removal of a protecting group. Consequently, any existing or newly created reagent or reagents that can effect the derivatization of analytes by the reaction of nucleophiles and/or electrophiles are contemplated by the method, mixture, kit and/or composition embodiments of this invention.

Where the reactive group of the labeling reagent is an electrophile, it can react with a suitable nucleophilic group of the analyte or analytes. Where the reactive group of the labeling reagent is a nucleophile, it can react with a suitable electrophilic group of the analyte or analytes. Numerous pairs of suitable nucleophilic groups and electrophilic groups are known and often used in the chemical and biochemical arts. Non-limiting examples of reagents comprising suitable nucleophilic or electrophilic groups that can be coupled to analytes (e.g. such as proteins, peptides, nucleic acids, carbohydrates, lipids, steroids or other small molecules having a mass of less that 1500 daltons) to effect their derivatization, are described in the Pierce Life Science & Analytical Research Products Catalog & Handbook (a Perstorp Biotec Company), Rockford, Ill. 61105, USA. Other suitable reagents are well known in the art and are commercially available from numerous other vendors such as Sigma-Aldrich.

Figure 8:
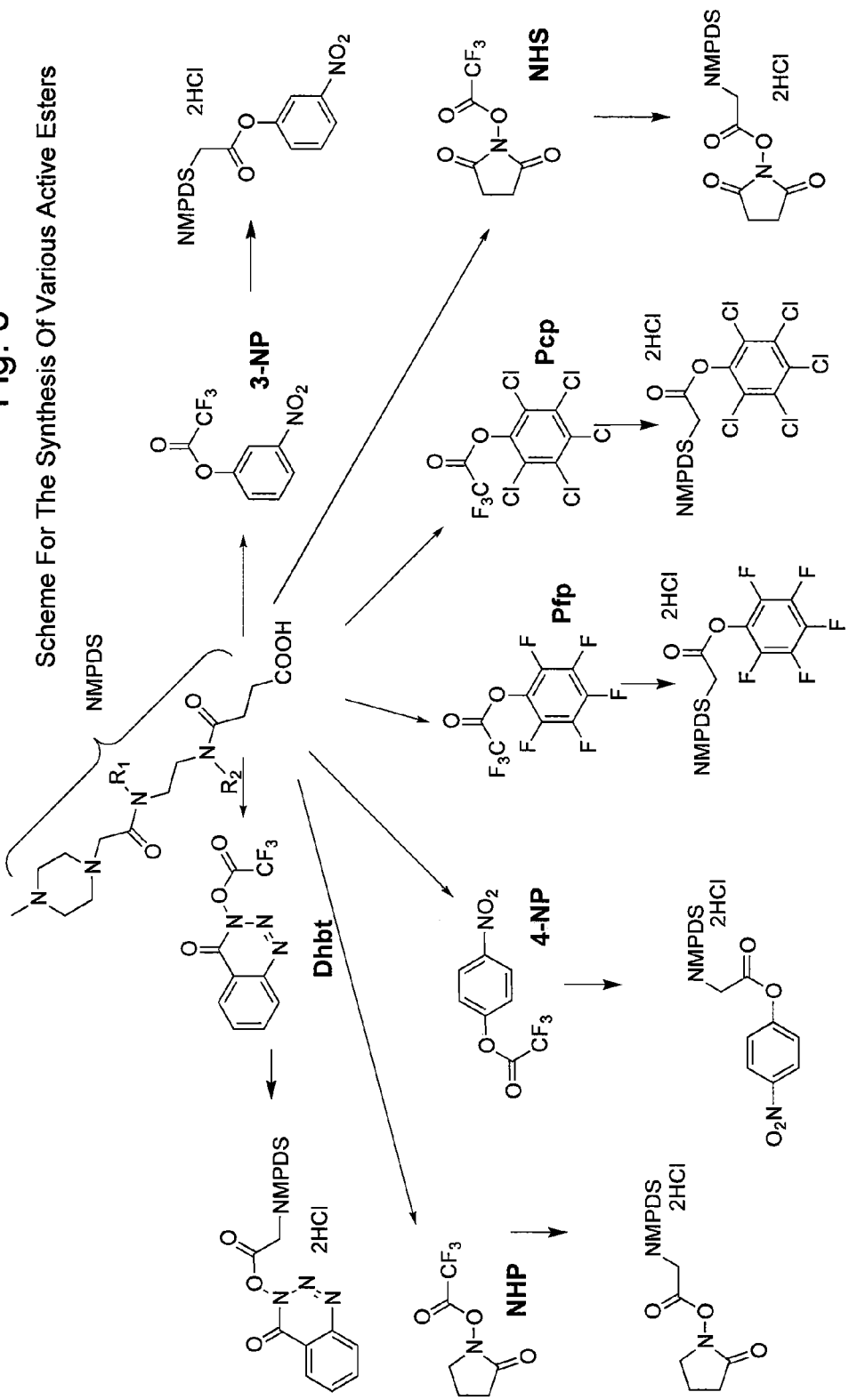
FIG. 8 is an illustration of a scheme for the synthesis of various active esters.

The reactive group of a labeling reagent can be an amine reactive group. For example, the amine reactive group can be an active ester. Active esters are well known in peptide synthesis and refer to certain esters that can be easily reacted with the N-α amine of an amino acid under conditions commonly used in peptide synthesis. (See: Leo A Paquette, *Encyclopedia of Reagents for Organic Synthesis*, Vol. 2, John Wiley and Sons, New York, 1995) The amine reactive active ester group can be an N-hydroxysuccinimidyl ester (NHS), a N-hydroxysulfosuccinimidyl ester (NHSS), a pentafluorophenyl ester (Pfp), a 2-nitrophenyl ester, a 3-nitrophenyl ester (3-NP) a 4-nitrophenyl ester (4-NP), a 2,4-dinitrophenylester, a pentafluorophenyl ester (Pfp), a pentachlorophenyl ester (Pcp), 3-hydroxy-1,2,3-benzotriazine-4(3H)-one ester (Dhbt), hydroxypyrrolidinone ester (NHP), a 2,4-dihalophenyl ester (See: FIG. 8 and the discussion below under the heading: "Illustrative Method For The Manufacture Of Labeling Reagents") a 2,2,2-trifluoroethanyl ester or a 1,1,1,3,3,3-hexafluoro-2-propanyl ester. For example, the leaving group of an active ester (referred to herein generally as Z' in some embodiments such that in this case, the variable RG is synonymous with only the leaving group portion of the reactive group) can be represented by formula:

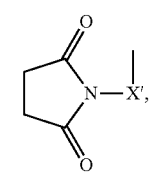

7

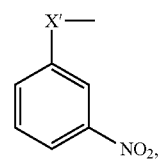

8

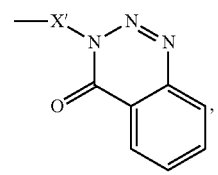

9

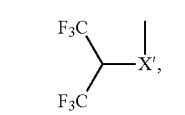

10

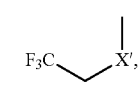

11

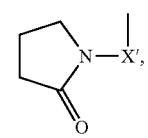

12

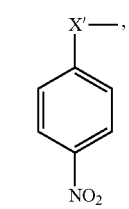

13

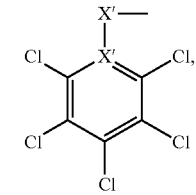

14

15

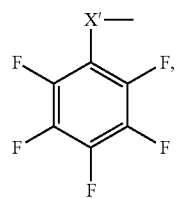

16

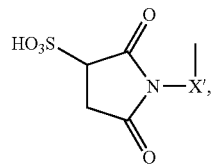

17

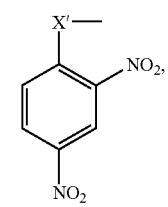

18

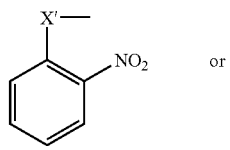 or

19

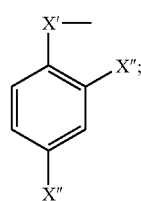

wherein X' is —O— or —S— and each X" is, independently of the other, —F, —Cl, —Br or —I (See: United States Published Patent Application No. US 2005-0148771 A1 for a more detailed description of the synthesis of active esters of representative compounds). All of the foregoing being alcohol or thiol leaving groups of an active ester wherein said alcohol or thiol leaving group can be displaced by the reaction of the N-α-amine of the amino acid with the carbonyl carbon of the active ester group. It should be apparent to the ordinary practitioner that the active ester (e.g. N-hydroxysuccinimidyl ester) of any suitable labelling/tagging reagent described herein could be prepared using well-known procedures in combination with the disclosure provided herein (Also see for example: Greg T. Hermanson (1996). "The Chemistry of Reactive Groups" in "Bioconjugate Techniques" Chapter 2 pages 137-165, Academic Press, (New York); also see: Innovation And Perspectives In Solid Phase Synthesis, Editor: Roger Epton, SPCC (UK) Ltd, Birmingham, 1990).

In some embodiments, the reactive group of the labelling reagent can be a mixed anhydride since mixed anhydrides are known to efficiently react with amine groups to thereby produce amide bonds. Mixed anhydrides are well known and can be prepared using methods often applied in the fields of organic and/or peptide chemistry.

In some embodiments, the reactive group of the labelling reagent can be an acid halide group, such as an acid fluoride group (See: Carpino et al., *J. Am. Chem. Soc.*, 112: 9651 (1990)) or acid chloride group.

In some embodiments, the reactive group of a labeling reagent can be a thiol reactive group. For example, the thiol reactive group can be a malemide, an alkyl halide, an aryl halide of an α-halo-acyl, an α-halo thione or an α-halo imine. By halide or halo we mean atoms of fluorine, chlorine, bromine or iodine. Said thiol reactive groups are well known and can be prepared using methods often applied in the field of peptide chemistry.

In some embodiments, the reactive group of a labeling reagent can be a hydroxyl reactive group. For example, the hydroxyl reactive group can be a trityl-halide or a silyl-halide reactive moiety. The trityl-halide reactive moieties can be substituted (e.g. X'"-methoxytrityl, X'"-dimethoxytrityl, X'"-trimethoxytrityl, etc) or unsubstituted wherein x is the bond that links the reactive group to the linker (i.e. balance). The silyl reactive moieties can be alkyl substituted silyl halides, such as X'"-dimethylsilyl, X'"-ditriethylsilyl, X'"-dipropylsilyl, X'"-diisopropylsilyl, etc.) wherein X'" is the bond that links the reactive group to the linker (i.e. balance). Said reactive groups are well known and can be prepared using methods often applied in the field of nucleic acid chemistry.

In some embodiments, the reactive group of the labeling reagent can be a nucleophile such as an amine group, a hydroxyl group or a thiol group. In some embodiments, the nucleophilic reactive group can be an aminoalkyl group, a hydroxyalkyl group or a thioalkyl group. Said reactive groups are well known and can be prepared using methods often applied in the field of organic chemistry.

The Reporter Moiety:

The reporter moiety (sometimes represented by use of the shorthand "RP") of the labeling reagent or reagents used in embodiments of this invention can be a group that has a unique mass (or mass to charge ratio) that can be determined. Accordingly, each reporter moiety of a set can have a unique gross mass. Different reporter moieties can comprise one or more heavy atom isotopes to achieve their unique gross mass. For example, isotopes of carbon ($^{12}C$, $^{13}C$ and $^{14}C$), nitrogen ($^{14}N$ and $^{15}N$), oxygen ($^{16}O$ and $^{18}O$) or hydrogen (hydrogen, deuterium and tritium) exist and can be used in the preparation of a diverse group of reporter moieties. These are not limiting as other light and heavy atom isotopes can also be used in the reporter moieties. Basic starting materials suitable for preparing reporter moieties comprising light and heavy atom isotopes are available from various commercial sources such as Cambridge Isotope Laboratories, Andover, Mass. (See: list or "basic starting materials" at www.isotope.com) and Isotec (a division of Sigma-Aldrich). Cambridge Isotope Laboratories and Isotec will also prepare desired compounds under custom synthesis contracts. Id.

The reporter moiety can either comprise a fixed charge or can be capable of becoming ionized. Because the reporter moiety can either comprise a fixed charge or can be capable of being ionized, the labeling reagent might be isolated or used to label the reactive analyte in a salt (or a mixture of salts) or zwitterionic form. Ionization of the reporter moiety (or reporter ion) facilitates its determination in a mass spectrometer. Accordingly, the presence of the reporter moiety in a labeled analyte can be determined as a fragment ion, sometimes referred to as a signature ion (or reporter ion). When ionized, the reporter ion can comprise one or more net positive or negative charges. Thus, the reporter ion can comprise one or more acidic groups and/or basic groups since such groups can be easily ionized in a mass spectrometer. For example, the reporter moiety can comprise one or more basic nitrogen atoms (positive charge) or one or more ionizable acidic groups such as a carboxylic acid group, sulfonic acid group or phosphoric acid group (negative charge). Non-limiting examples of reporter moieties comprising at least one basic nitrogen include, substituted or unsubstituted, morpholines, piperidines or piperazines containing compounds.

A unique reporter moiety can be associated with a sample of interest thereby labeling one or multiple analytes of that sample with said unique reporter moiety. In this way information about the unique reporter moiety (generally detected as a reporter ion) can be associated with information about one or all of the analytes of the sample. However, the unique reporter moiety need not be physically linked to an analyte when the reporter ion is determined. Rather, the unique gross mass of the reporter ion can, for example, be determined in a second mass analysis of a tandem mass analyzer, after ions of the labeled analyte are fragmented to thereby produce daughter fragment ions and reporter ions. The determined reporter ion can be used to identify the sample from which a determined analyte originated. Further, the amount of the unique reporter ion, either relative to the amount of other reporter ions or relative to the reporter ion associated with a calibration standard (e.g. an analyte labeled with a specific reporter), can be used to determine the relative and/or absolute amount (often expressed as a concentration and/or quantity) of analyte in the sample or samples (such as those used to form a sample mixture). Therefore information, such as the amount of one or more analytes in a particular sample, can be associated with the reporter moiety that is used to label each particular sample. Where the identity of the analyte or analytes is also determined, that information can be correlated with information pertaining to the different reporter ions to thereby facilitate the determination of the identity and amount of each labeled analyte in one or a plurality of samples.

The reporter moiety can comprise a nitrogen atom covalently linked to the methylene carbon of a substituted or unsubstituted N-alkylated acetic acid moiety wherein the substituted or unsubstituted methylene group but not the carboxylic acid group is part of the reporter. The carboxylic acid group can be used to link the reporter to the linker. The nitrogen atom can be alkylated with one, two or three groups. For example the moiety comprising the nitrogen atom can be a substituted secondary amine such as dimethylamine, diethylamine or dipropylamine.

The reporter moiety can be a 5, 6 or 7 membered heterocyclic ring comprising a ring nitrogen atom that is N-alkylated with a substituted or unsubstituted acetic acid moiety to which the analyte is linked through the carbonyl carbon of the N-alkyl acetic acid moiety wherein the substituted or unsubstituted methylene group but not the carboxylic acid group is part of the reporter. The heterocyclic ring can be aromatic or non-aromatic. Thus, the reporter moiety can be represented by formula Y-J- wherein the group Y can represent the 5, 6 or 7 membered heterocyclic ring and the group J can represent the substituted or unsubstituted methylene group of the acetic acid moiety. The heterocyclic ring can be substituted or unsubstituted. For example, substituents of the heterocyclic moiety can include alkyl, alkoxy and/or aryl groups. The substituents can comprise protected or unprotected groups, such as amine, hydroxyl or thiol groups, suitable for linking the analyte to a support. The heterocyclic ring can comprise additional heteroatoms such as one or more silicon, nitrogen, oxygen and/or sulfur atoms.

The reporter moiety can be selected so that it does not substantially sub-fragment under conditions typical for the analysis of the analyte. For the avoidance of any doubt, this is an optional, not a required, feature. The reporter can be chosen so that it does not substantially sub-fragment under conditions of dissociative energy applied to cause fragmentation of the labeled analyte in a mass spectrometer. By "does not substantially sub-fragment" we mean that fragments of the reporter are difficult or impossible to detect above background noise when applied to the successful analysis of the analyte of interest.

In some embodiments, the gross mass of a reporter ion can be intentionally selected to be different as compared with the mass of the analyte sought to be determined or the mass of any of the expected fragments of the analyte. For example, where proteins or peptides are the analytes, the gross mass of the reporter ion can be chosen to be different as compared with any naturally occurring amino acid or peptide, or expected fragment ions thereof. This can facilitate analyte determination since, depending on the analyte, the lack of any possible components of the sample having the same coincident mass can add confidence to the result of any analysis. Examples of mass ranges where little background can be expected for peptides can be found in Table 1.

TABLE 1

Possible "Quiet Zones" For Selection Of Label Fragment Ion m/z Associated With Peptide Analysis
M/z start-end

| |
| --- |
| 10-14 |
| 19-22 |
| 24-26 |
| 31-38 |
| 40-40 |
| 46-50 |
| 52-52 |
| 58-58 |
| 61-69 |
| 71-71 |
| 74-83 |
| 89-97 |
| 103-109 |
| 113-119 |
| 121-125 |
| 128-128 |
| 131-135 |
| 137-147 |
| 149-154 |
| 156-156 |
| 160-174 |
| 177-182 |
| 184-184 |
| 188-189 |
| 191-191 |
| 202-207 |
| 210-210 |
| 216-222 |
| 224-226 |

The reporter moiety can be non-polymeric. The reporter moiety can be selected to produce a signature ion of m/z less than 250 atomic mass units (amu). The reporter moiety can be selected to produce a signature ion of m/z less than 200 amu. The reporter moiety can be selected to produce a signature ion of m/z less than 150 amu. Such a small molecule can be easily determined in the second mass analysis, free from other components of the sample having the same coincident mass in the first mass analysis. In this context, the second mass analysis can be performed, typically in a tandem mass spectrometer (or, for example by post source decay in a single stage instrument), on selected ions that are determined in the first mass analysis. Because ions of a particular mass to charge ratio can be specifically selected out of the first mass analysis for possible fragmentation and further mass analysis, the non-selected ions from the first mass analysis are not carried forward to the second mass analysis and therefore do not contaminate the spectrum of the second mass analysis. Furthermore, the sensitivity of a mass spectrometer and the linearity of the detector (for purposes of quantification) can be quite robust in this low mass range. Additionally, the present state of mass spectrometer technology can allow for baseline mass resolution of less than one Dalton in this mass range.

The Balance (or Linker) Moiety:

The balance (or linker) moiety (sometimes referred to by use of the shorthand "LK") of the labeling reagent or reagents that can be used with embodiments of this invention to link the reporter moiety to the analyte or the reporter moiety to the reactive group depending on whether or not a reaction with the analyte has occurred. The linker can be selected to produce a neutral species (i.e. undergo neutral loss in a mass spectrometer) wherein both the bond that links the linker to the reporter moiety (the RL bond) and the bond that links the linker to the analyte (the LA bond) fragment in a mass spectrometer. The linker can be designed to sub-fragment when subjected to dissociative energy levels, including sub-fragmentation to thereby produce only neutral fragments of the linker. The linker can be designed to produce one or more detectable fragments.

The linker moiety can comprise one or more heavy atom isotopes such that its mass compensates for the difference in gross mass between the reporter moieties for each labeled analyte of a mixture or for the labeling reagents of set and/or kit. Moreover, the aggregate gross mass (i.e. the gross mass taken as a whole) of the reporter/linker combination (i.e. the reporter/linker moiety) can be the same for each labeled analyte of a mixture or for the labeling reagents of set and/or kit. More specifically, the linker moiety can compensate for the difference in gross mass between reporter moieties of labeled analytes from different samples wherein the unique gross mass of the reporter moiety correlates with the sample from which the labeled analyte originated and the aggregate gross mass of the reporter/linker combination is the same for each labeled analyte of a sample mixture regardless of the sample from which it originated. In this way, the gross mass of identical analytes in two or more different samples can have the same gross mass when labeled and then mixed to produce a sample mixture.

Figure 2A:
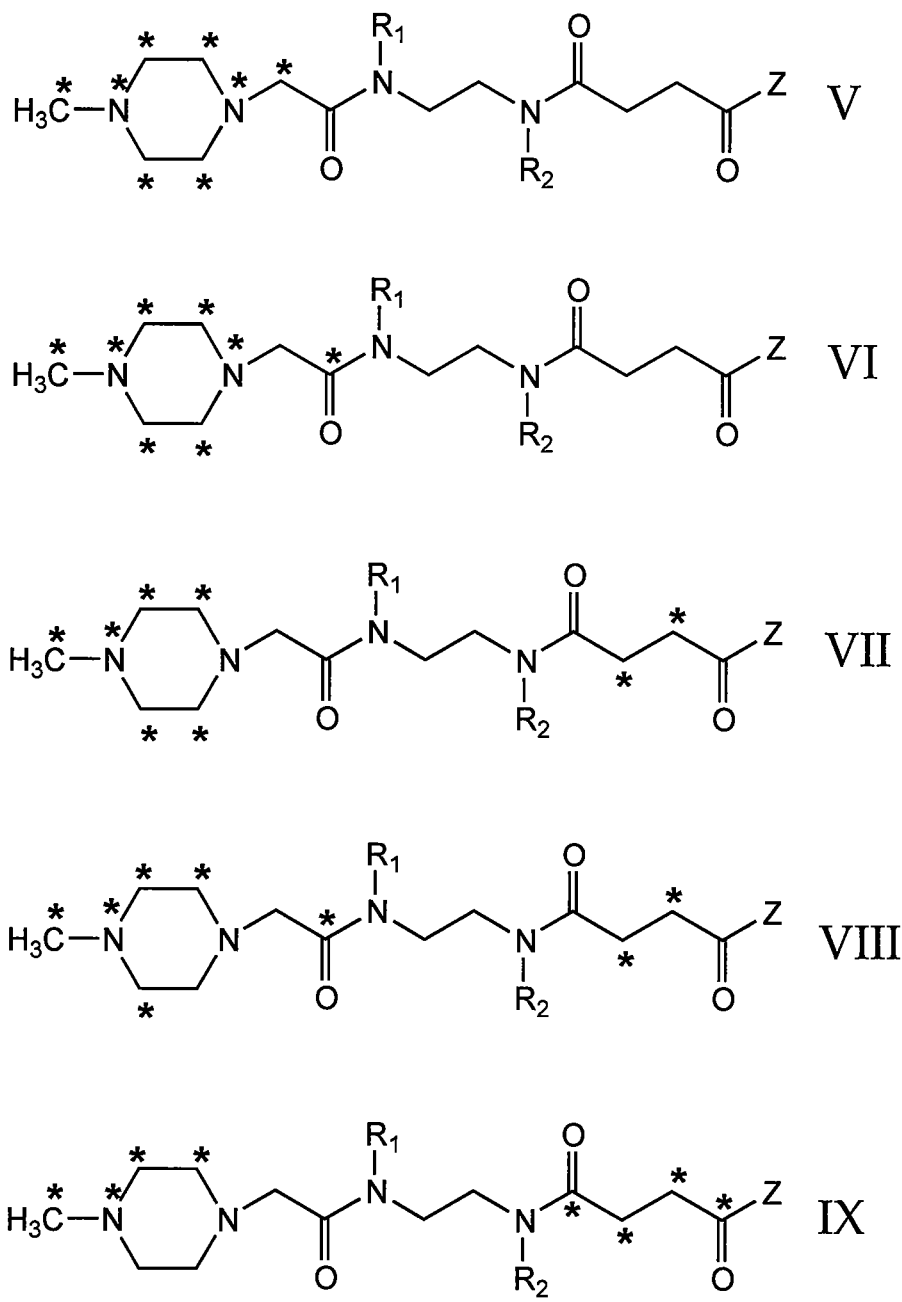
FIG. 2a is an illustration of various isobaric compounds that, when considered with the compounds illustrated in FIG. 2b, can form a 9-plex set.
Figure 2C:
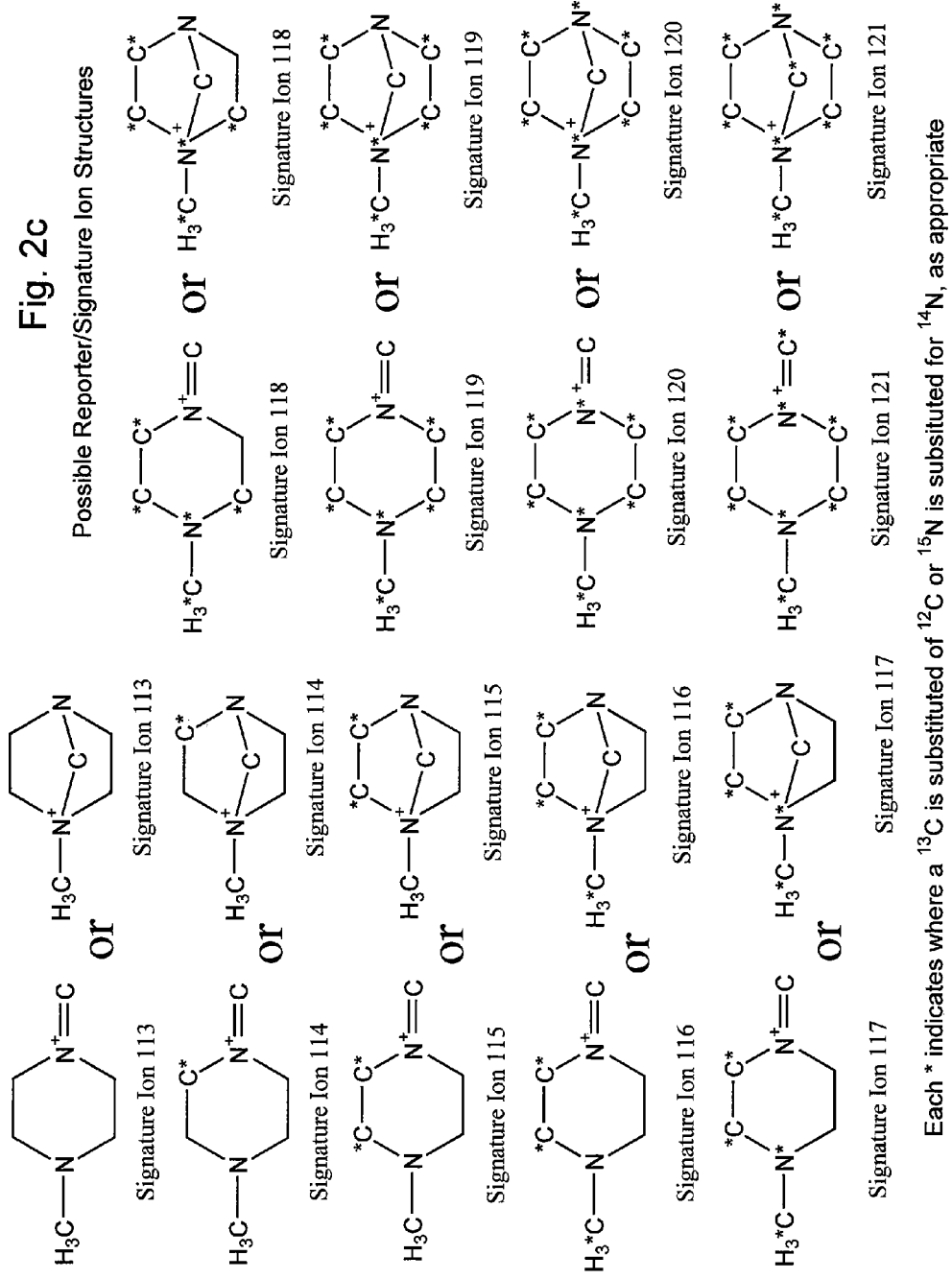
FIG. 2c is an illustration of various possible structures for the reporter ions (i.e. signature ions) that can be generated from the isobaric compounds illustrated in FIGS. 2a, 2b, 3a and 3b.

For example, the labeled analytes, or the labeling reagents of a set and/or kit for labeling the analytes, can be isomers and/or isobars. Thus, if ions of a particular mass to charge ratio (taken from the sample mixture) are selected (i.e. selected ions) in a mass spectrometer from an initial mass analysis of the sample mixture, identical analytes from the different samples that make up the sample mixture can be represented in the selected ions in proportion to their respective concentration and/or quantity in the sample mixture. Accordingly, the linker not only links the reporter to the analyte, it also can serve to compensate for the differing masses of the unique reporter moieties to thereby harmonize the gross mass of the reporter/linker moiety in the labeled analytes of the various samples (c.f. FIGS. 2a/2b and 3a/3b).

Because the linker can act as a mass balance for the reporter moieties in the labeling reagents greater the number of atoms in the linker, the greater the possible number of different isomeric/isobaric labeling reagents of a set and/or kit. Stated differently, generally the greater the number of atoms that a linker comprises, the greater the number of potential reporter/linker combinations exist since isotopes can be substituted at most any position in the linker to thereby produce isomers and/or isobars of the linker portion wherein the linker portion is used to offset the differing masses of the reporter portion and thereby create a set of unique isomeric and/or isobaric labeling reagents. Such diverse sets of labeling reagents are particularly well suited for multiplex analysis of analytes in the same and/or different samples.

The total number of labeling reagents of a set and/or kit can be two, three, four, five, six, seven, eight, nine, ten, eleven, twelve, thirteen, fourteen, fifteen, sixteen, fifteen, sixteen, seventeen, eighteen, nineteen, twenty or more. The diversity of the labeling reagents of a set or kit is limited only by the number of atoms of the reporter and linker moieties, the heavy atom isotopes available to substitute for the light isotopes and the various synthetic configurations in which the isotopes can be synthetically placed. As suggested above however, numerous isotopically enriched basic starting materials are readily available from manufacturers such as Cambridge Isotope Laboratories and Isotec. Such isotopically enriched basic starting materials can be used in the synthetic processes used to produce sets of isobaric and isomeric labeling reagents or be used to produce the isotopically enriched starting materials that can be used in the synthetic processes used to produce sets of isobaric and isomeric labeling reagents. This topic is discussed in more detail below under the heading: "Illustrative Method For The Manufacture Of Labeling Reagents".

Some examples of the preparation of isobaric labeling reagents suitable for use in a set of labeling reagents are discussed in more detail below. For example, a linker moiety can be represented by formula I#;

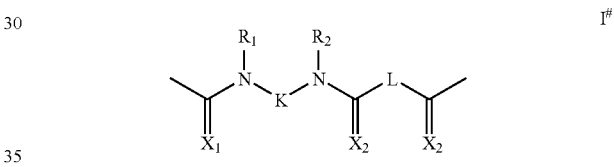

wherein the atoms or groups represented by $X_1$, $X_2$, K, L $R_1$ and $R_2$ are described in more detail below.

The Reporter/Linker Combination (i.e. the Reporter/Linker Moiety):

The labeling reagents can comprise reporter moieties and linker moieties that are linked directly to each other. As described above, the reporter/linker moiety can be identical in gross mass for each member of a set and/or kit of labeling reagents. Moreover, the bond that links the reporter moiety to the linker moiety can be designed to fragment, in at least a portion of the selected ions, when subjected to dissociative energy levels thereby releasing the reporter ion from the linker moiety and/or linker/analyte moiety. Accordingly, the gross mass of the reporter ion (observed as a mass to charge (i.e. m/z) ratio in the mass spectrometer) and its intensity can be observed directly in MS/MS analysis.

The reporter/linker moiety can comprise various combinations of the same or different heavy atom isotopes amongst the various labeling reagents of a set or kit. In the scientific literature this has sometimes been referred to as "coding", "isotope coding" or simply as "encoding". For example, Abersold et al. has disclosed the isotope coded affinity tag (ICAT; see WO00/11208). In one respect, the reagents of Abersold et al. differ from the labeling reagents of this invention in that Abersold does not teach two or more same mass labeling reagents such as isomeric and/or isobaric labeling reagents. Rather, Abersold et al. teach about "light" and "heavy" versions of their labeling reagents.

In some embodiments, the reporter and/or linker moieties can comprise an atom or group that can be used to immobilize the labeling reagent or labeled analyte to a support. Immobilization can be direct or indirect. For example, direct immobilization can occur if an atom or group (e.g. an alkyl amine substituent of the reporter and/or linker) associated with the reporter and/or linker can, in some embodiments, interact directly with a reactive group (e.g. a cleavable linker) of the support to effect mobilization. By comparison, indirect immobilization occurs if, for example, a substituent of the reporter and/or linker (e.g. an alkylamine substituent of the reporter and/or linker) is modified (e.g. is biotinylated) and the modifying group interacts with a reactive group of the support (e.g. avidin or streptavidin) to effect immobilization. Consequently, this invention contemplates embodiments wherein the analytes can be reacted with support bound labeling reagents wherein each support comprises a unique labeling reagent such that different samples are reacted with different supports as well as embodiments where each different sample is reacted with a different labeling reagent and the reaction products are thereafter immobilized to the same or to different supports. In either case, a sample mixture is generally obtained by cleaving the labeled analytes from the support(s) for analysis by mass spectrometry (See: FIG. 5).

Mass Spectrometers/Mass Spectrometry (MS):

The methods of this invention can be practiced using tandem mass spectrometers and other mass spectrometers that have the ability to select and fragment molecular ions. Tandem mass spectrometers (and to a lesser degree single-stage mass spectrometers) have the ability to select and fragment molecular ions according to their mass-to-charge (m/z) ratio, and then record the resulting fragment (daughter) ion spectra. More specifically, daughter fragment ion spectra can be generated by subjecting selected ions to dissociative energy levels (e.g. collision-induced dissociation (CID)). For example, ions corresponding to labeled peptides of a particular m/z ratio can be selected from a first mass analysis, fragmented and reanalyzed in a second mass analysis. Representative instruments that can perform such tandem mass analysis include, but are not limited to, magnetic four-sector, tandem time-of-flight, triple quadrupole, ion-trap, and hybrid quadrupole time-of-flight (Q-TOF) mass spectrometers.

These types of mass spectrometers may be used in conjunction with a variety of ionization sources, including, but not limited to, electrospray ionization (ESI) and matrix-assisted laser desorption ionization (MALDI). Ionization sources can be used to generate charged species for the first mass analysis where the analytes do not already possess a fixed charge. Additional mass spectrometry instruments and fragmentation methods include post-source decay in MALDI-MS instruments and high-energy CID using MALDI-TOF(time of flight)-TOF MS. For a recent review of tandem mass spectrometers please see: R. Aebersold and D. Goodlett, *Mass Spectrometry in Proteomics. Chem. Rev.* 101: 269-295 (2001).

Fragmentation by Dissociative Energy Levels:

It is well accepted that bonds can fragment as a result of the processes occurring in a mass spectrometer. Moreover, bond fragmentation can be induced in a mass spectrometer by subjecting ions to dissociative energy levels. For example, the dissociative energy levels can be produced in a mass spectrometer by collision-induced dissociation (CID, sometimes also referred to as collision activated dissociation or CAD). Those of ordinary skill in the art of mass spectrometry will appreciate that other exemplary techniques for imposing dissociative energy levels that cause fragmentation include, but are not limited to, photo dissociation, electron capture dissociation (ECD), electron transfer dissociation (ETD, See: US Published Patent Application No. 2005-199804 A1 and Syka et al., *Proc. Nat'l. Acad. Sci. USA.*, 101(26): 9528-9533 (2004)), and surface induced dissociation (SID). For purposes of interpreting this specification, dissociative energy levels can also be considered to include any type of gas-phase chemical reactions that result in fragmentation in a mass spectrometer.

The process of fragmenting bonds by collision-induced dissociation involves increasing the kinetic energy state of selected ions, through collision with an inert gas, to a point where bond fragmentation occurs. For example, kinetic energy can be transferred by collision with an inert gas (such as nitrogen, helium or argon) in a collision cell. The amount of kinetic energy that can be transferred to the ions is proportional to the number of gas molecules that are allowed to enter the collision cell. When more gas molecules are present, a greater amount of kinetic energy can be transferred to the selected ions, and less kinetic energy is transferred when there are fewer gas molecules present.

It is therefore clear that the dissociative energy level in a mass spectrometer can be controlled. It is also well accepted that certain bonds are more labile than other bonds. The lability of the bonds in an analyte or the reporter/linker moiety depends upon the nature of the analyte or the reporter/linker moiety. Accordingly, the dissociative energy levels can be adjusted so that the analytes and/or the labels (e.g. the reporter/linker combinations) can be fragmented in a manner that is determinable. One of skill in the art will appreciate how to make such routine adjustments to the components of a mass spectrometer to thereby achieve the appropriate level of dissociative energy to thereby fragment at least a portion of ions of labeled analytes into ionized reporter moieties and daughter fragment ions.

For example, dissociative energy can be applied to ions that are selected/isolated from the first mass analysis. In a tandem mass spectrometer, the extracted ions can be subjected to dissociative energy levels and then transferred to a second mass analyzer. The selected ions can have a selected mass to charge ratio. The mass to charge ratio can be within a range of mass to charge ratios depending upon the characteristics of the mass spectrometer. When collision induced dissociation is used, the ions can be transferred from the first to the second mass analyzer by passing them through a collision cell where the dissociative energy can be applied to thereby produce fragment ions. For example the ions sent to the second mass analyzer for analysis can include some, or a portion, of the remaining (unfragmented) selected ions, as well as reporter ions (signature ions) and daughter fragment ions of the labeled analyte.

Analyte Determination by Computer Assisted Database Analysis:

In some embodiments, analytes can be determined based upon daughter-ion fragmentation patterns that are analyzed by computer-assisted comparison with the spectra of known or "theoretical" analytes. For example, the daughter fragment ion spectrum of a peptide ion fragmented under conditions of low energy CID can be considered the sum of many discrete fragmentation events. The common nomenclature differentiates daughter fragment ions according to the amide bond that breaks and the peptide fragment that retains charge following bond fission (Reopstorff et al., *Biomed. Mass Spectrom.*, 11: 601 (1988)). Charge-retention on the N-terminal side of the fissile amide bond results in the formation of a b-type ion. If the charge remains on the C-terminal side of the broken amide bond, then the fragment ion is referred to as a y-type ion. In addition to b- and y-type ions, the CID mass spectrum may contain other diagnostic fragment ions (daughter fragment ions). These include ions generated by neutral loss of ammonia (−17 amu) from glutamine, lysine and arginine or the loss of water (−18 amu) from hydroxyl-containing amino acids such as serine and threonine. Certain amino acids have been observed to fragment more readily under conditions of low-energy CID than others. This is particularly apparent for peptides containing proline or aspartic acid residues, and even more so at aspartyl-proline bonds (Mak, M. et al., *Rapid Commun. Mass Spectrom.,* 12: 837-842 (1998)). Accordingly, the peptide bond of a $Z'''$-pro dimer or $Z'''$-asp dimer, wherein $Z'''$ is any natural amino acid, pro is proline and asp is aspartic acid, will tend to be more labile as compared with the peptide bond between all other amino acid dimer combinations.

For peptide and protein samples therefore, low-energy CID spectra contain redundant sequence-specific information in overlapping b- and y-series ions, internal fragment ions from the same peptide, and immonium and other neutral-loss ions. Interpreting such CID spectra to assemble the amino acid sequence of the parent peptide de novo is challenging and time-consuming but can be done. Recent advances in computer assisted de novo methods for sequencing are were described in Huang, Y., Ross, P, Smirnov, I, Martin, S, and Pappin, D. 2003, Proceedings of 6th International Symposium on MS in Health and Life Sciences, Aug. 24-28, 2003, San Francisco Calif. The most significant advances in identifying peptide sequences have been the development of computer algorithms that correlate peptide CID spectra with peptide sequences that already exist in protein and DNA sequence databases. Such approaches are exemplified by programs such as SEQUEST (Eng, J. et al. *J. Am. Soc. Mass Spectrom.,* 5: 976-989 (1994)) and MASCOT (Perkins, D. et al. *Electrophoresis,* 20: 3551-3567 (1999)).

In brief, experimental peptide CID spectra (MS/MS spectra) are matched or correlated with 'theoretical' daughter fragment ion spectra computationally generated from peptide sequences obtained from protein or genome sequence databases. The match or correlation is based upon the similarities between the expected mass and the observed mass of the daughter fragment ions in MS/MS mode. The potential match or correlation is scored according to how well the experimental and 'theoretical' fragment patterns coincide. The constraints on databases searching for a given peptide amino acid sequence are so discriminating that a single peptide CID spectrum can be adequate for identifying any given protein in a whole-genome or expressed sequence tag (EST) database. For other reviews please see: Yates, J. R. Trends, *Genetics,* 16: 5-8 (2000) and Yates, J. R., *Electrophoresis* 19: 893-900 (1998).

Accordingly, daughter fragment ion analysis of MS/MS spectra can be used not only to determine the analyte of a labeled analyte, it can also be used to determine analytes from which the determined analyte originated. For example, identification of a peptide in the MS/MS analysis can be can be used to determine the protein from which the peptide was cleaved as a consequence of an enzymatic digestion of the protein. It is envisioned that such analysis can be applied to other analytes, such as nucleic acids, lipids and/or steroids.

The RL Bond and the LA Bond:

The bond between an atom of the reporter moiety and an atom of the linker moiety is the RL bond. The bond between an atom of the linker moiety and an atom of the analyte is the LA bond. In some embodiments, the RL bond and the LA bond can fragment, in at least a portion of selected ions, when subjected to dissociative energy levels. Therefore, the dissociative energy level can, in some embodiments, be adjusted in a mass spectrometer so that both the RL bond and the LA bond fragment in at least a portion of the selected ions of the labeled analytes.

Fragmentation of the RL bond releases the reporter moiety from the analyte so that the reporter ion can be determined independently from the analyte. Fragmentation of LA bond releases the reporter/linker moiety from the analyte, or the linker from the analyte, depending on whether or not the RL bond has already fragmented. In some embodiments, the RL bond can be more labile than the LA bond. In some embodiments, the LA bond can be more labile than the RL bond. In some embodiments, the RL and LA bonds can be of the same relative lability. Stated briefly, the RL bond is designed to fragment to thereby release the reporter ion but the LA bond may, or may not, fragment in the various embodiments of this invention.

In some embodiments, when the analyte of interest is a protein or peptide, the relative lability of the RL and LA bonds can be adjusted with regard to an amide (peptide) bond. The RL bond, the LA bond or both bonds RL and LA can be more, equal or less labile as compared with a typical amide (peptide) bond. For example, under conditions of dissociative energy, the RL bond and/or the LA bond can be less prone to fragmentation as compared with the peptide bond of a $Z'''$-pro dimer or $Z'''$-asp dimer, wherein $Z'''$ is any natural amino acid, pro is proline and asp is aspartic acid. In some embodiments, the RL bond and the LA bond can fragment with approximately the same level of dissociative energy as a typical amide bond. In some embodiments, the RL and LA bonds can fragment at a greater level of dissociative energy as compared with a typical amide bond.

In some embodiments, the RL bond and the LA bond can exist such that fragmentation of the RL bond results in the fragmentation of the LA bond, and vice versa. In this way, both bonds RL and LA can fragment essentially simultaneously such that no substantial amount of analyte, or daughter fragment ion thereof, comprises a partial label. By "substantial amount of analyte" we mean that less than 25%, and preferably less than 10%, of partially labeled analyte can be determined in the mass spectrometer (e.g. in MS/MS analysis).

Because in some embodiments there can be a clear demarcation between labeled and unlabeled fragments of the analyte in the mass spectra (e.g. in MS/MS analysis), this feature can simplify the identification of the analytes from computer assisted analysis of the daughter fragment ion spectra since no compensation for the remnants of the label need be applied to the mass calculations used to analyze the daughter fragment ions of an analyte. Moreover, because the fragment ions of analytes can, in some embodiments, be either fully labeled or unlabeled (but not partially labeled), there can be little or no scatter in the masses of the daughter fragment ions caused by isotopic distribution across fractured bonds such as would be the case where isotopes were present on each side of a single labile bond of a partially labeled analyte resulting from fragmentation of the labeled analyte caused by the application of dissociative energy levels.

The Labeling of Analytes:

As discussed previously, analytes can be labeled by reacting a functional group of the analyte with the reactive group of the labeling reagent. The functional group on the analyte can be one of an electrophilic group or a nucleophilic group and the functional group of the labeling reagent can be the other of the electrophilic group or the nucleophilic group. The electrophile and nucleophile can react to form a covalent link between the analyte and the labeling reagent.

The labeling reaction can take place in solution. In some embodiments, one of the analyte or the labeling reagent can be support bound. The labeling reaction can sometimes be performed in aqueous conditions. Aqueous conditions can be selected for the labeling of biomolecules such as proteins, peptides and/or nucleic acids. The labeling reaction can sometimes be performed in organic solvent or a mixture of organic solvents. Organic solvents can be selected for analytes that are small molecules. Mixtures of water and organic solvent or organic solvents can be used across a broad range. For example, a solution of water and from about 5 percent to about 95 percent organic solvent or solvents (v/v) can be prepared and used for labeling the analyte. In some embodiments, a solution of water and from about 50 percent to about 95 percent organic solvent or solvents (v/v) can be prepared and used for labeling the analyte. In some embodiments, a solution of water and from about 65 percent to about 80 percent organic solvent or solvents (v/v) can be prepared and used for labeling the analyte. Non-limiting examples of organic solvents include N,N'-dimethylformamide (DMF), acetonitrile (ACN), N-Methyl pyrrolidine (NMP) and alcohols such as methanol, ethanol, propanol and/or butanol. Those of skill in the art will be able to determine appropriate solvent conditions to facilitate analyte labeling depending upon the nature of the labeling reagent and the nature of the analyte using no more than knowledge available in the art and the disclosure provided herein in combination with routine experimentation.

When performing a labeling reaction, the pH can be modulated. The pH can be in the range of 4-10. The pH can be outside this range. Generally, the basicity of non-aqueous reactions can be modulated by the addition of non-nucleophilic organic bases. Non-limiting examples of suitable bases include N-methylmorpholine, triethylamine and N,N-diisopropylethylamine. Alternatively, the pH of water containing solvents can be modulated using biological buffers such as (N-[2-hydroxyethyl]piperazine-N'-[2-ethanesulfonic acid) (HEPES) or 4-morpholineethane-sulfonic acid (MES) or inorganic buffers such as sodium carbonate and/or sodium bicarbonate. Because at least one of the reactive groups can be electrophilic, it can be desirable to select the buffer to not contain any nucleophilic groups. Those of skill in the art will, with the application of ordinary experimentation, be able to identify other buffers that can be used to modulate the pH of a labeling reaction so as to facilitate the labeling of an analyte with a labeling reagent. Accordingly, those of skill in the art will be able to determine appropriate conditions of solvent and pH to thereby facilitate analyte labeling depending upon the nature of the labeling reagent and the nature of the analyte using no more than the disclosure provided herein in combination with routine experimentation.

Sample Processing:

In certain embodiments of this invention, a sample can be processed prior to, as well as after, labeling of the analyte or analytes. Processing can facilitate the labeling of the analyte or analytes. The processing can facilitate the analysis of the sample components. Processing can simplify the handling of the samples. Processing can facilitate two or more of the foregoing.

For example, a sample can be treated with an enzyme or a chemical. The enzyme can be a protease (to degrade proteins and peptides), a nuclease (to degrade nucleic acids) or some other enzyme. The enzyme can be chosen to have a very predictable degradation pattern. Two or more proteases and/or two or more nuclease enzymes may also be used together, or with other enzymes, to thereby degrade sample components.

For example, the proteolytic enzyme trypsin is a serine protease that cleaves peptide bonds between lysine or arginine and an unspecific amino acid to thereby produce peptides that comprise an amine terminus (N-terminus) and lysine or arginine carboxyl terminal amino acid (C-terminus). In this way the peptides from the cleavage of the protein are predictable and their presence and/or quantity, in a sample from a trypsin digest, can be indicative of the presence and/or quantity of the protein of their origin. Moreover, the free amine termini of a peptide can be a good nucleophile that facilitates its labeling. Other exemplary proteolytic enzymes include papain, pepsin, ArgC, LysC, V8 protease, AspN, pronase, chymotrypsin and carboxypeptidase (e.g. carboxypeptidase A, B, C, etc).

For example, a protein (e.g. protein g) might produce three peptides (e.g. peptides B, C and D) when digested with a protease such as trypsin. Accordingly, a sample that has been digested with a proteolytic enzyme, such as trypsin, and that when analyzed is confirmed to contain peptides B, C and D, can be said to have originally comprised the protein g. The quantity of peptides B, C and D will also correlate with the quantity of protein g in the sample that was digested. In this way, any determination of the identity and/or quantify of one or more of peptides B, C and D in a sample (or a fraction thereof), can be used to identify and/or quantify protein g in the original sample (or a fraction thereof).

Because activity of certain enzymes is predictable, the sequence of peptides that are produced from degradation of a protein of known sequence can be predicted. With this information, "theoretical" peptide information can be generated. A determination of the "theoretical" peptide fragments in computer assisted analysis of daughter fragment ions (as described above) from mass spectrometry analysis of an actual sample can therefore be used to determine one or more peptides or proteins in one or more unknown samples (See for example the section above entitled: "Analyte Determination By Computer Assisted Database Analysis").

In some embodiments, sample processing can include treatment of precursors to the analyte or analytes to be labeled. For example, if the analyte or analytes to be labeled are peptides derived from a digested protein and the labeling reagent is, for this example, selected to react with amine groups (e.g. N-α-amine groups and N-ε-amine group of lysine) of the peptide or peptide analytes, the protein (the analyte precursor molecule) of the sample may be processed in a manner that facilitates the labeling reaction. In this example, the protein can be reduced with a reducing agent (e.g. tris[2-carboxyethyl]phosphine (TCEP)) and the thiol groups then blocked by reaction with a blocking reagent (e.g. methyl methanethiosulfonate (MMTS)). In this way the thiol groups of the protein are blocked and therefore do not interfere with the labeling reaction between the amines of the analytes and labeling reagent.

Those of skill in the art will appreciate that treatment of certain other precursor molecules can be performed using readily available reagents and protocols that can be adapted with the aid of routing experimentation. The precise choices or reagents and conditions can be selected depending on the nature of the analyte to be labeled and the labeling reagent.

In some embodiments, sample processing can include the immobilization of the analytes or analyte precursors to a solid support, whether labeled with a labeling reagent or not. Immobilization can include covalent immobilization as well as adsorption and other non-covalent means of immobilization (e.g. electrostatic immobilization). In some embodiments, immobilization can facilitate reducing sample complexity. In some embodiments, immobilization can facilitate analyte labeling. In some embodiments, immobilization can facilitate analyte precursor labeling. In some embodiments, immobilization can facilitate selective labeling of a fraction of sample components comprising a certain property (e.g.

they comprise or lack cysteine moieties). In some embodiments, immobilization can facilitate purification. The immobilization can facilitate two or more of the foregoing.

Separation Including Separation of the Sample Mixture:

In some embodiments, the processing of a sample or sample mixture of labeled analytes can involve separation. One or more separations can be performed on the labeled or unlabeled analytes, labeled or unlabeled analyte precursors, or fractions thereof. One or more separations can be performed on one or more fractions obtained from a solid phase capture or other product of a separations process. Separations can be preformed on two or more of the foregoing.

For example, a sample mixture comprising differentially labeled analytes from different samples can be prepared. By differentially labeled we mean that each of the labels that differs from the others comprises a unique property that can be identified (e.g. each label comprises a unique reporter moiety that produces a unique "signature ion" in MS/MS analysis). In order to analyze the sample mixture, components of the sample mixture can be separated and mass analysis performed on only a fraction of the sample mixture. In this way, the complexity of the analysis can be substantially reduced since separated analytes can be individually analyzed for mass thereby increasing the sensitivity of the analysis process. Of course the analysis can be repeated one or more time on one or more additional fractions of the sample mixture to thereby allow for the analysis of all fractions of the sample mixture.

Separation conditions under which identical analytes that are differentially labeled co-elute at a concentration, or in a quantity, that is in proportion to their abundance in the sample mixture can be used to determine the amount of each labeled analyte in each of the samples that comprise the sample mixture provided that the amount of each sample added to the sample mixture is known. Accordingly, in some embodiments, separation of the sample mixture can simplify the analysis whilst maintaining the correlation between signals determined in the mass analysis (e.g. MS/MS analysis) with the amount of the differently labeled analytes in the sample mixture.

The separation can be performed by chromatography. For example, liquid chromatography/mass spectrometry (LC/MS) can be used to effect sample separation and mass analysis. Moreover, any chromatographic separation process suitable to separate the analytes of interest can be used. For example, the chromatographic separation can be normal phase chromatography, reversed-phase chromatography, ion-exchange chromatography (i.e. anion exchange chromatography or cation exchange chromatography), size exclusion chromatography or affinity chromatography.

The separation can be performed electrophoretically. Non-limiting examples of electrophoretic separations techniques that can be used include, but are not limited to, 1 D electrophoretic separation, 2D electrophoretic separation and/or capillary electrophoretic separation.

An isobaric labeling reagent or a set of reagents can be used to label the analytes of a sample. Isobaric labeling reagents are particularly useful when a separation step is performed because the isobaric labels of a set of labeling reagents are structurally indistinguishable (and can be indistinguishable by gross mass until fragmentation removes the reporter from the analyte). Thus, all analytes of identical composition that are labeled with different isobaric labels can chromatograph in exactly the same manner (i.e. co-elute). Because they are structurally indistinguishable, the eluent from the separation process can comprise an amount of each isobarically labeled analyte that is in proportion to the amount of that labeled analyte in the sample mixture. Furthermore, from the knowledge of how the sample mixture was prepared (portions of samples and other optional components (e.g. calibration standards) added to prepare the sample mixture), it is possible to relate the amount of labeled analyte in the sample mixture back to the amount of that labeled analyte in the sample from which it originated.

The labeling reagents can also be isomeric. Although isomers can sometimes be chromatographically separated, there are circumstances, that are condition dependent, where the separation process can be operated to co-elute all of the identical analytes that are differentially labeled wherein the amount of all of the labeled analytes exist in the eluent in proportion to their concentration and/or quantity in the sample mixture.

Relative and Absolute Quantification of Analytes:

In some embodiments, the relative quantification of differentially labeled identical analytes of a sample mixture is possible. For example, relative quantification of differentially labeled identical analytes is possible by comparison of the relative amounts (e.g. area and/or height of the peak reported) of reporter ion (i.e. signature ion) that are determined in the mass analysis (e.g. in the second mass analysis for a selected, labeled analyte observed in a first mass analysis). Stated differently, where each reporter ion can be correlated with information for a particular sample used to produce a sample mixture, the relative amount of that reporter ion, with respect to other reporter ions observed in the mass analysis, is the relative amount of that analyte in the sample mixture. Where components combined to form the sample mixture are known, the relative amount of the analyte in each sample used to prepare the sample mixture can be back calculated based upon the relative amounts of reporter ion observed for the labeled analyte of selected mass to charge. This process can be repeated for all of the different labeled analytes observed in the first mass analysis. In this way, the relative amount (often expressed in concentration and/or quantity) of each reactive analyte, in each of the different samples used to produce the sample mixture, can be determined.

In other embodiments, absolute quantification of analytes can be determined. For these embodiments, a known amount of one or more differentially labeled analytes (the calibration standard or calibration standards) can be added to the sample mixture. A calibration standard can be an expected analyte that is labeled with an isomeric and/or isobaric label of the set of labels used to label the analytes of the sample mixture provided that the reporter moiety for the calibration standard is unique as compared with any of the samples used to form the sample mixture. Once the relative amount of reporter ion for the calibration standard, or standards, is determined with relation to the relative amounts of the reporter ion or ions for the differentially labeled analytes of the sample mixture, it is possible to calculate the absolute amount (often expressed in concentration and/or quantity) of all of the differentially labeled analytes in the sample mixture with reference to the amount of calibration standard that was added to the sample mixture. In this way, the absolute amount of each differentially labeled analyte (for which there is a calibration standard in the sample from which the analyte originated) can also be determined based upon the knowledge of how the sample mixture was prepared.

Notwithstanding the foregoing, corrections to the intensity of the reporters ion (signature ions) can be made, as appropriate, for any naturally occurring, or artificially created, isotopic abundance within the reporter moieties. There are numerous ways to correct for isotopic abundance of impurities in the signature ions of reporter moieties. An example of such a correction can be found in published copending and co-owned U.S. Pat. No. 7,105,806, entitled: "Method and Apparatus For De-Convoluting A Convoluted Spectrum". Basically, the intensity of up-mass and down mass peaks associated with the isotopic cluster of a single labeling reagent can be determined by deconvolution of the convoluted spectrum of the overlapping isotopic clusters of the labeling reagents using mathematical formulas and calculations. Regardless of how the values are determined, the more care taken to accurately quantify the intensity of each reporter ion (i.e. signature ion), the more accurate will be the relative and absolute quantification of the analytes in the original samples.

Proteomic Analysis:

Embodiments of this invention can be used for complex analysis because samples can be multiplexed, analyzed and reanalyzed in a rapid and repetitive manner using mass analysis techniques. For example, sample mixtures can be analyzed for the amount of one or more analytes in one or more samples. The amount (often expressed in concentration and/or quantity) of the analyte or analytes can be determined for the samples from which the sample mixture was comprised. Because the sample processing and mass analyses can be performed rapidly, these methods can be repeated numerous times so that the amount of many differentially labeled analytes of the sample mixture can be determined with regard to their relative and/or absolute amounts in the sample from which the analyte originated.

One application where such a rapid multiplex analysis is useful is in the area of proteomic analysis. Proteomics can be viewed as an experimental approach to describe the information encoded in genomic sequences in terms of structure, function and regulation of biological processes. This may be achieved by systematic analysis of the total protein component expressed by a cell or tissue. Mass spectrometry, used in combination with the method, mixture, kit and/or composition embodiments of this invention is one possible tool for such global protein analysis.

For example, with a set of nine isobaric labeling reagents, it is possible to obtain nine time points in an experiment to determine up or down regulation of protein expression, for example, based upon response of growing cells to a particular stimulant. It is also possible to perform fewer time points but to incorporate one or more controls. It is also possible to do duplicates or triplicates in the same multiplex experiment. In all cases, up or down regulation of the protein expression, optionally with respect to the one or more optional controls and/or sample repeats, can be determined in a single multiplex experiment. Moreover, because processing of the sample mixture is performed in parallel, the results are directly comparable such that no compensation need be applied to account for slight variations in protocol or experimental conditions. Accordingly, experimental analysis for which these isobaric labeling reagents can be used includes, but is not limited to, time course experiments, biomarker analysis, multiplex proteomic analysis, mudpit experiments, affinity pull-downs, determination of post-translational modifications (PTMs) and multiple control experiments.

II. Compositions

In some embodiments, this invention pertains to compositions represented by formula I;

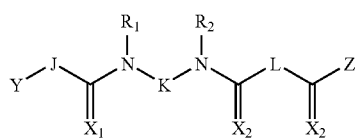

I including a salt form and/or hydrate form thereof; wherein, the group Y-J can be any reporter group. The characteristics of suitable reporter groups have been previously described herein. The characteristics of suitable reporter groups have also been described in US Published Patent Application No. US 2004-0219685-A1 at, inter alia, paragraphs 41-47.

For example, the reporter can comprise a 5, 6 or 7 membered heterocyclic ring that may be substituted or unsubstituted and that may optionally be cleavably linked to a support, wherein the heterocyclic ring comprises at least one ring nitrogen atom that is linked through a covalent bond to the group J. The group J can be a substituted or unsubstituted methylene group represented by formula —CJ'$_2$-, wherein each J' is, independently of the other, hydrogen, deuterium, fluorine, chlorine, bromine, iodine, —R$_3$, —OR$_3$, —SR$_3$, —R$_3$'OR$_3$ or —R$_3$'SR$_3$. The group K can be a group represented by formula —(CK'$_2$)$_n$— or —((CK'$_2$)$_m$—X$_3$—(CK'$_2$)$_m$)$_p$—, wherein n is an integer from 2 to 10, each m is, independently of the other, an integer from 1 to 5, p is an integer from 1 to 4 and each K' is, independently of the other, hydrogen, deuterium, fluorine, chlorine, bromine, iodine, —R$_4$, —OR$_4$, —SR$_4$, —R$_4$'OR$_4$ or —R$_4$'SR$_4$. The group L can be a group represented by formula —(CL'$_2$)$_q$- or —((CL'$_2$)$_m$—X$_3$—(CL'$_2$)$_m$)$_p$-, wherein q is an integer from 1 to 10, each m is, independently of the other, an integer from 1 to 5, p is an integer from 1 to 4 and each L' is, independently of the other, hydrogen, deuterium, fluorine, chlorine, bromine, iodine, —R$_5$, —OR$_5$, —SR$_5$, —R$_5$'OR$_5$ or —R$_5$'SR$_5$; Regarding the groups R$_1$ and R$_2$, either (1) R$_1$ is hydrogen, deuterium or R$_6$ and R$_2$ is hydrogen, deuterium or R$_7$; or (2) R$_1$ and R$_2$ taken together is a group represented by formula —(CR'$_2$)$_q$— or —((CR'$_2$),$_m$—X$_3$—(CR'$_2$)$_m$)$_p$— that forms a ring that bridges the two nitrogen atoms, wherein q is an integer from 1 to 10, each m is, independently of the other, an integer from 1 to 5, p is an integer from 1 to 4 and each R' is, independently of the other, hydrogen, deuterium, fluorine, chlorine, bromine, iodine, —R$_6$, —OR$_6$, —SR$_6$, —R$_6$'OR$_6$ or —R$_6$'SR$_6$. The atom or group X$_1$ can be =O, =S, =NH or =NR$_7$, each X$_2$ can be, independently of the other, =O or =S and each X$_3$ can be, independently of the other, —O— or —S—. The group Z can be —OH, —SH, —O$^-$V$^+$, —S$^-$V$^+$, a reactive group, the leaving group of a reactive group or a covalently linked analyte; wherein, V$^+$ is a positively charged counterion. Each R$_3$, R$_4$, R$_5$, R$_6$ and/or R$_7$, independently of the other, can be alkyl, alkenyl, alkynyl, aryl, heteroaryl or arylalkyl. For example each R$_3$, R$_4$, R$_5$, R$_6$ and/or R$_7$, independently of the other, can be methyl, ethyl, n-propyl, isopropyl, n-butyl, isobutyl, sec-butyl or tert-butyl. Each R$_3$', R$_4$', R$_5$' and/or R$_6$', independently of the other, can be alkylene, alkenylene, alkynylene, arylene or alkylarylene. For example, each R$_3$', R$_4$', R$_5$' and/or R$_6$', independently of the other, can be methylene, ethylene, propylene, cyclopropylene, n-butylene, cyclobutylene, n-pentylene, cyclopentylene, n-hexylene or cyclohexylene.

The compositions can be isotopically enriched (i.e. encoded). The compositions can be isotopically enriched to comprise one or more heavy atom isotopes. The compositions can be isotopically enriched to comprise two or more heavy atom isotopes. The compositions can be isotopically enriched to comprise three or more heavy atom isotopes. The compositions can be isotopically enriched to comprise four or more heavy atom isotopes.

The 5, 6 or 7 membered heterocyclic ring can be any 5, 6 or 7 membered heterocyclic ring that comprises at least one nitrogen atom to which the group J can be covalently linked. For example, it can be a substituted or unsubstituted morpholine, piperidine or piperazine. Possible substituents have been described above in the "Definitions" section wherein the heterocyclic ring can comprise one or more of said substituents. For example, a substituent can be hydrogen, deuterium, methyl, —C(H)₂D, —C(H)D₂, —CD₃ or other alkyl. The substituent can be linked to a heteroatom of the ring. For example, the heterocyclic ring can be N-methylpiperazine. The heterocyclic ring can be aromatic or non-aromatic.

In some embodiments, the reporter moiety can be cleavably linked to a support. Various supports are well known in the art. For example, various supports comprising a trityl moiety are sold commercially or can otherwise be prepared (e.g. Trityl chloride support (Trityl-Cl) or 2-Chlorotrityl chloride support). With reference to FIG. 5, an embodiment of a support bound labeling reagent is illustrated. With reference to FIG. 5, the support can be treated with the analyte to thereby produce the labeled analyte. As illustrated, the support can then be treated with an acid to release the labeled analyte for analysis.

Accordingly, in some embodiments, the 5, 6 or 7 member heterocyclic ring can comprise an atom or group that facilitates the cleavable linkage of it to a suitable support. For example, the group can be an alkylene, alkenylene, alkynylene, arylene or alkylarylene group comprising an amino, hydroxyl or thiol group. The atom can be the secondary nitrogen of a piperazine ring. A discussion of exemplary piperazine compounds and methods for their manufacture can be found in published United States Patent Application No: US 2004-0219685 A1. For example, said support bound N-alkyl piperazine acetic acid compounds can be reacted with a diamine followed by reaction with a diacid to thereby form support bound compounds that can be used as labeling reagents, where isotopic encoding is possible based upon the nature of the reactants.

Figure 6A:
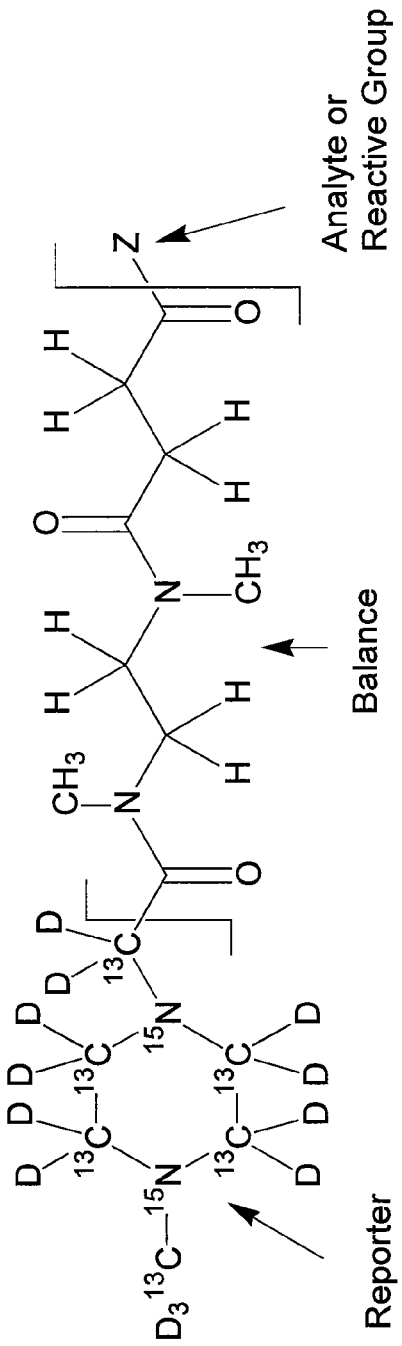
FIG. 6a is an illustration of a labeling reagent or labeled analyte wherein the reporter comprises a plurality of isotopically enriched sites.

Again with reference to formula I, the group Y-J- (whether or not cleavably linked to a support) can form the reporter moiety. The reporter moiety can comprise at least one isotopically enriched site. The reporter moiety can comprise at least two isotopically enriched sites. The reporter moiety can comprise 3, 4, 5, 6, 7, 8, 9, 10, 11, 12, 13, 14, 15, 16 or 17, or more isotopically enriched sites. For example, FIG. 6a illustrates an N-methylpiperazine reporter comprising 21 isotopically enriched sites.

The reporter moiety can either contain a fixed charge or be ionizable in a mass spectrometer. For example, compounds comprising basic groups (e.g. amine groups) are easily protonated to introduce charge and acidic compounds (e.g. carboxylic acid groups) are easily deprotonated to thereby introduce charge (See: Roth, Kenneth et al., "Charge Derivatization of Peptides for Analysis by Mass Spectrometry", *Mass Spectrometry Reviews*, 17: 255-274 (1998)).

Figure 6B:
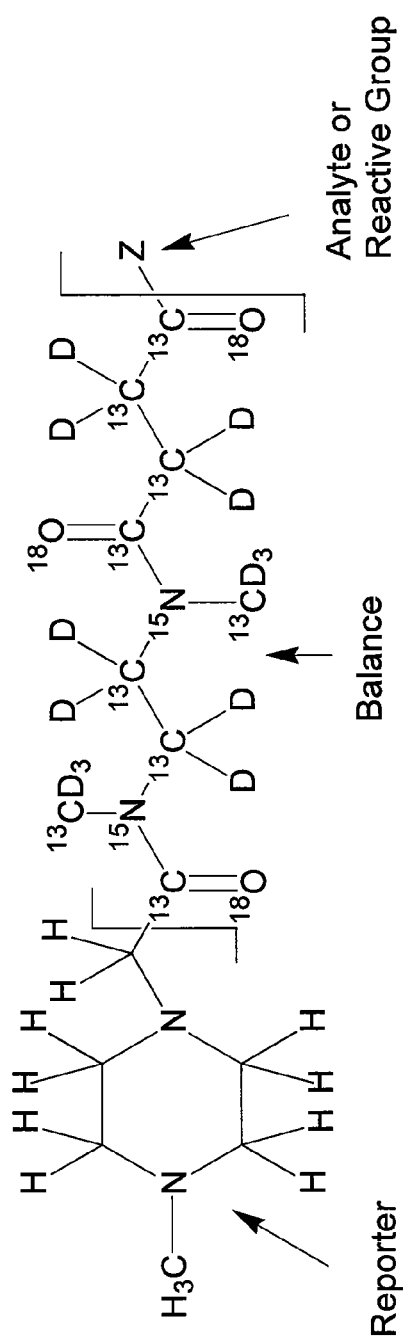
FIG. 6b is an illustration of a labeling reagent or labeled analyte wherein the balance (linker) comprises a plurality of isotopically enriched sites.

The balance (linker) moiety can be formed by the group represented by formula I#;

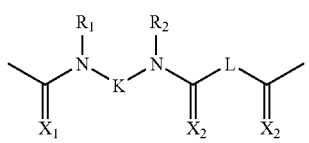

wherein $R_1$, $R_2$, $X_1$, $X_2$, K and L are defined previously. The balance moiety can comprise at least one isotopically enriched site. The balance moiety can comprise at least two isotopically enriched sites. The balance moiety can comprise 3, 4, 5, 6, 7, 8, 9, 10, 11, 12, 13, 14, 15, 16 or 17, or more isotopically enriched sites. For example, FIG. 6b illustrates a balance moiety comprising 28 isotopically enriched sites wherein the total incremental increase in mass can be up to 31 daltons.

In some embodiments, the composition can be represented by formula II;

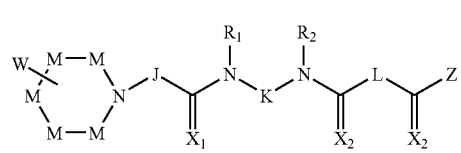

including a salt form and/or hydrate form thereof; wherein W is an atom or group that is substituted for at least one M group of the six membered heterocyclic ring and is located ortho, meta or para to the nitrogen of the six membered ring. The group W can be —N(H)—, —N(R″)—, —N(R‴)—, —P(R″)—, —P(R‴)—, —O— or —S—. If selected as —N(R‴)— or —P(R‴)—, the group can be used to cleavably link the composition to a support. Each remaining group M can be, independently of the other, —CM'₂-, wherein each M' can be, independently of the other, hydrogen, deuterium, fluorine, chlorine, bromine, iodine, —R₈, —OR₈, —SR₈, —R₈'OR₈ or —R₈'SR₈. The groups J, K, L, $X_1$, $X_2$, $R_1$, $R_2$ and Z are as previously defined. Each R″, independently of the other, can be alkyl, alkenyl, alkynyl, aryl, heteroaryl or arylalkyl and each R‴ can be H₂N—R₉'—, H(R₁₀)N—R₉'—, (R₁₀)₂N—R₉'—, HO—R₉'—, HS—R₉'— or a cleavable linker that cleavably links the compound to a support. Each R₈ and/or R₁₀ can be, independently of the other, alkyl, alkenyl, alkynyl, aryl, heteroaryl or arylalkyl and R₉' can be, independently of the other, alkylene, alkenylene, alkynylene, arylene or alkylarylene.

In some embodiments, the composition can be represented by formula III;

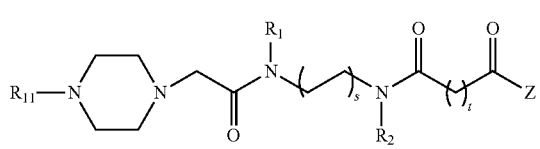

including a salt form and/or hydrate form thereof, wherein s can be an integer from 1 to 5 and t can be an integer from 1 to 10. The groups $R_1$, $R_2$ and Z are as previously defined. The atom or group $R_{11}$ can be hydrogen, deuterium, methyl, —C(H)₂D, —C(H)D₂, —CD₃, other alkyl or —R‴, wherein R‴ is as previously defined. For example, the composition can be selected from one of compounds V-XIII as illustrated in FIGS. 2a and 2b.

Figure 3B:
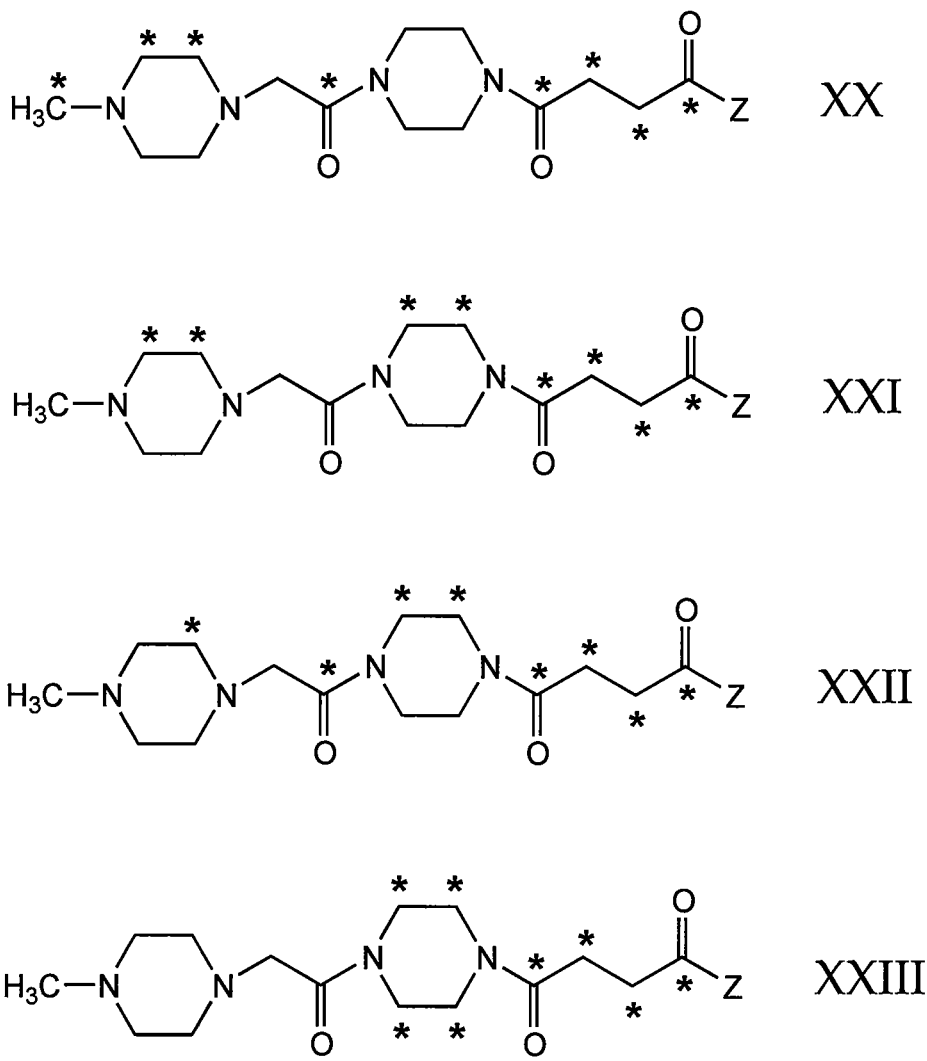
FIG. 3b is an illustration of various isobaric compounds that, when considered with the compounds illustrated in FIG. 3a, can form a 9-plex set, wherein the balance comprises a ring structure.

In some embodiments, the composition can be represented by formula IV;

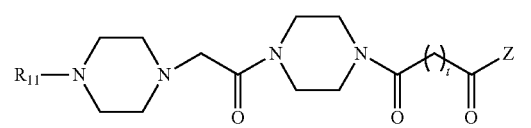

including a salt form and/or hydrate form thereof; wherein, t, $R_{11}$ and Z are as previously defined. For example, the composition can be selected from one of compounds XV-XXIII as illustrated in FIGS. 3a and 3b.

As stated, the compositions can exist in a salt form and/or hydrate form. Whether or not the composition exists as a salt form will typically depend upon the nature and number of substituents as well as the conditions under which it exists and/or was isolated. It is well known that basic groups such as amines can be protonated by treatment with acid to thereby form salts of the amine. For example, piperazine containing labeling reagents can be obtained as a mono-TFA salt, a mono-HCl salt, a bis-TFA salt or a bis-HCl salt. (See for Example, US Patent Application Publication No. US 2005-0148771 A1) It is also well known that acidic groups, such as carboxylic acids, can be deprotonated by treatment with base to form carboxylate salts. Id. For example, —OH of a carboxylic acid or the —SH of a thiocarboxylic acid can be deprotonated to form a —O$^-$V$^+$ and —S$^-$V$^+$, respectively, wherein V$^+$ is the basic counterion (e.g. Li$^+$, Na$^+$, K$^+$, Rb$^+$, Cs$^+$ or NH$_4^+$). If is also well-known that compounds comprising both a basic group such as an amine and an acidic group such as a carboxylic acid can exist in zwitterionic form. All these are considered salt forms and the ionization state of these functional groups of the composition will depend either on the pH of any solution in which they exist, or if isolated, on the pH of the solution from which they were isolated. One of ordinary skill in the art will surely appreciate how to manipulate the charge state and nature of any counterion the salt form of the compositions disclosed herein using no more than routine experimentation and the disclosure provided herein.

Whether or not a composition exists as a hydrate will also depend the conditions under which it exists or was isolated. Hydrates merely comprise one or more complexed water molecules. This invention contemplates any possible hydrate form.

As previously described, the group Z can be a covalently linked analyte. Said analytes can be prepared by reaction of the analyte with a labeling reagent. The analyte can be any analyte. For example, the group Z can be a peptide or protein.

The group Z can be a reactive group as previously described. Thus, in some embodiments, the compound can be a labeling reagent selected from any of compounds I'-XIII' or XV'-XXIII', described below. In some embodiments, the composition can be a labeling reagent such as those illustrated as compounds 80'-87' in FIGS. 25a and 25b.

The group Z can also be —OH, —SH, —O+ or —S$^-$V$^+$. Said groups can be activated to thereby produce a leaving group of a reactive group. Said activated groups are commonly referred to as an activated carboxylic acid group. For example, the —OH group of the carboxylic acid group (COOH) can be activated in-situ with the water soluble carbodiimide EDC as previously described.

The group Z can also be the leaving group of a reactive group such as an activated carboxylic acid or thiocarboxylic acid group (e.g. an active ester). For example the leaving group of the reactive group can be an alcohol or thiol leaving group of formula 7-19 as previously disclosed. The active ester can be an N-hydroxysuccinimidyl ester (i.e. where the leaving is compound 7 and X' is —O—). As previously described, active esters can be reacted with nucleophilic groups, such as an amino group, of the analyte to thereby form the labeled analyte. Accordingly, such compounds are labeling reagents.

The labeling reagents can be isomeric and/or isobaric. Other properties of the labeling reagents have been disclosed. For example, the labeling reagents can be useful for the multiplex analysis of one or more analytes in the same sample, or in two or more different samples.

The labeling reagents can be isotopically enriched (i.e. encoded). The labeling reagents can be isotopically enriched to comprise one or more heavy atom isotopes. The labeling reagents can be isotopically enriched to comprise two or more heavy atom isotopes. The labeling reagents can be isotopically enriched to comprise three or more heavy atom isotopes. The labeling reagents can be isotopically enriched to comprise four or more heavy atom isotopes. The labeling reagents can be isotopically enriched to comprise five or more heavy atom isotopes. The labeling reagents can be isotopically enriched to comprise six or more heavy atom isotopes. The labeling reagents can be isotopically enriched to comprise seven or more heavy atom isotopes. The labeling reagents can be isotopically enriched to comprise eight or more heavy atom isotopes. The labeling reagents can be isotopically enriched to comprise nine or more heavy atom isotopes.

In some embodiments, a composition can be a labeled calibration standard. As described herein, calibration standards can be added to mixtures in known quantities to facilitate absolute quantitative analysis of an analyte of interest. Accordingly, in some embodiments, this invention pertains to an analyte, such as a peptide of interest, which has been labeled with an isomeric and/or isobaric labeling reagent. Thus, the labeled calibration standard can be any analyte labeled with a labeling reagent as described herein. Typically, the labeling reagent is selected from a set of isomeric and/or isobaric labeling reagents so that it comprises a unique reporter as compared with the labeling reagents used to label one or more of the samples of interest.

In some embodiments, a labeled analyte composition can be selected from any of compounds I"-XIII" or XV"-XXIII", described below. In some embodiments, a composition can be a labeled analyte such as those illustrated as 80"-87" in FIGS. 26a-26b.

In some embodiments, the compositions can be fragment ions. For example in some embodiments the composition can be a fragment ion existing in a mass spectrometer following fragmentation of a labeled analyte molecule. For example, the labeled analyte molecules that produce the fragment ion can be selected from compounds 80"-87" as illustrated in FIGS. 26a-26b. Thus, the fragment ion can have a molecular formula of: $^{13}C_6H_{13}^{15}N_2^+$, $^{13}C_4C_2H_{13}^{15}N_2^+$, $^{13}C_3C_3H_{13}^{15}N_2^+$, $^{13}C_3C_3H_{13}^{15}NN^+$, $^{13}C_2C_4H_{13}^{15}NN^+$, $^{13}CC_5H_{13}^{15}NN^+$, $^{13}CC_5H_{13}^{15}N_2^+$ or $C_6H_{13}^{15}N_2^+$. In some embodiments, the molecular formula is selected from $^{13}C_6H_{13}^{15}N_2^+$, $^{13}C_4C_2H_{13}^{15}N_2^+$ and $^{13}C_3C_3H_{13}^{15}N_2^+$.

The fragment ions can be generated by ionizing in a mass spectrometer a fraction of a sample mixture comprising at least two differentially labeled analyte molecules and selecting at least two of the differentially labeled analyte molecules, at a selected m/z value, for fragmentation. The selected differentially labeled analyte molecules can then be fragmented by application of dissociate energy levels wherein at least one of the differentially labeled analyte molecules is a compound of a formula selected from the group consisting of: 80", 81", 82", 83", 84", 85", 86" and 87".

III. Methods for Labeling and Analysis

According to some embodiments of this invention, analytes can be labeled and then determined. The labeled analyte, the analyte itself, one or more fragments of the analyte and/or fragments of the label, can be determined by mass analysis. In some embodiments, methods of this invention can be used for the analysis of different analytes in the same sample as well as for the multiplex analysis of the same and/or different analytes in two or more different samples. The two or more samples can be mixed to form a sample mixture. In multiplex analysis, labeling reagents can be used to determine from which sample of a sample mixture an analyte originated. The absolute and/or relative (with respect to the same analyte in different samples) amount (often expressed in concentration or quantity) of the analyte, in each of two or more of the samples combined to form the sample mixture, can be determined. Moreover, mass analysis of fragments of the analyte (e.g. daughter fragment ions) can be used to identify the analyte and/or the precursor to the analyte; such as where the precursor molecule to the analyte was degraded.

The samples used in the analysis may be any sample comprising analytes that can be labeled with the labeling reagents. For example, the sample can be a crude or processed cell lysate, a body fluid, a tissue extract or a cell extract. The sample can be a fraction from a separations process. Other possible sample types have been described herein.

The analyte in the sample can be any analyte that can be labeled with the labeling reagent. For example, the analyte can be a peptide and/or protein. Other possible analyte types have been disclosed herein.

One distinction of the described approach lies in the fact that analytes from different samples can be differentially labeled (i.e. encoded) with unique labels that are isomeric and/or isobaric (have identical gross mass) and that identify the sample from which the analyte originated. The differentially labeled analytes are not distinguished in MS mode of a mass spectrometer because they all have identical (gross) mass to charge ratios. Often, the labeling reagents of a set are selected so that the labeled analytes are also not distinguishable by separation techniques, such as chromatography or electrophoresis, which might be applied to the mixture before the first mass analysis. However, when subjected to dissociative energy levels, such as through collision induced dissociation (CID), the labels can fragment to yield unique reporter ions that can be resolved by mass (mass to charge ratio) in a mass spectrometer. The relative amount of each unique reporter ion observed in the MS/MS mass spectrum can be correlated with the relative amount of a labeled analyte in the sample mixture and, by implication, the relative amount of that analyte in a sample from which it originated. Thus, the relative intensities of the reporter ions (i.e. signature ions) can be used to determine the relative amount of an analyte or analytes in two or more different samples that were combined to form a sample mixture. From the reporter ion information, absolute amounts (often expressed as concentration and/or quantity) of an analyte or analytes in two or more samples can be derived if calibration standards for each analyte, for which absolute quantification is desired, are incorporated into the sample mixture in a known quantity.

For example, the analyte might be a peptide that resulted from the degradation of a protein using an enzymatic digestion reaction to process the sample. Protein degradation can be accomplished by treatment of the sample with one or more proteolytic enzymes (e.g. trypsin, papain, pepsin, ArgC, LysC, V8 protease, AspN, pronase, chymotrypsin or carboxypeptidase). By determination of the identity and amount of a peptide in a sample mixture and identifying the sample from which it originated, optionally coupled with the determination of other peptides from that sample, the precursor protein to the degraded peptide can be identified and/or quantified with respect to the sample from which it originated. Because this method allows for the multiplex determination of a protein, or proteins, in more than one sample (i.e. from a sample mixture), it is a multiplex method.

Consequently, in some embodiments, this invention pertains to a method comprising reacting two or more samples, each sample comprising one or more reactive analytes, with a different labeling reagent of a set of labeling reagents to thereby produce two or more differentially labeled samples each comprising one or more labeled analytes. The labeling reagents can be selected from a set of isomeric and/or isobaric labeling reagents wherein the different labeling reagents each comprise a reporter moiety of unique mass. The reporter moiety can be any reporter moiety. For example, the reporter moiety can comprise a substituted or unsubstituted piperidine, piperazine or morpholine group.

For example, the different labeling reagents of the set can be represented by formula I';

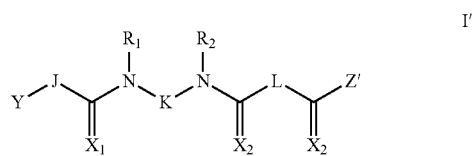

including a salt form or hydrate form thereof, wherein the atoms or groups Y, J, K, L, $R_1$, $R_2$, $X_1$ and $X_2$ are as previously defined and wherein each different labeling reagent of the set has the same gross mass but wherein the group Y-J, which group forms a reporter moiety, of each different labeling reagent is uniquely encoded at one or more isotopically enriched sites such that when the bond between the group J, of the group Y-J, and the remainder of the labeling reagent fragments in a mass spectrometer, a reporter ion of unique mass is produced. The atom or group Z' can be a reactive group or the leaving group of a reactive group.

For example, the reactive group can be a N-hydroxysuccinimidyl ester (NHS), a N-hydroxysulfosuccinimidyl ester (NHSS), a pentafluorophenyl ester (Pfp), a 2-nitrophenyl ester, a 3-nitrophenyl ester (3-NP) a 4-nitrophenyl ester (4-NP), a 2,4-dinitrophenylester, a pentafluorophenyl ester (Pfp), a pentachlorophenyl ester (Pcp), 3-hydroxy-1,2,3-benzotriazine-4(3H)-one ester (Dhbt), hydroxypyrrolidinone ester (NHP), a 2,4-dihalophenyl ester (See: FIG. 8 and the discussion below under the heading: "Illustrative Method For The Manufacture Of Labeling Reagents") a 2,2,2-trifluoroethanyl ester or a 1,1,1,3,3,3-hexafluoro-2-propanyl ester (i.e. the leaving group of the reactive group can be one of compounds 7-19).

Accordingly, the labeled analytes of the sample mixture can be represented by formula

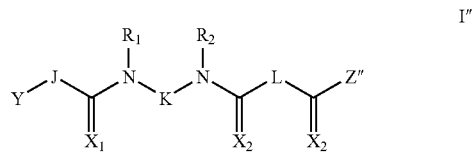

including a salt form and/or hydrate form thereof, wherein the atoms or groups Y, J, K, L, $R_1$, $R_2$, $X_1$ and $X_2$ are as previously defined. For example, the variable Y can be a substituted or unsubstituted morpholine, piperidine or piperazine group. The group Z" can be a covalently linked analyte.

The labeling process can produce two or more differentially labeled samples each comprising one or more labeled analytes. Once the analytes of each sample are labeled with the labeling reagent that is unique to that sample, the two or more differentially labeled samples, or a portion thereof, can be mixed to produce a sample mixture. The sample mixture can optionally comprise one or more calibration standards.

The volume and/or quantity of each sample combined to produce the sample mixture can be recorded. The volume and/or quantity of each sample, relative to the total sample volume and/or quantity of the sample mixture, can be used to determine a ratio that can be used for determining the amount (often expressed in concentration and/or quantity) of an identified analyte in each sample from the analysis of the sample mixture. The sample mixture can therefore comprise a complex mixture wherein relative amounts of the same and/or different analytes can be identified and/or quantified, either by relative quantification of the amounts of analyte in each of the two or more samples or absolutely where a calibration standard is also added to the sample mixture.

The mixture can, for example, be subjected to spectrometry techniques wherein a first mass analysis can be performed on the sample mixture, or fraction thereof, using a first mass analyzer. Ions of a particular mass to charge ratio from the first mass analysis can then be selected. The selected ions can be subjected to dissociative energy levels (e.g. collision-induced dissociation (CID)) to thereby induce fragmentation of the selected ions. By subjecting the selected ions of the labeled analytes to dissociative energy levels bonds RL and LA (See the discussion above under the heading: "The RL bond and the LA bond") can be fragmented in at least a portion of the selected ions. Fragmentation of both bonds RL and LA can cause fragmentation of the reporter/linker moiety as well as cause release the ionized reporter moiety (i.e. the reporter ion or signature ion) from the analyte. Fragmentation of the selected ions by the dissociative energy can also produce daughter fragment ions of the analyte. The ions (remaining selected ions, daughter fragment ions and ionized reporter moieties), or a fraction thereof, can then be directed to a second mass analyzer.

In the second mass analyzer, a second mass analysis can be performed on the selected ions, and the fragments thereof. The second mass analysis can determine the gross mass (or m/z) and relative amount of each unique reporter ion that is present at the selected mass to charge ratio as well as the mass (gross and/or absolute) of some or all of the daughter fragment ions of at least one labeled analyte of the sample mixture. For each analyte present at the selected mass to charge ratio, the daughter fragment ions can be used to identify the analyte and/or analytes present at the selected mass to charge ratio. For example, this analysis can be done as previously described in the section entitled: "Analyte Determination By Computer Assisted Database Analysis".

In some embodiments, certain steps of the process can be repeated one or more times. For example, in some embodiments, ions of a selected mass to charge ratio from the first mass spectrometric analysis, different from any previously selected mass to charge ratio, can be treated to dissociative energy levels to thereby form ionized reporter moieties (i.e. reporter ions) and daughter fragment ions of at least some of the selected ions, as previously described. A second mass analysis of the selected ions, the reporter ions and the daughter fragment ions, or a fraction thereof, can be performed. The gross mass and relative amount of each unique reporter ion in the second mass analysis and the mass (gross or absolute) of the daughter fragment ions can also be determined. In this way, the information can be made available for identifying and/or quantifying one or more additional analytes from the first mass analysis.

In some embodiments, it may be useful to repeat the process one or more times where the sample mixture has been fractionated (e.g. separated by chromatography or electrophoresis). For example, by repeating the process on one or more additional fractions of the sample, it is possible to analyze the entire sample mixture. It is contemplated that in some embodiments, the whole process will be repeated one or more times and within each of these repeats, certain steps can also be repeated one or more times such as described above. In this way, the contents of sample mixture can be interrogated and determined to the fullest possible extent. The entire process can also be repeated on a new set of two or more samples.

Those of ordinary skill in the art of mass spectrometry will appreciate that the first and second mass analysis can be performed in a tandem mass spectrometer. Instruments suitable for performing tandem mass analysis have been previously described herein. Although tandem mass spectrometers are preferred, single-stage mass spectrometers may be used. For example, analyte fragmentation may be induced by cone-voltage fragmentation, followed by mass analysis of the resulting fragments using a single-stage quadrupole or time-of-flight mass spectrometer. In other examples, analytes may be subjected to dissociative energy levels using a laser source and the resulting fragments recorded following post-source decay in time-of-flight or tandem time-of-flight (TOF-TOF) mass spectrometers.

In some embodiments, methods of the invention can further comprise digesting each sample with at least one enzyme to partially, or fully, degrade components of the sample prior to performing the labeling of the analytes of the sample (Also see the above section entitled: "Sample Processing"). For example, the enzyme can be a protease (to degrade proteins and/or peptides) or a nuclease (to degrade nucleic acids). Two or more enzymes may also be used together to thereby further degrade sample components. For example, the enzyme can be a proteolytic enzyme such as trypsin, papain, pepsin, ArgC, LysC, V8 protease, AspN, pronase, chymotrypsin or a carboxypeptidase (e.g. A, B, C, etc).

In some embodiments, methods can further comprise separating the sample mixture prior to performing the first mass analysis (Also see the above section entitled: "Separation Including Separation Of The Sample Mixture"). In this manner the first mass analysis can be performed on only a fraction of the sample mixture. The separation can be performed by any separations method, including by chromatography and/or by electrophoresis. For example, liquid chromatography/mass spectrometry (LC/MS) can be used to effect such a sample separation prior to the mass analysis. Moreover, any chromatographic separation process suitable to separate the analytes of interest can be used. Non-limiting examples of suitable chromatographic and electrophoretic separations processes have been described herein.

In some embodiments, the methods can be practiced with digestion and separation steps. While these steps are optional, they often are performed together, for example, when proteomic analysis is being done to thereby determine the up and down regulation of proteins in cells. In some embodiments, the steps of the methods, with or without the digestion and/or separation steps, can be repeated one or more times to thereby identify and/or quantify one or more other analytes in a sample or one or more analytes in each of the two or more samples (including samples labeled with support bound labeling reagents). Depending of whether or not a calibration standard is present in the sample mixture, the quantification of a particular analyte can be relative to the other labeled analytes, or it can be absolute.

As described previously, it is possible to determine the analyte associated with the selected ions by analysis of the mass (gross or absolute) of the daughter fragment ions. One such method of determination is described in the section entitled: "Analyte Determination By Computer Assisted Database Analysis". Once the analyte has been determined, information regarding the gross mass and relative amount of each unique reporter ion in the second mass analysis and the mass of daughter fragment ions provides the basis to determine other information about the sample mixture.

The relative amount of reporter ion can be determined by peak intensity in the mass spectrum. In some embodiments, the amount of each unique reporter ion can be determined by analysis of the peak height or peak width (or peak area) of the reporter ion (signature ion) obtained using a mass spectrometer. Because each sample can be labeled with a different labeling reagent and each labeling reagent can comprise a unique reporter moiety that produces a unique reporter ion that can be correlated with a particular differentially labeled sample used to formulate the sample mixture, determination of the different reporter ions in the second mass analysis can be used to identify the differentially labeled sample from which the reporter ions of the selected analyte originated. Where multiple reporter ions are found (e.g. according to the multiplex methods of the invention), the relative amount of each unique reporter ion can be determined with respect to the other reporter ions. Because the relative amount of each unique reporter ion determined in the second mass analysis can be correlated with the relative amount of an analyte in the sample mixture, the relative amount (often expressed as concentration and/or quantity) of the analyte in each of the differentially labeled samples combined to form the sample mixture can be determined. Moreover, it is possible to relate the quantification information for an analyte to components of the original differentially labeled samples where an analyte that is determined is a by-product from another compound of interest (e.g. the analyte is a product of a degradation reaction such as where the analyte is a peptide formed by the digestion of a protein).

As discussed above, this analysis can be repeated one or more times on selected ions of a different mass to charge ratio to thereby obtain the relative amount of one or more additional analytes in each sample combined to form the sample mixture. Moreover, as appropriate, a correction of peak intensity associated with each unique reporter ion can be performed for naturally occurring, or artificially created, isotopic abundance, as previously discussed in the section entitled: "Relative and Absolute Quantification of Analytes".

In some embodiments, the analytes can be peptides in a sample or sample mixture. Analysis of the peptides in a sample, or sample mixture, can be used to determine the amount (often expressed as a concentration and/or quantity) of identifiable proteins in the sample or sample mixture wherein proteins in one or more samples can be degraded prior to the first mass analysis. Moreover, the information from different samples can be compared for the purpose of making determinations, such as for the comparison of the effect on the amount of the protein in cells that are incubated with differing concentrations of a substance that may affect cell growth, development, differentiation and/or death. Other, non-limiting examples may include comparison of the expressed protein components of diseased and healthy tissue or cell cultures. This may encompass comparison of expressed protein levels in cells, tissues or biological fluids following infection with an infective agent such as a bacteria or virus or other disease states such as cancer. In other examples, changes in protein concentration over time (timecourse) studies may be undertaken to examine the effect of drug treatment on the expressed protein component of cells or tissues. In still other examples, the information from different samples taken over time may be used to detect and monitor the concentration of specific proteins in tissues, organs or biological fluids as a result of disease (e.g. cancer) or infection. Such experiments may include one or more control samples. In some embodiments, the experiments can be used to determine two or more of the characteristics of interest described above.

In some embodiments, the analyte can be a nucleic acid fragment in a sample or sample mixture. The information on the nucleic acid fragments can be used to determine the amount (often expressed as a concentration and/or quantity) of identifiable nucleic acid molecules in the sample or sample mixture wherein the sample was degraded prior to the first mass analysis. Moreover, the information from the different samples can be compared for the purpose of making determinations of scientific interest.

Where a calibration standard comprising a unique reporter moiety is linked to an analyte, having the selected mass to charge ratio, has been added to the sample mixture in a known amount (often expressed as a concentration and/or quantity), the amount of the unique reporter associated with the calibration standard can be used to determine the absolute amount (often expressed as a concentration and/or quantity) of the analyte in each of the samples combined to form the sample mixture. This is possible because the amount of analyte associated with the unique reporter ion for the calibration standard in the sample mixture is known and the relative amounts of all unique reporter ions can be determined for the labeled analyte associated with the selected ions. Since the relative amount of each unique reporter ion, determined for each of the unique reporters moieties (including the reporter moiety for the calibration standard), is proportional to the amount of the analyte associated with each differentially labeled sample combined to form the sample mixture, the absolute amount (often expressed as a concentration and/or quantity) of the analyte in each of the samples can be determined based upon a ratio calculated with respect to the formulation used to produce the sample mixture. As appropriate, a correction of peak intensity associated with each of the unique reporter ions can be performed for naturally occurring, or artificially created, isotopic abundance. Such an analysis method can be particularly useful for proteomic analysis of multiplex samples of a complex nature, especially where a preliminary separation of the labeled analytes (e.g. liquid chromatography or electrophoretic separation) precedes the first mass analysis.

For example, if a sample mixture comprises 100 fmol/mL of a calibration standard and the relative intensity of the unique reporter ion associated with the calibration standard was 1 while the relative intensity of a first other unique reporter ion associated with a first sample was one-half (1/2 or 0.5) and the relative intensity of a second other unique reporter ion associated with a second sample was 2, the amount of the analyte in the first differentially labeled sample mixed to form the sample mixture (assuming equal amounts of sample 1 and sample 2 are mixed to form the sample mixture) is 50 fmol/mL (0.5×100 fmol/mL) and the amount of the analyte in the second differentially labeled sample mixed to form the sample mixture is 200 fmol/mL (2×100 fmol/mL). Moreover, if, for example, the analyte is a peptide associated with a particular protein, it can be inferred that the amount of the protein in sample 1 is 50 fmol/mL and the amount of the protein in sample 2 is 200 fmol/mL. Thus, the presence of the calibration standard permits absolute quantification of the labeled analytes (and in some cases their precursors) in each differentially labeled sample mixed to form the sample mixture.

As previously discussed, this analysis can be repeated one or more times on selected ions of a different mass to charge ratio to thereby obtain the absolute amount of one or more additional analytes in each sample combined to form the sample mixture. Moreover, as appropriate, a correction of peak intensity associated with each unique reporter ion can be performed for naturally occurring, or artificially created, isotopic abundance, as previously discussed.

In some embodiments, methods described herein can be practiced with support bound labeling reagents, wherein each different labeling reagent of the set is support bound and is linked to the support through a cleavable linker such that each different sample can be reacted with a support carrying a different labeling reagent of the set. Exemplary supports have been discussed above in the section entitled: "Compositions" (Also see FIG. 5 and the Examples section, below). According to the method, the support can be optionally washed to remove components of the sample that do not react with the reactive group of the labeling reagent after the analyte has been permitted to react with the support bound labeling reagent but before the samples are mixed. Once the analyte has been permitted to react with the labeling reagent to thereby form the labeled analyte and the washing step is optionally performed, the labeled analyte(s) can be released from the support by treating the support under conditions whereby the cleavable linker is cleaved. Once cleaved, each of the two or more differentially labeled samples can be optionally collected, each sample comprising one or more labeled analytes wherein the labeled analytes associated with a particular sample are identifiable and/or quantifiable by the unique reporter moiety linked thereto. Whether or not they are collected individually, the products of cleavage can be mixed to form a sample mixture.

In some embodiments, methods described herein can be practiced using a labeling reagent that can be represented by formula II';

II' including a salt form and/or hydrate form thereof; wherein W, M, J, K, L, $R_1$, $R_2$, $X_1$, $X_2$ and Z' are as previously described.

In some embodiments, methods described herein can be practiced using a labeling reagent that can be represented by formula III':

III' including a salt form and/or hydrate form thereof, wherein s, t, $R_1$, $R_2$, $R_{11}$ and Z' are as previously described.

In some embodiments, the method can be practiced using at least one labeling reagent represented by formula:

V'

-continued

VI'

VII'

VIII'

IX'

X'

XI'

XII', or

XIII';

including a salt form and/or hydrate form thereof, wherein, $R_1$, $R_2$, and Z' are as previously described. The symbol * represents where a $^{13}C$ is substituted for a $^{12}C$ or where a $^{15}N$ is substituted for a $^{14}N$, as appropriate.

In some embodiments, the method can be practiced using a labeling reagent that can be represented by formula IV';

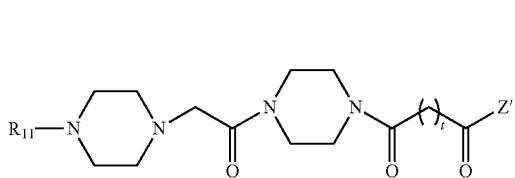

including a salt form and/or hydrate form thereof, wherein t, $R_{11}$ and Z' are as previously described.

In some embodiments, the method can be practiced using at least one labeling reagent that can be represented by formula;

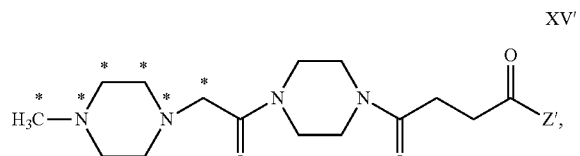

XV'

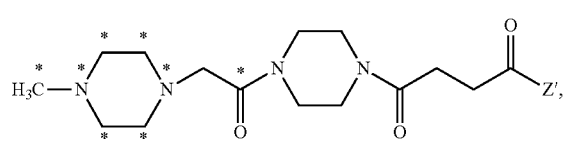

XVI'

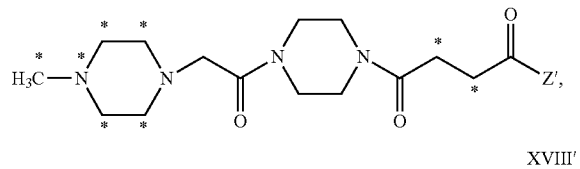

XVII'

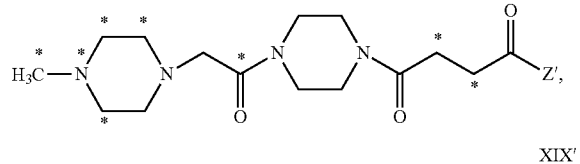

XVIII'

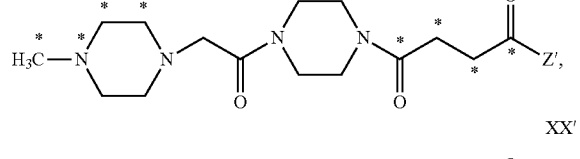

XIX'

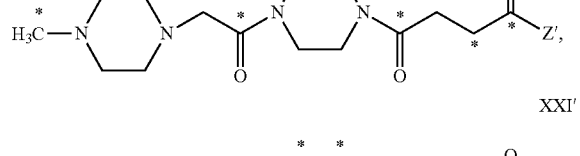

XX'

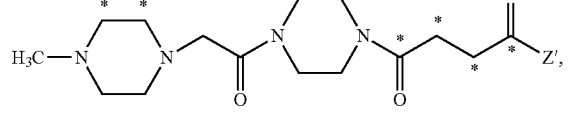

XXI'

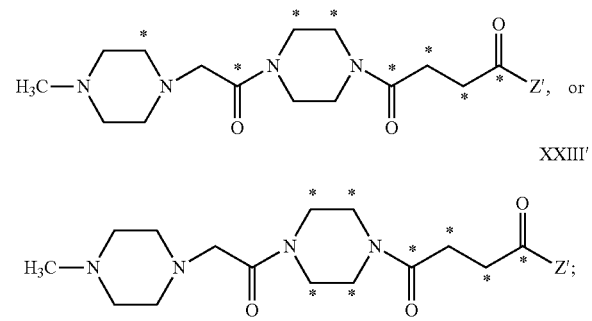

including a salt form and/or hydrate form thereof, wherein, * and Z' are as previously described.

IV. Proteomic Workflows

In some embodiments, the labeling of the analytes of a sample can be performed prior to performing sample processing steps. In some embodiments, the labeling of analytes can be performed after performing one or more sample processing steps. In some embodiments, the labeling of analytes can be performed amongst other sample processing steps. In some embodiments, the labeling of analytes is the last step of sample processing and/or immediately precedes the preparation of a sample mixture.

Using proteomic analysis as a non-limiting example, there are at least several possible workflows that might be used. To aid in understanding of the following discussion a distinction is sometimes made between the precursor protein and the analyte peptide. However, it should be understood that in various embodiments either, or both, proteins and/or peptides could be considered analytes as described herein.

In one type of workflow, the precursor proteins can be digested to peptide analytes that can thereafter be labeled. In another type of workflow, the precursor proteins can be labeled with the labeling reagent and then digested to labeled peptide analytes. In another type of workflow, the precursor proteins can be captured on a solid support, digested and then the support bound peptides can be labeled. Optionally the flow through peptides can also be labeled. In another type of workflow, the precursor proteins can be captured on a solid support, labeled and then the support bound protein can be digested to produce labeled peptides. Optionally the flow through peptides can also be analyzed. Regardless of the workflow, additional sample processing (e.g. separation steps) can be performed on the labeled peptides as desired before MS and MS/MS analysis.

A) Exemplary Workflows Involving Digestion Followed by Labeling

With reference to FIG. 13, for example, there may be a "control" sample and a "test" sample to be analyzed. If, for the example illustrated in FIG. 13, the goal is to analyze peptides (as the analytes) of "control" and "test" sample proteins, the proteins of the samples can, in some embodiments, be optionally reduced, optionally cysteine blocked and digested with an enzyme to thereby produce the analyte peptides that can be labeled for subsequent analysis. The analyte peptides can, in some embodiments, be labeled (tagged) without further sample processing. Regardless of how labeled, the analytes of each different sample can be labeled with using different labeling reagents each comprising a reporter moiety of unique mass (e.g. the labeling reagents of a set of isomeric and/or isobaric labels).

In some embodiments, further sample processing might be desired before labeling and/or after labeling. For example, a separation step might be performed to eliminate certain types of peptides that are not of interest, thereby decreasing the complexity of the sample. The labeled samples can be mixed to obtain a sample mixture. In some embodiments, the labeled analyte peptide can be subject to separation (e.g. high performance liquid chromatography (HPLC)) or other fractionating process before mass spectral analysis.

Figure 14A:
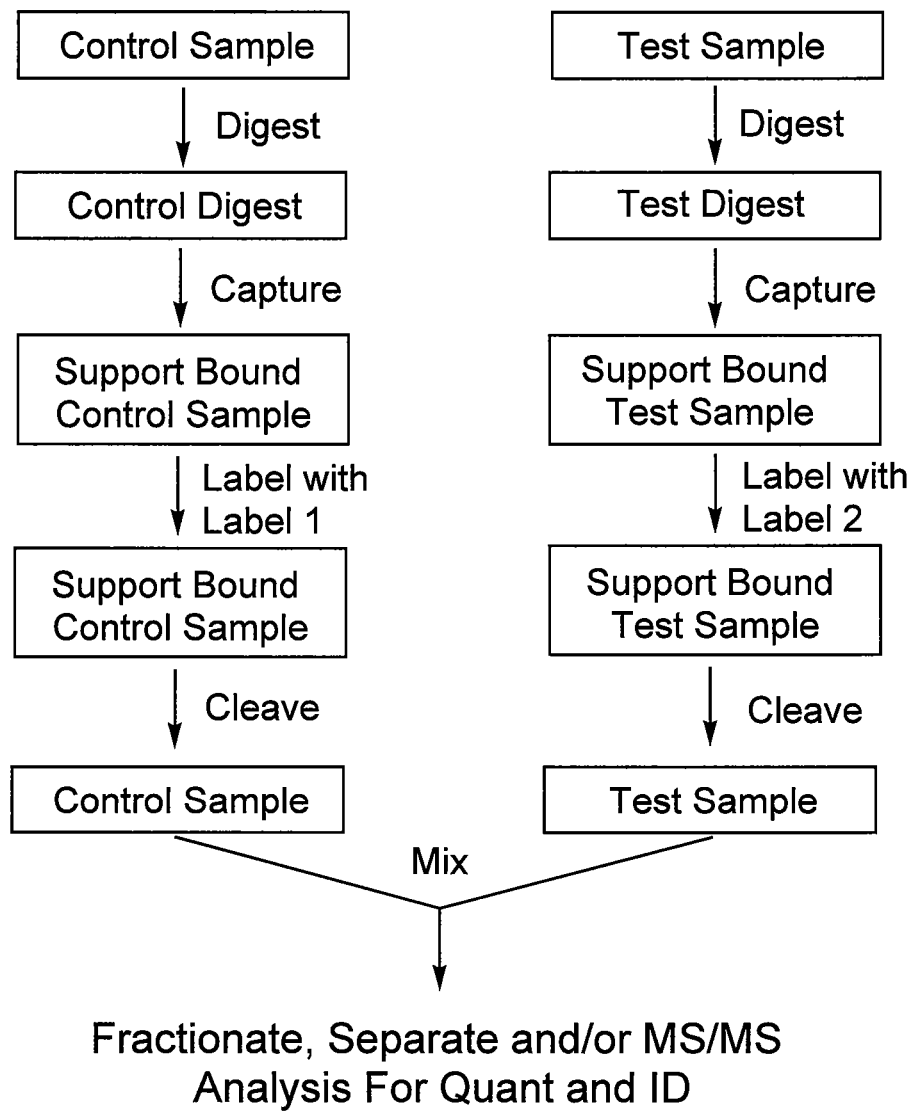
FIG. 14a is an illustration of one possible workflow for processing a test sample and a control sample using a set of isobaric labeling reagents (i.e. Label 1 and Label 2).
Figure 15:
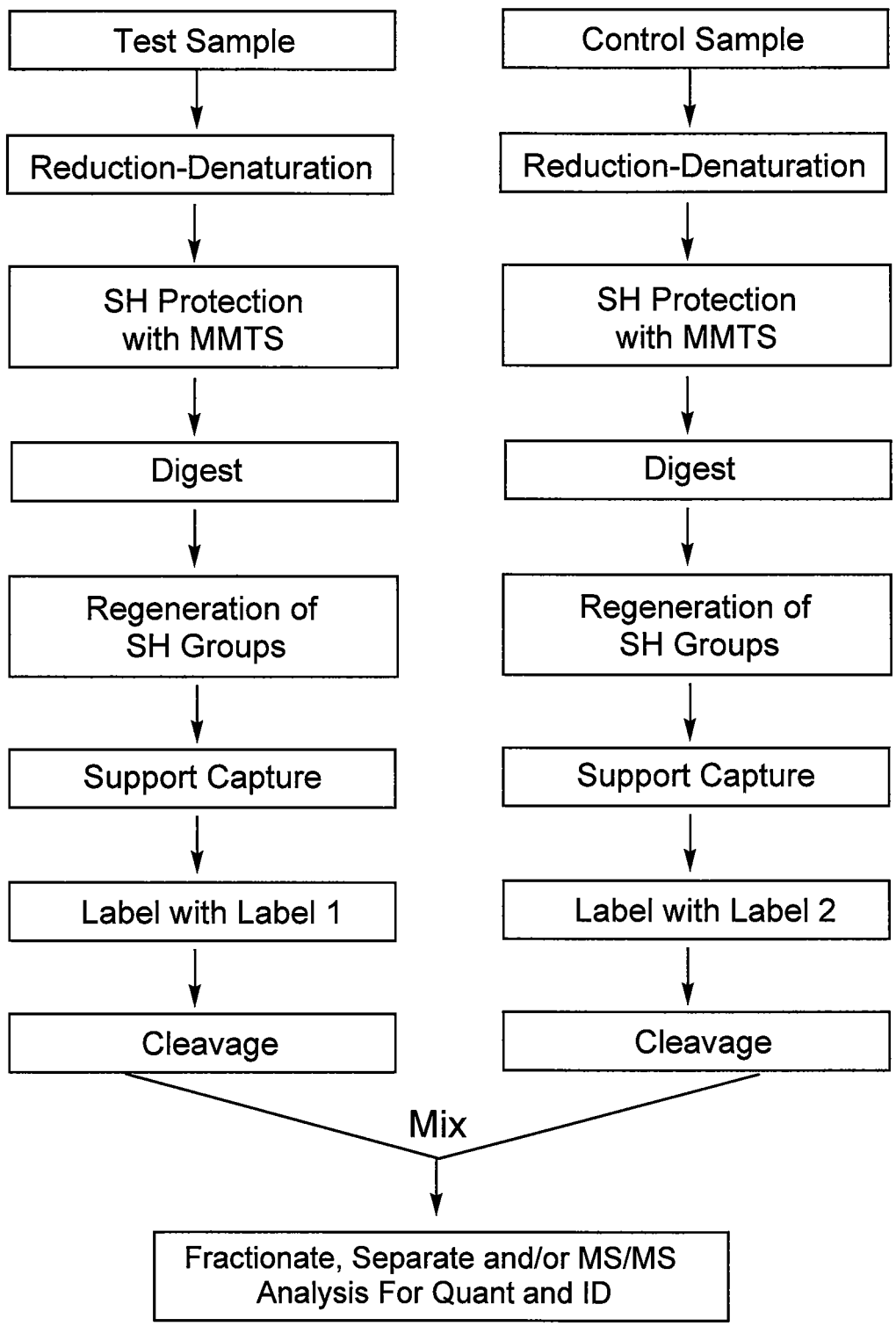
FIG. 15 is an illustration of one possible workflow for processing a test sample and a control sample using a set of isobaric labeling reagents (i.e. Label 1 and Label 2).

Another exemplary workflow is illustrated in FIG. 14a and FIG. 15. FIG. 15 differs from FIG. 14a primarily in that FIG. 15 illustrates optional steps of blocking and regeneration of the thiol groups of cysteine that can be involved with peptide capture. For the avoidance of doubt, although the illustrations in FIGS. 13, 14a, 15 and 16-18 show the application of the workflow to two samples, it is self-evident that additional samples can be processed provided that additional differential labels are available to encode each different sample or sample fraction.

Figure 14B:
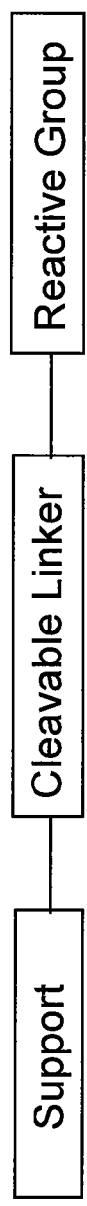
FIG. 14b is an illustration of the elements of a capture support.
Figure 14C:
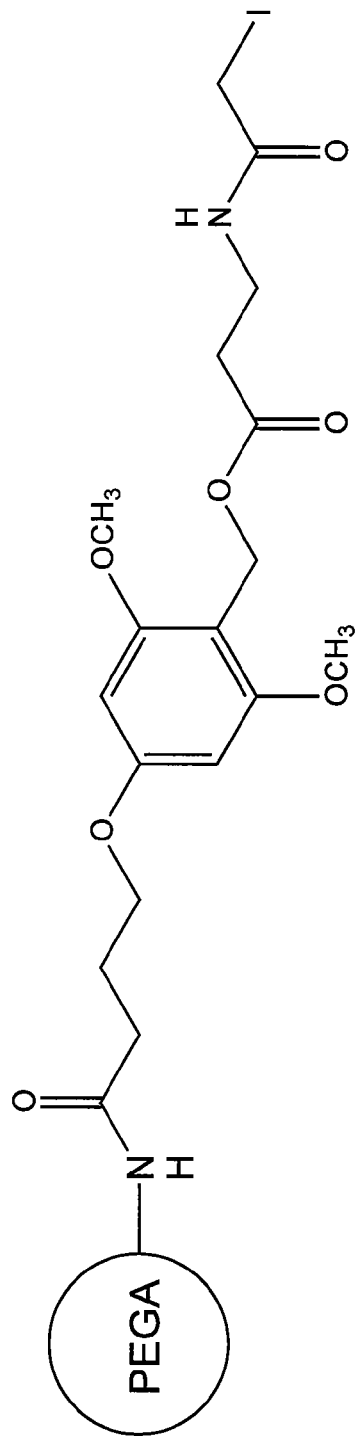
FIG. 14c is an illustration of an exemplary capture support.

FIG. 14a illustrates how, in some embodiments, the "control" sample and the "test" samples can be digested with an enzyme and then components of the sample can be captured on a solid phase through a cleavable linker. For example, the support can comprise a cleavable linker and a reactive group that reacts with moieties of a peptide (See: FIG. 14b for an illustration the basic components of such a support). A specific example of a support suitable for capturing cysteine containing peptides is illustrated in FIG. 14c. The thiol group of the cysteine containing peptides can react with the iodoacetate group of the illustrated support. Because not all peptides are expected to comprise cysteine, this is a method for reducing the complexity of the sample to be analyzed since those peptides without a cysteine moiety will flow through the support and not be captured. Once immobilized, according to the processing method illustrated in FIG. 14a, the amine groups of the peptides can be labeled with a labeling reagent (See: FIG. 14a). For example, each of the "control" and the "test" sample can be labeled with a different label of a set or isomeric and/or isobaric labeling reagents. The labeled peptide analytes can then be cleaved from the support and/or further processed (including forming a mixture) and/or analyzed (FIG. 14a).

Figure 16:
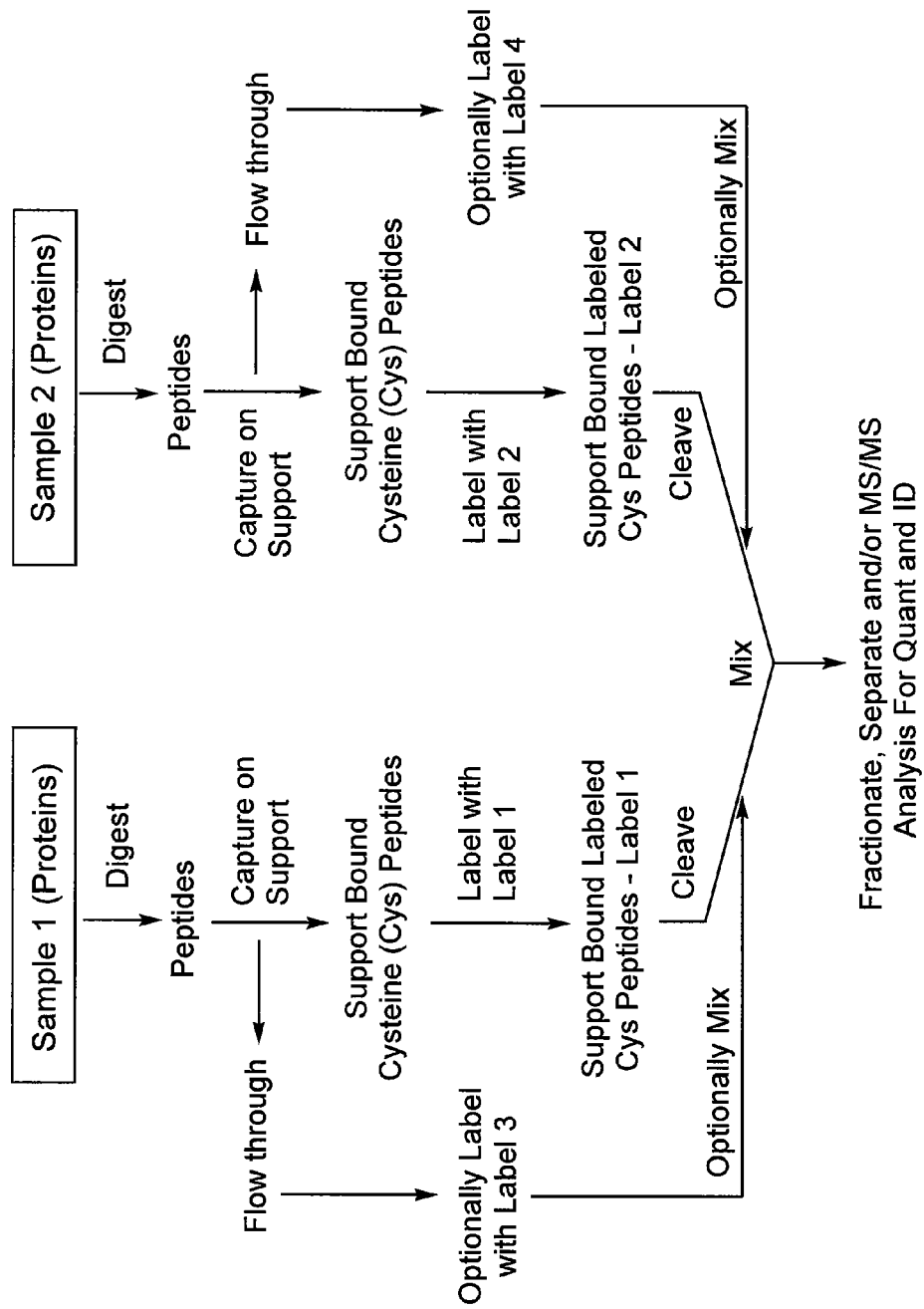
FIG. 16 is an illustration of one possible workflow for processing two protein samples using a set of isobaric labeling reagents (i.e. Label 1, Label 2, Label 3 and Label 4).
Figure 17:
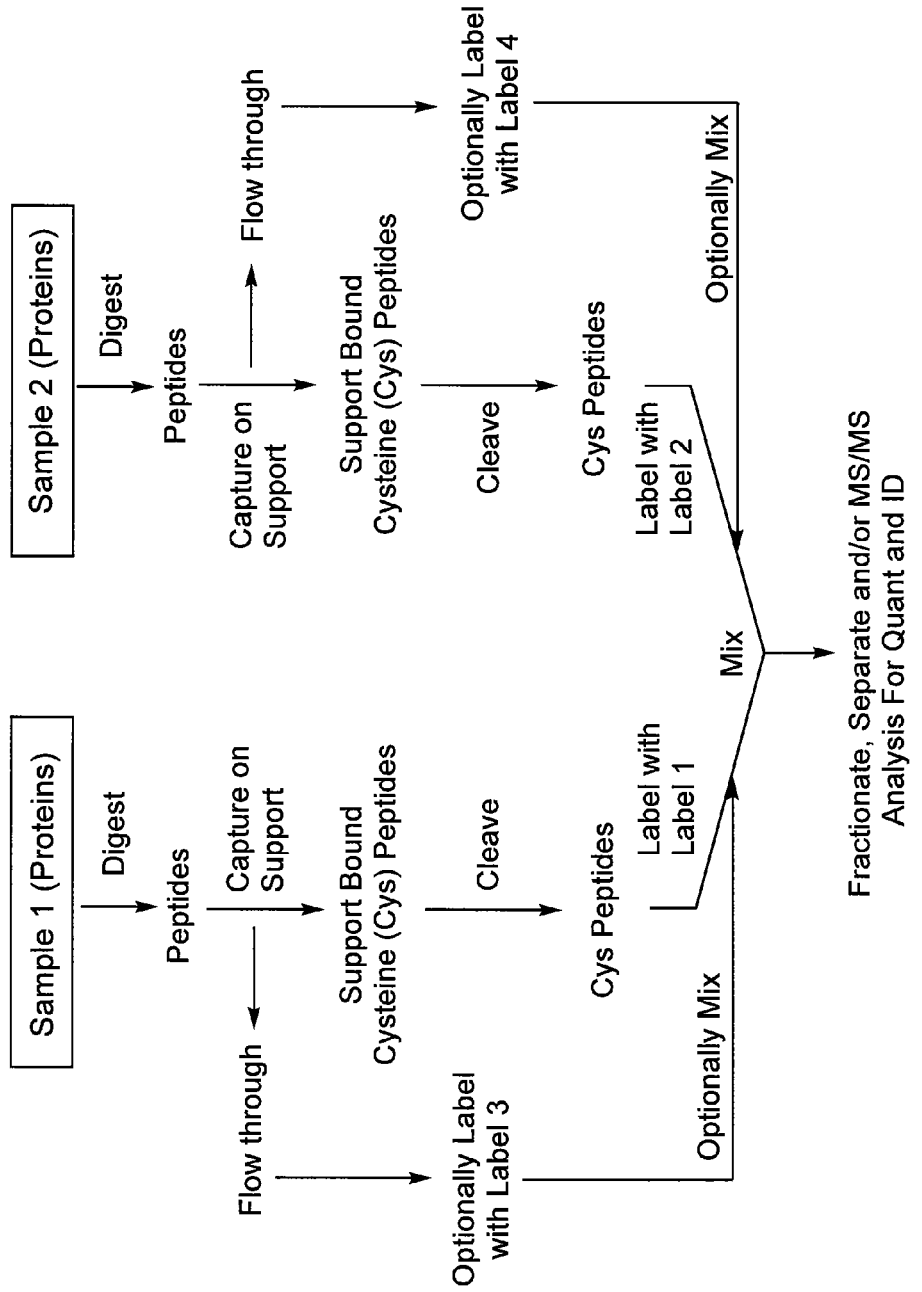
FIG. 17 is an illustration of one possible workflow for processing two protein samples using a set of isobaric labeling reagents (i.e. Label 1, Label 2, Label 3 and Label 4).

In some embodiments, the peptides that flow through the support (because they do not react with the functional group of the support) can (instead of being discarded) be collected, labeled with a labeling reagent of a set of isomeric and/or isobaric labeling reagents and be analyzed separately or together with the labeled peptides collected from the support. This type of workflow is illustrated in FIGS. 16 and 17. As illustrated in FIGS. 16 and 17, the peptides that flow through the solid support can be labeled with the same or with a different labeling reagent of a set of labeling reagents. Regardless of the labeling reagent, they can optionally be mixed with the sample mixture that is analyzed by MS/MS analysis. They also can be independently analyzed. FIGS. 16 and 17 differ in that it is possible to label the peptides retained on the support either while still on the support (FIG. 16) or after they have been cleaved from the support (FIG. 17).

Figure 18:
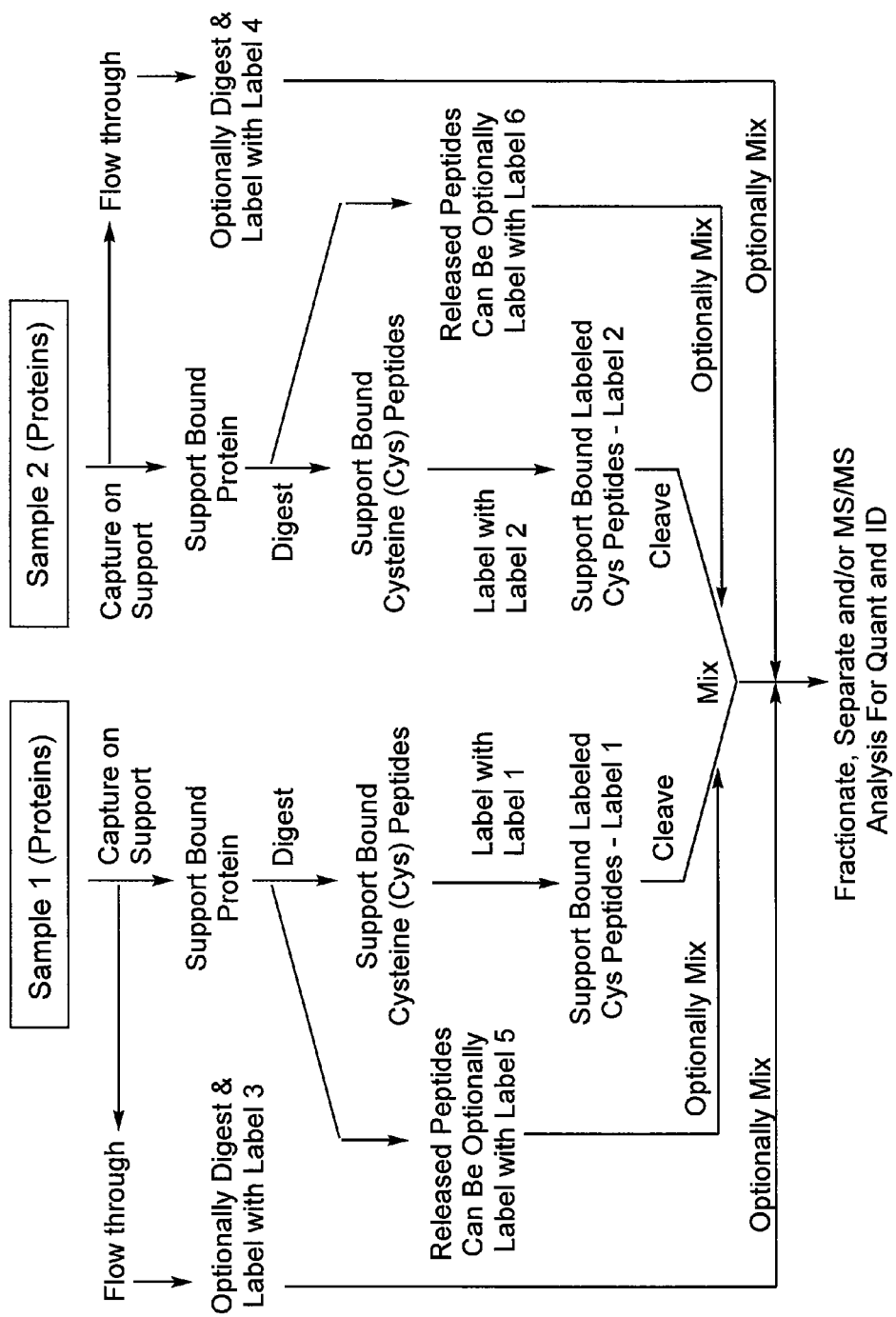
FIG. 18 is an illustration of one possible workflow for processing two protein samples using a set of isobaric labeling reagents (i.e. Label 1, Label 2, Label 3, Label 4, Label 5 and Label 6).
Figure 19A:
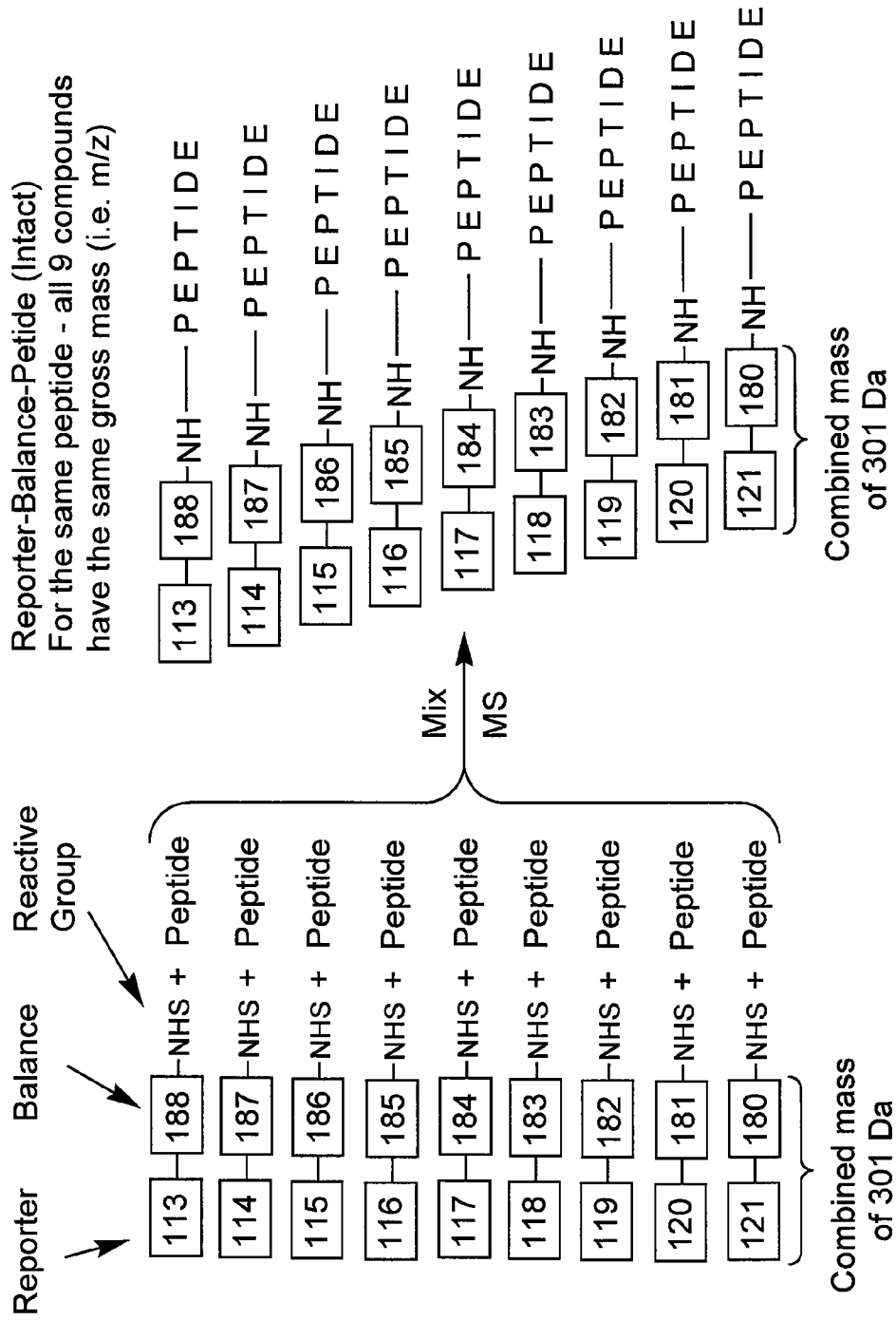
FIG. 19a is an illustration of the labeling and the product (at a particular m/z) of MS analysis of a peptide of selected mass derived from 9 different samples differentially labeled with a set of isobaric labeling reagents.
Figure 19B:
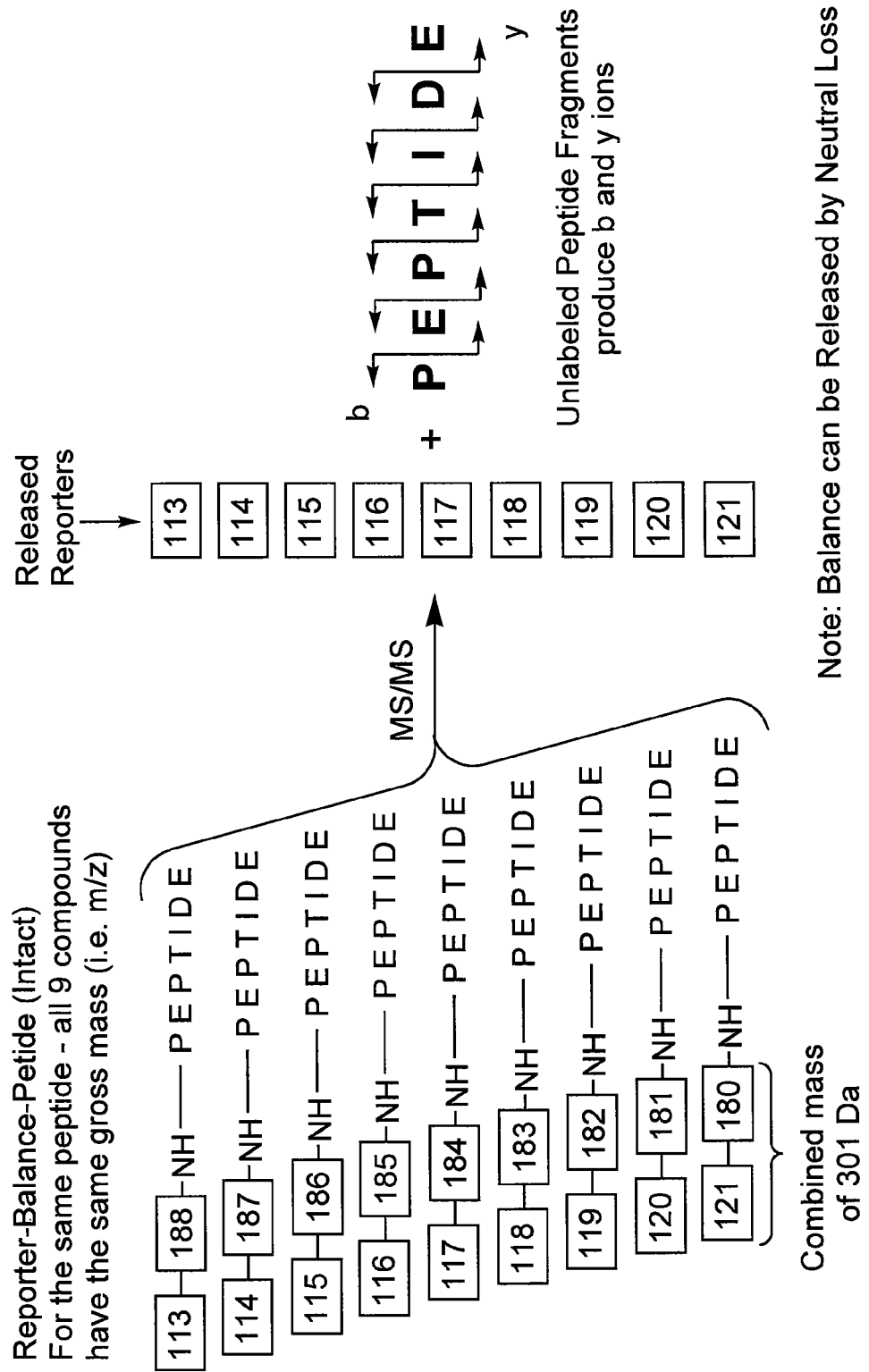

With reference to FIG. 18, it is also possible to use a solid support to capture the precursor proteins. As illustrated there can be two samples processed using a parallel path. A suitable support for capturing the cysteine moiety of proteins is illustrated in FIG. 14c. The proteins that do not comprise a cysteine moiety can be removed from the support with a wash and optionally be collected (i.e. flow through). They can also be optionally digested, labeled and/or analyzed with the sample mixture or be analyzed separately.

According to FIG. 18, the support bound proteins can be digested. The support bound cysteine comprising peptides can then be labeled with labeling reagent and cleaved from the support (option shown in the FIG. 18). The support bound cysteine comprising peptides can otherwise first be cleaved from the support and then labeled with labeling reagent (option not shown in FIG. 18). Labeled peptides from the different samples (optionally including the labeled peptides that do not comprise cysteine moieties) can be mixed, processed and/or analyzed with the sample mixture or be analyzed separately.

According to FIG. 18, it is also possible to collect any peptides that are released from the support as a consequence of performing the digestion. Typically these are peptides that do not comprise a thiol group. These peptides can optionally be labeled with a labeling reagent and optionally mixed, processed and/or analyzed with the sample mixture or be analyzed separately.

B) Exemplary Workflows Involving Labeling Followed by Digestion

Whether or not a support is used to capture an analyte for analysis, the step of labeling the analyte with a labeling reagent can be performed either before or after digestion or other chemical treatment provided that the treatment does not modify the label. For protein samples, it is also possible to reduce and cysteine block the sample protein, label the N-ε-lysine side chain amine groups of the sample protein with the labeling reagent and then digest the protein into labeled peptides.

Regardless of their origin, labeled analytes can be analyzed or they can be further processed (including preparing a sample mixture), for example by separation and/or by immobilization to a support. For example, it is possible to label a precursor protein by reaction of the labeling reagent with N-ε-lysine side chain amine groups of the sample protein and then optionally immobilize the labeled precursor protein to a support. The labeled protein can be cleaved from the support and then digested or the labeled protein can be digested while still support bound. In the latter case, support bound digestion will free peptides from the support that do not comprise a cysteine moiety. These can be collected and optionally analyzed either separately or as part of the sample mixture comprising the later released labeled peptides comprising cysteine moieties.

When the precursor proteins are labeled before digestion to peptides, the digestion pattern can be altered. For example, digestion with trypsin can be expected to produce predominately C-terminal arginine peptides because the N-ε-lysine side chain amine groups are modified with the label. Consequently, the activity of trypsin can be much like that of Arg-C. Because only those C-terminal arginine peptides that also comprise a lysine side chain can be labeled and therefore detectable in the mass spectrometer, this offers a way to further reduce the complexity of the sample to be further processed and/or analyzed.

In some embodiments, it is possible to reduce the protein and label the cysteine groups with labeling reagent (i.e. a thiol specific labeling reagent) and then digest the protein into labeled peptides for analysis. The labeled peptide analytes can be analyzed or can be further processed, for example by separation and/or immobilization to a support. For example, it is possible to immobilize labeled peptides to a support by reaction of the N-α-amine groups and/or the N-ε-amine groups of the lysine side chains with functional groups of the support. Supports with cleavable linkers for the immobilization of compounds comprising amine functional groups include supports comprising trityl linkers (See: Trityl chloride support (Trityl-Cl) or 2-Chlorotrityl chloride support available from Novabiochem (San Diego, Calif.)). This workflow is distinct from those described previously. The labeled analytes can be cleaved from the support, further processed and/or analyzed. This process might not provide substantial complexity reduction since all of the digested peptides are expected to comprise at least an N-α-amine group.

The foregoing examples are not intended to be exhaustive of various possible workflows. They are intended to be exemplary only. With regard to embodiments where labeling precedes digestion, it is also possible to engage in further sample processing prior to performing the digestion.

C) Summary

Whilst the preceding discussion focused, by way of specific example, on proteomic analysis and the determination of peptides and/or proteins as analytes, the concepts described are intended to encompass many types of analytes for which the preceding workflows are applicable without the exercise of undue experimentation. Accordingly, the scope of this disclosure is not intended to be limited to any of these specific examples discussed.

IV. Mixtures

In some embodiments, this invention pertains to mixtures (i.e. sample mixtures). For example, the mixtures can comprise isobarically and/or isomerically labeled analytes. Exemplary mixtures of labeled analytes and methods for their preparation and/or analysis have been described in the section entitled "Methods for Labeling and Analysis", set forth above.

The mixture can be formed by mixing all, or a part, of the product of two or more labeling reactions wherein each sample is labeled with a different labeling reagent of a set of labeling reagents wherein each labeling reagent comprises a reporter moiety of unique (gross) mass. The unique reporter moiety of each different labeling reagent can identify from which labeling reaction each of the two or more labeled analytes is derived (i.e. originated). The labeling reagents can be isotopically encoded isomeric and/or isobaric labeling reagents. Hence, two or more of the labeled analytes of a mixture can be isomeric and/or isobaric. Characteristics of the labeling reagents and labeled analytes associated with those methods have been previously discussed.

The analytes of the mixture can be peptides. The analytes of the mixture can be proteins. The analytes of the mixture can be peptides and proteins. The analytes of the mixture can be nucleic acid molecules. The analytes of the mixture can be carbohydrates. The analytes of the mixture can be lipids. The analytes of the mixture can be steroids. The analytes of the mixture can be small molecules having a mass of less than 1500 daltons. The analytes of the mixture comprise two or more different analyte types (e.g. 1) lipids and steroids; or 2) peptides, lipids, steroids and carbohydrates).

Mixtures can comprise any type of differentially labeled analytes comprising novel reporter/linker moiety disclosed herein. For example, the mixtures can comprise at least two differentially labeled analytes that can be represented by formula I";

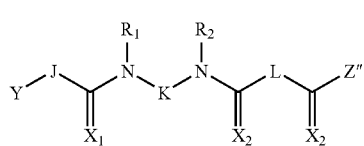

I"

including a salt form and/or hydrate form thereof, wherein the atoms or groups Y, J, K, L, $R_1$, $R_2$, $X_1$ and $X_2$ have been previously described and their characteristics disclosed. In some embodiments, each of the two-labeled analytes can originate from a different sample. According to formula I" the group Y-J, which group forms a reporter moiety, of each different labeled analyte can be uniquely encoded at one or more isotopically enriched sites such that when the bond between the group J, of the group Y-J, and the remainder of the labeled analyte fragments in a mass spectrometer, a reporter ion of unique mass is produced. The group Z" can be a covalently linked analyte. For each different label, some of the labeled analytes of the mixture can be the same and some of the labeled analytes can be different.

In some embodiments, the mixture can comprise at least two differentially labeled analytes that can be represented by formula II";

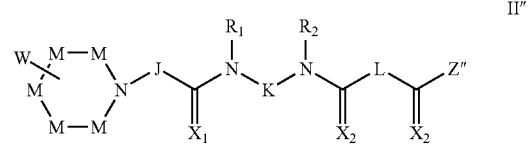

II"

including a salt form and/or hydrate form thereof; wherein W, M, J, K, L, $R_1$, $R_2$, $X_1$, $X_2$ and Z" are as previously described.

In some embodiments, the mixture can comprise at least two differentially labeled analytes that can be represented by formula III";

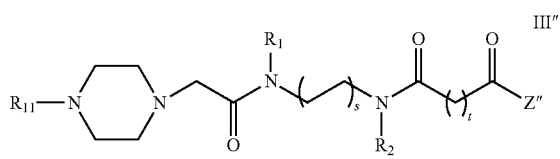

III"

including a salt form and/or hydrate form thereof, wherein s, t, $R_1$, $R_2$, $R_{11}$ and Z" are as previously described.

In some embodiments, the mixture can comprise at least two differentially labeled analytes that can be represented by formula;

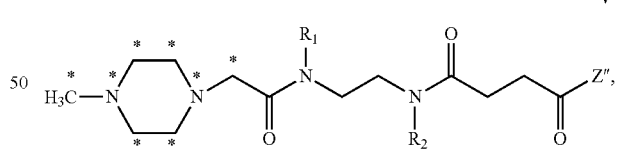

V"

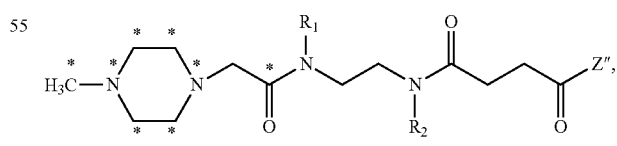

VI"

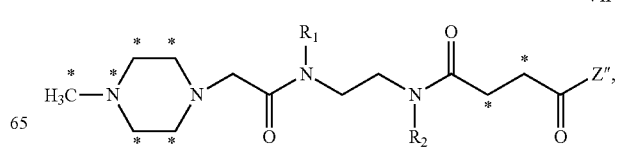

VII"

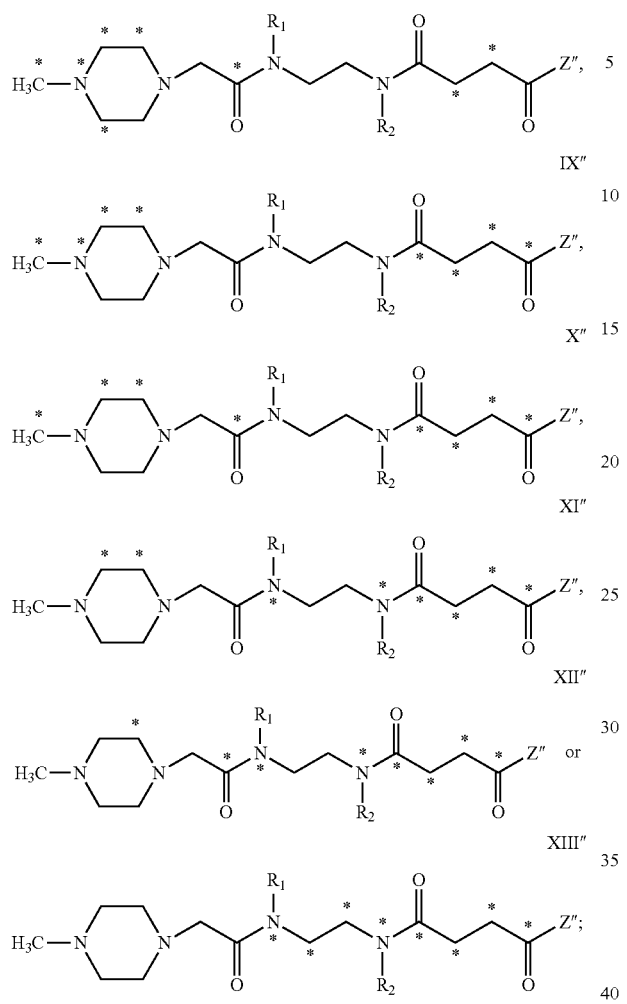

including a salt form and/or hydrate form thereof, wherein, *, $R_1$, $R_2$, and Z" are as previously described.

In some embodiments, the mixture can comprise at least two differentially labeled analytes that can be represented by formula IV'";

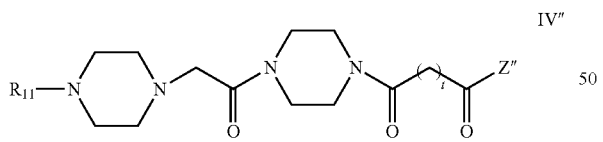

including a salt form and/or hydrate form thereof, wherein t, $R_{11}$ and Z" are as previously described.

In some embodiments, the mixture can comprise at least two differentially labeled analytes of formula:

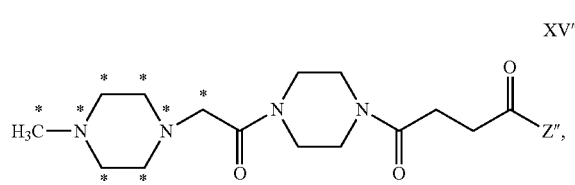

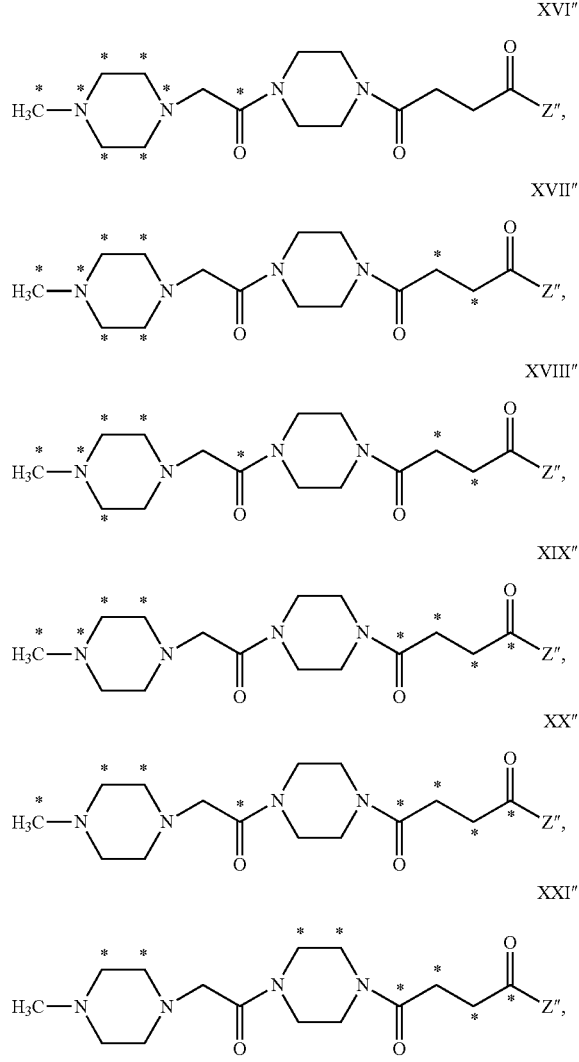

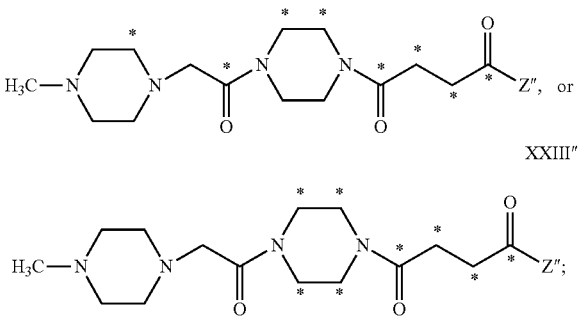

including a salt form and/or hydrate form thereof, wherein, * and Z" are as previously described.

In some embodiments, this invention is related to mixtures of fragment ions. For example, the fragment ions of the mixture can be generated by ionizing in a mass spectrometer a fraction of a sample mixture comprising at least two differentially labeled analyte molecules and selecting at least two of the differentially labeled analyte molecules, at a selected m/z value, for fragmentation. The selected differentially labeled analyte molecules can then be fragmented by application of dissociate energy levels. In some embodiments at least one of the differentially labeled analyte molecules is a compound of a formula selected from the group consisting of: 80", 81", 82", 83", 84", 85", 86" and 87" as illustrated in FIGS. 26a-26b. Thus, the fragment ion can have a molecular formula of: $^{13}C_6H_{13}{}^{15}N_2{}^+$, $^{13}C_4C_2H_{13}{}^{15}N_2{}^+$, $^{13}C_3C_3H_{13}{}^{15}N_2{}^+$, $^{13}C_3C_3H_{13}{}^{15}NN^+$, $^{13}C_2C_4H_{13}{}^{15}NN^+$, $^{13}CC_5H_{13}{}^{15}NN^+$, $^{13}CC_5H_{13}N_2{}^+$ or $C_6H_{13}N_2{}^+$. In some embodiments, the molecular formula is selected from $^{13}C_6H_{13}{}^{15}N_2{}^+$, $^{13}C_4C_2H_{13}{}^{15}N_2{}^+$ and $^{13}C_3C_3H_3\ {}^{15}N_2{}^+$.

V. Kits

In some embodiments, this invention pertains to kits. The kits can comprise a labeling reagent as described herein and one or more other reagents, containers, enzymes, buffers and/or instructions. The kits can comprise a set of two or more labeling reagents and one or more other reagents, containers, enzymes, buffers and/or instructions. Two or more of the labeling reagents of a kit can be isomeric and/or isobaric. For example, the one or more labeling reagents of the kits can be compounds (including sets of compounds) of the formula: I', II', III', IV', V', VI', VII', VIII', IX', X', XI', XII', XII', XV', XVI', XVII', XVIII', XIX', XX', XXI', XXII' and/or XXIII', as previously disclosed herein. In some embodiments, the kit can comprise a labeled analyte (for example as a calibration standard) of formula: I", II", III", IV", V", VI", VII", VIII", IX", X", XI", XII", XIII", XV", XVI", XVII", XVIII", XIX", XX", XXI", XXII" and/or XXIII", as previously disclosed herein. Other properties of the labeling reagents of the kits have been disclosed. The kits can, for example, be useful for the multiplex analysis of one or more analytes in the same sample, or in two or more different samples.

VI. Illustrative Method for the Manufacture of Labeling Reagents

With reference to FIGS. 7a-7c, FIGS. 27a-27c and 20-21, a general synthetic strategy that can be used for the preparation of isotopically encoded labeling reagents will be discussed as still another embodiment of the invention. It is to be understood that these illustrated methods each represent one of many possible synthetic procedures that can be used to prepare isotopically encoded labeling reagents. It is also to be understood that the ordinary practitioner, using no more that routine experimentation and the disclosure provided herein, could easily adapt this procedure for the production of other labeling reagents of similar chemical structure. Accordingly, the disclosure of this method is intended to be illustrative and is not intended to either be exhaustive or to be limiting in any way.

Figure 7A:
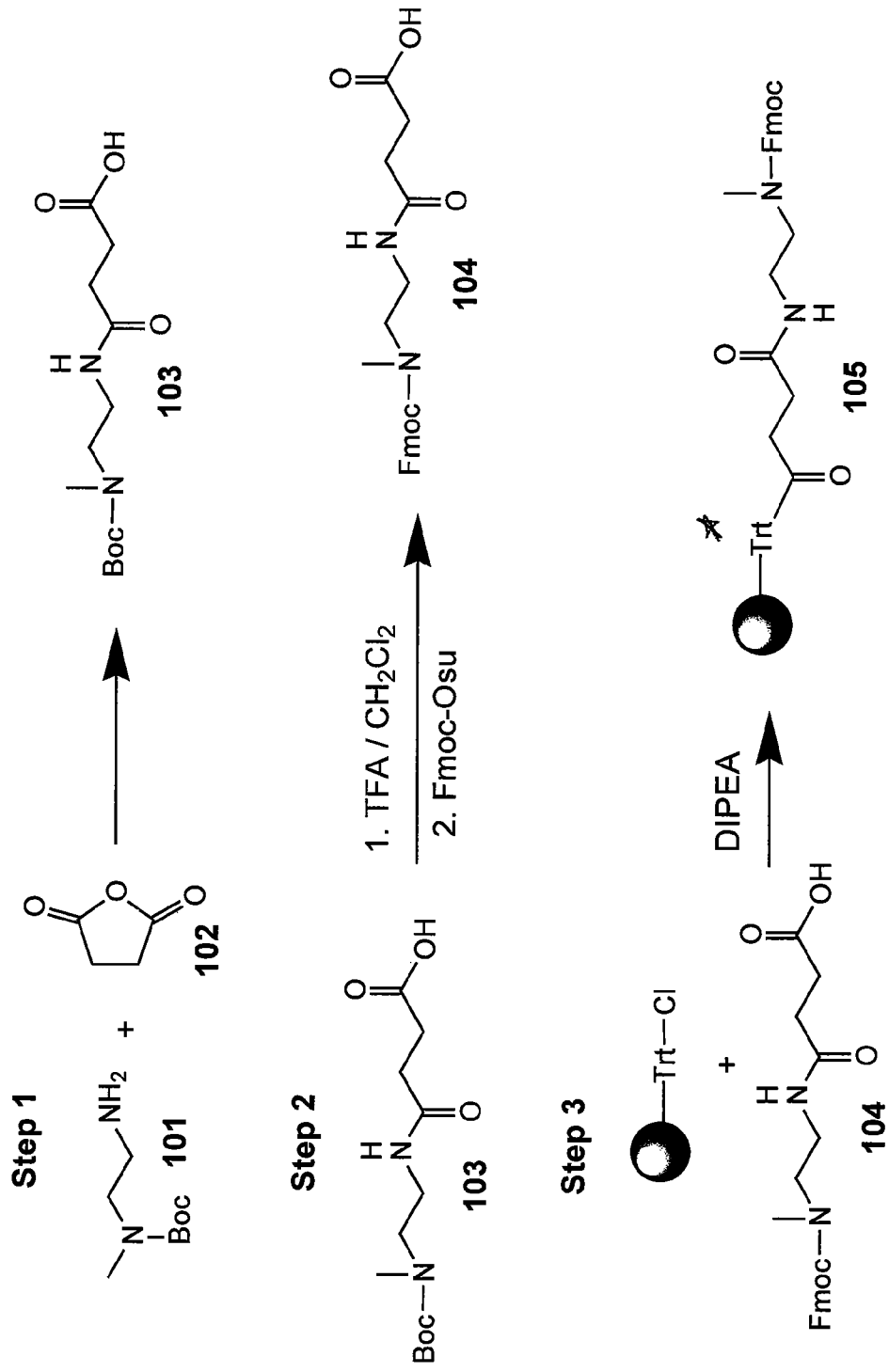
FIG. 7a is an illustration of Steps 1-3 of an exemplary synthesis of an exemplary labeling reagent.
Figure 7B:
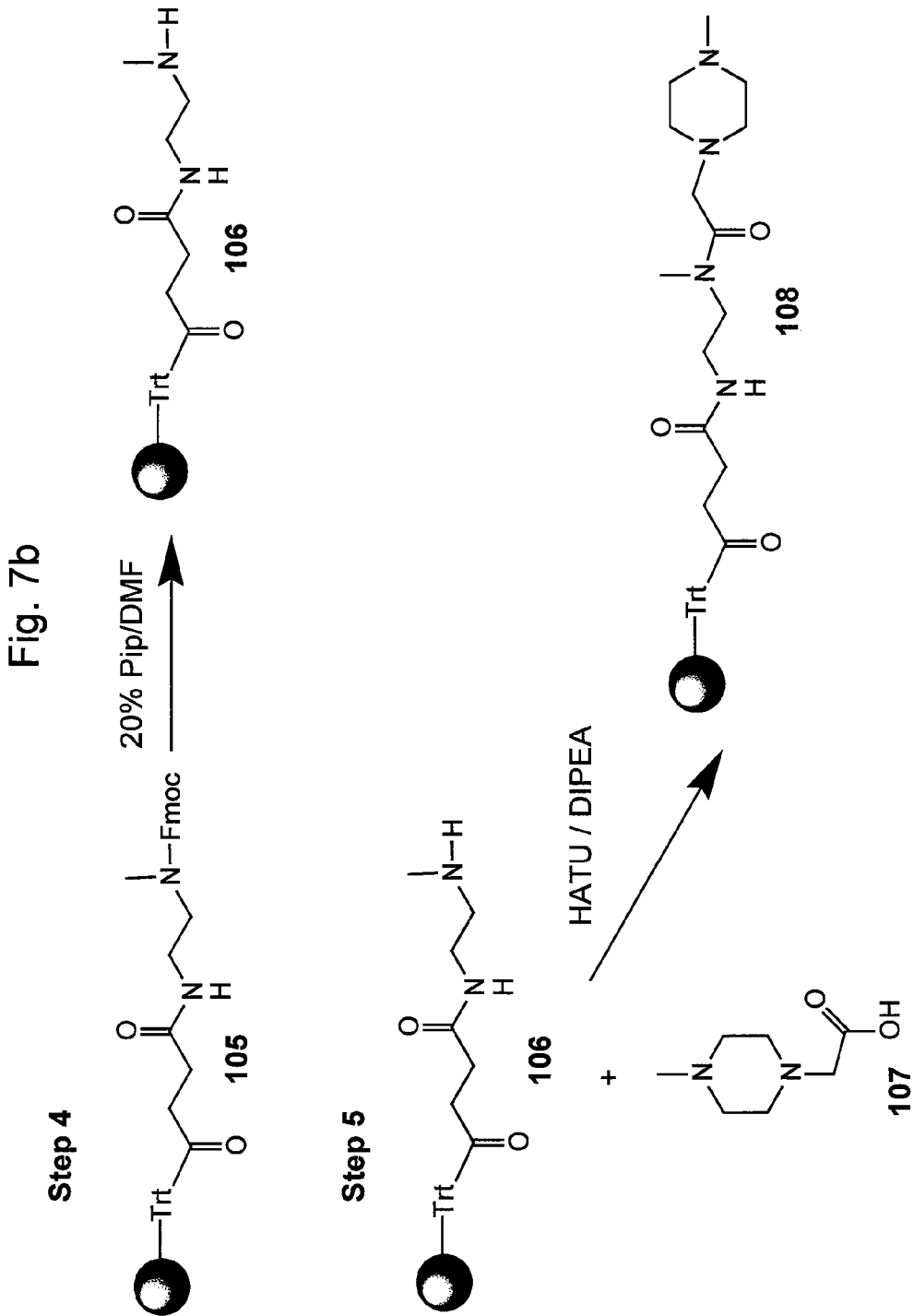
FIG. 7b is an illustration of Steps 4-5 of an exemplary synthesis of an exemplary labeling reagent.

Although the method illustrated in FIGS. 7a-7c, FIGS. 27a-27c and 20-21 are presented for uncoded compounds, it is self-evident that isotopically encoded reagents can be substituted for the uncoded compounds to thereby produced isotopically encoded products since the encoded materials should be substantially identical in reactivity as compared with the uncoded version. The method presented in FIGS. 7a-7c is supported by Examples 1-9 discussed below. These example also support the method illustrated in FIGS. 20-21. Exemplary isotopically encoded compounds that can be produced using the illustrated methods are described in this specification and the associated Figures (e.g. FIGS. 9a-9c, 10a-10c, 12a-12e, 28a-28b and 29a-29b) and claims.

Figure 20:
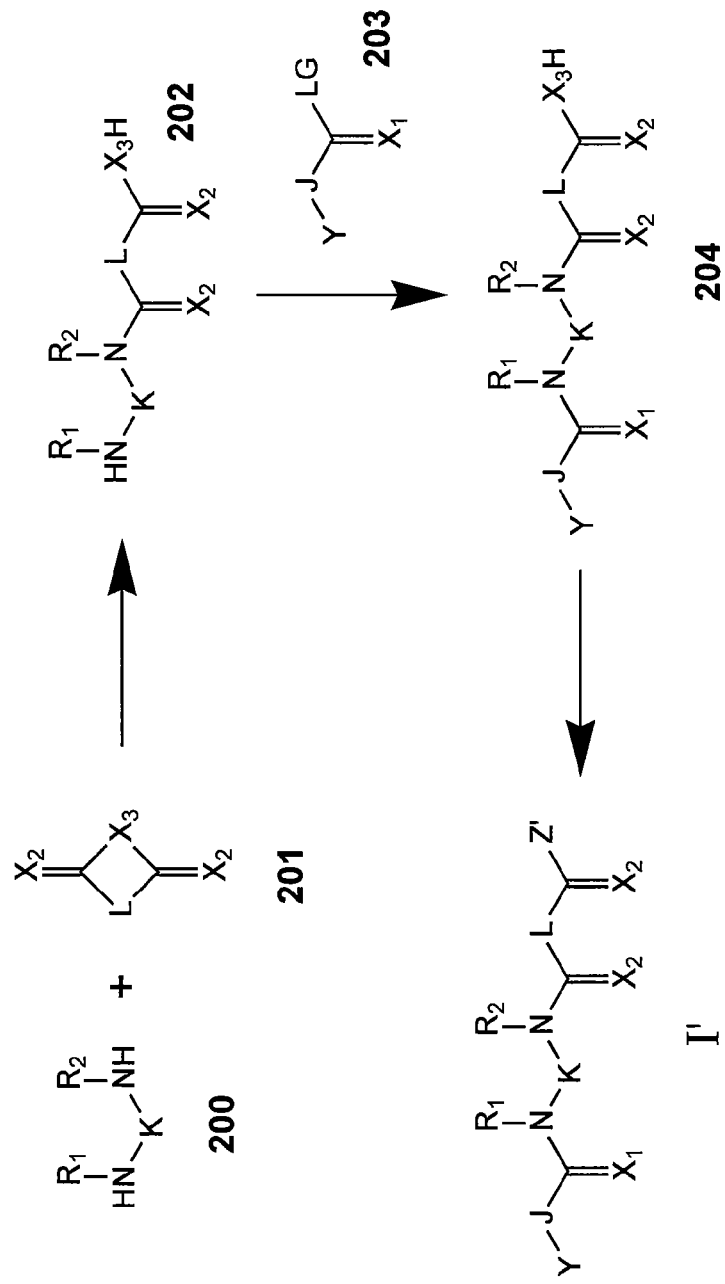
FIG. 20 is an illustration of a possible route to some exemplary labeling reagents.
Figure 21:
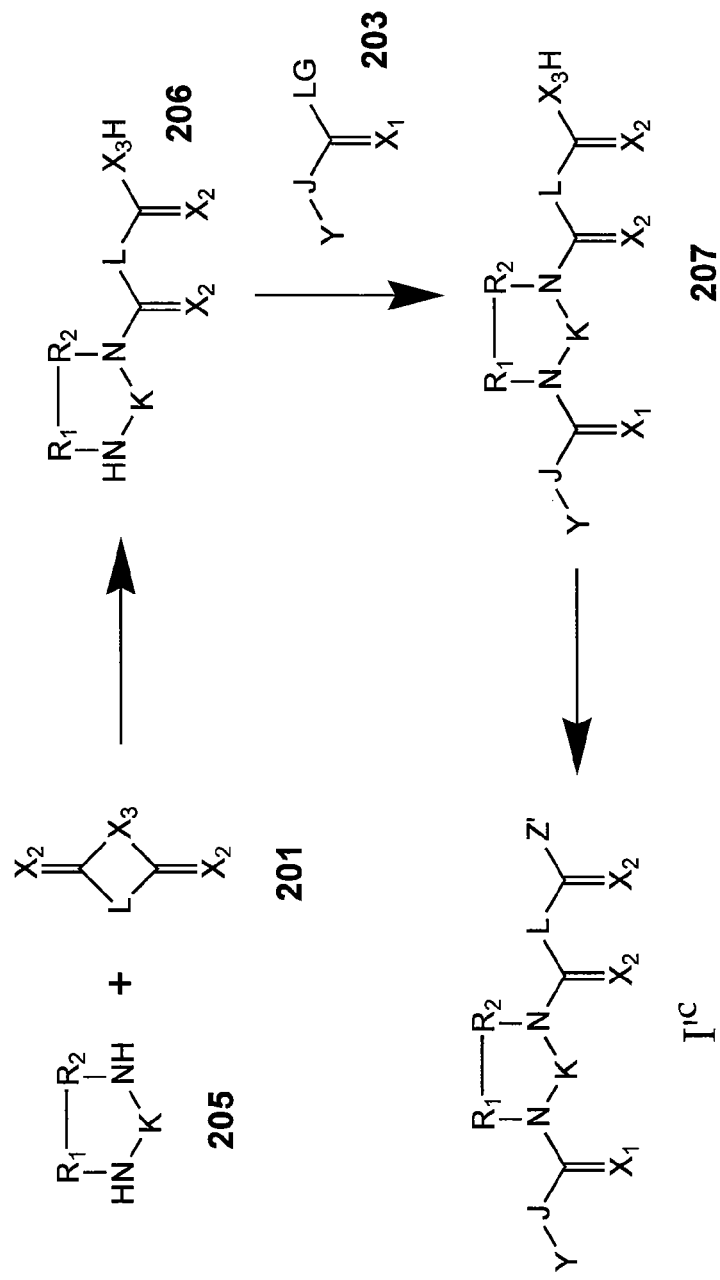
FIG. 21 is an illustration of a possible route to some exemplary labeling reagents.
Figure 27A:
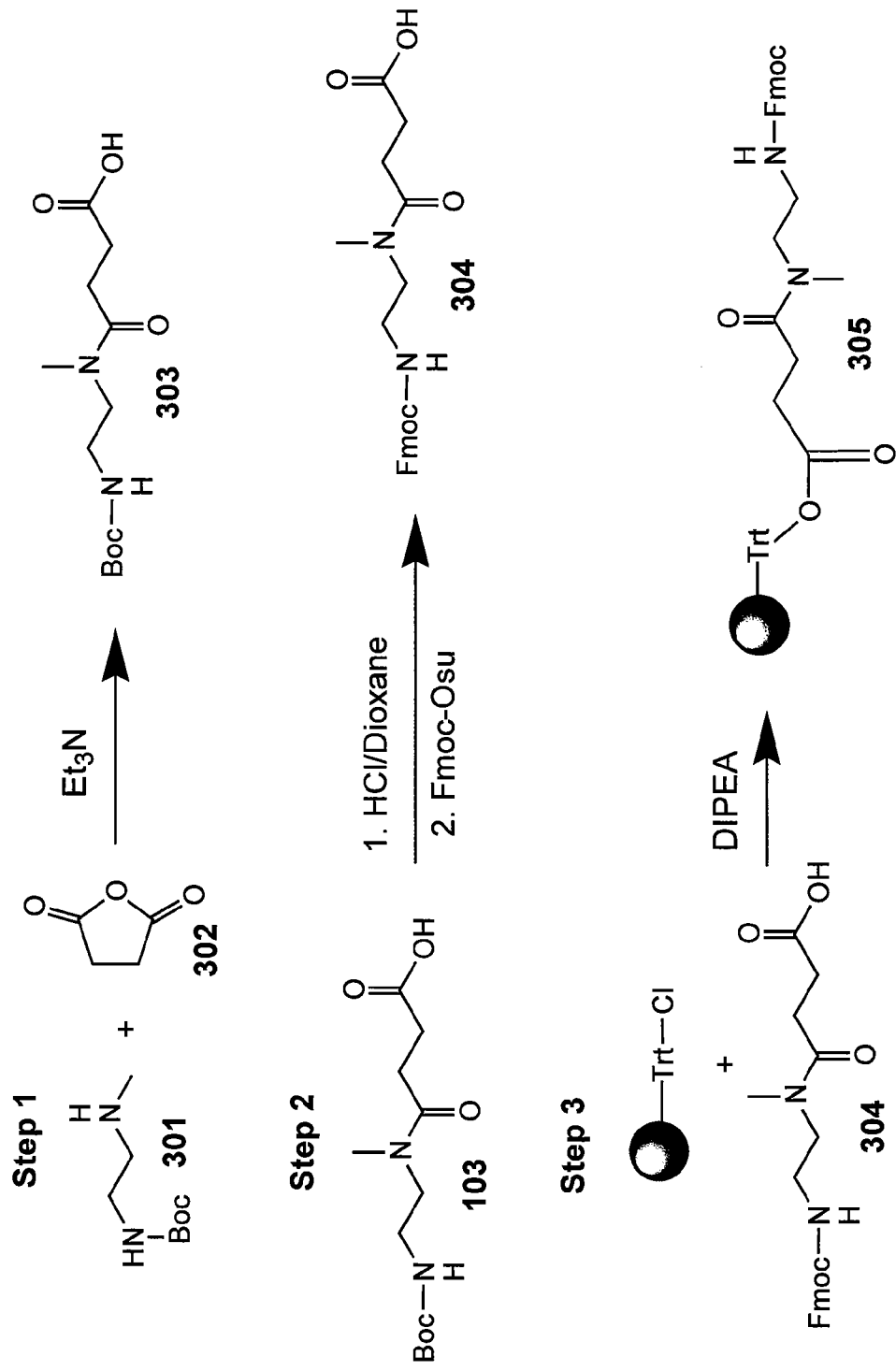
FIG. 27a is an illustration of Steps 1-3 of an exemplary synthesis of an exemplary labeling reagent.

With reference to FIGS. 7a and 27a, Step 1 and FIGS. 20-21, a substituted or unsubstituted diamine can be reacted with a substituted or unsubstituted dicarboxylic acid or anhydride. The product of the reaction is an amino acid comprising at least one amide bond (or thioamide bond) that links the dicarboxylic acid or anhydride to the diamine. For example, the substituted or unsubstituted diamine can have the structure illustrated as compound 200 in FIG. 20 and the substituted or unsubstituted anhydride can have the structure illustrated as compound 201 in FIG. 20. The amino acid product of the reaction can have the structure illustrated as compound 202 in FIG. 20.

One or both of the amine groups of the substituted or unsubstituted diamine can comprise an N-alkylated group, illustrated in the figures as $R_1$ and/or $R_2$ (see for example FIG. 27a). The diamine can be partially protected with an amine protecting group, such as t-butyloxycarbonyl (t-boc) or 9-Fluorenyloxycarbonyl (Fmoc) group. Other suitable amine protecting groups, and methods for their use, can be found in Green et al., Protective Groups In Organic Synthesis, Third Edition, John Wiley & Sons, Inc. New York, 1999. The ordinary practitioner will be able to select and use other suitable protecting groups using no more that routine experimentation and the disclosure provided herein.

If a dicarboxylic acid is selected as the starting material, one of the carboxylic acid groups can be protected with a protecting, such as by formation of a bulky ester (e.g. a t-butyl ester). It is to be understood that, as used herein, the dicarboxylic acid or anhydride can comprise sulfur atoms as substitutes for the oxygen atoms of the two carboxylic acid groups or the anhydride group.

In some embodiments, neither the dicarboxylic acid nor diamine is protected. Generally, protection is used to direct the reaction so as to avoid the production of impurities. However, if the reagents react to produce the desired compounds and/or purification is easily achieved, protection is not necessary. For example, protection often can be avoided if the starting materials are symmetrical.

It is also to be understood that in some embodiments, not all of the disclosed steps need to be performed. As stated in the Examples, selection of an Fmoc protected diamine can eliminate the need to perform Step 2 of the illustrated method (FIGS. 7a-7c and FIGS. 27a-27c).

With reference to FIG. 20, the substituted or unsubstituted diamine can comprise an alkyl group represented by K (e.g. compound 200) wherein K can be a group of formula $-(CK'_2)_n-$ or $-((CK'_2)_m-X_3-(CK'_2)_m)_p-$, that bridges the two amine groups, wherein n is an integer from 2 to 10, each m is, independently of the other, an integer from 1 to 5, p is an integer from 1 to 4 and each K' is, independently of the other, hydrogen, deuterium, fluorine, chlorine, bromine, iodine, $-R_4$, $-OR_4$, $-SR_4$, $-R_4'OR_4$ or $-R_4'SR_4$, wherein $R_4$, is alkyl, alkenyl, alkynyl, aryl, heteroaryl or arylalkyl. The substituted or unsubstituted diamine can also comprise a cyclic ring such as piperazine wherein one or both of the two amine groups of the diamine are ring nitrogen atoms (e.g. compound 205, FIG. 21). In some embodiments, one or more of the atoms of the substituted or unsubstituted diamine can be substituted with a heavy atom isotope. With reference to FIGS. 20 and 21, the amino acid compound formed by reaction of a substituted or unsubstituted diamine with an anhydride is represented by 202 and 206, respectively.

The substituted or unsubstituted dicarboxylic acid or anhydride can comprise a group L (e.g. compound 201, FIG. 20) wherein L is represented by formula $-(CL'_2)_q-$ or $-((CL'_2)_m-X_3-(CL'_2)_m)_p-$, that bridges the two carboxylic acid groups or the two carbonyl groups of the anhydride, wherein q is an integer from 1 to 10, each m is, independently of the other, an integer from 1 to 5, p is an integer from 1 to 4 and each L' is, independently of the other, hydrogen, deuterium, fluorine, chlorine, bromine, iodine, $-R_5$, $-OR_5$, $-SR_5$, $-R_5'OR_5$ or $-R_5'SR_5$, wherein $R_5$ is alkyl, alkenyl, alkynyl, aryl, heteroaryl or arylalkyl. The substituted or unsubstituted dicarboxylic acid or anhydride can comprise a cyclic ring such as cyclohexane or cyclopentane ring wherein one or both of the carboxylic acid moieties (or the carbonyl groups of the anhydride formed by the two carboxylic acid groups) are a substituent of the cyclic ring. In some embodiments, one or more of the atoms in the substituted or unsubstituted dicarboxylic acid or anhydride can be substituted with a heavy atom isotope.

As illustrated in FIG. 7a, Step 1, N-(t-boc)-N-methyl-ethylenediamine 101 can be reacted with succinic anhydride 102. This reaction produces the product, N-methyl ethylenediamine-N'-succinate 103. For compounds such as those illustrated by formulas I-XIII' and VI'-XXIII', this reaction can represent one method for isotopic encoding of the linker moiety. Possible diamine and anhydride starting materials that can produce compounds of formulas I'-XIII' and VI'-XXIII' using the disclosed procedure (without Step ) are illustrated in FIGS. 9a-9c and 10a-10c.

Figure 27B:
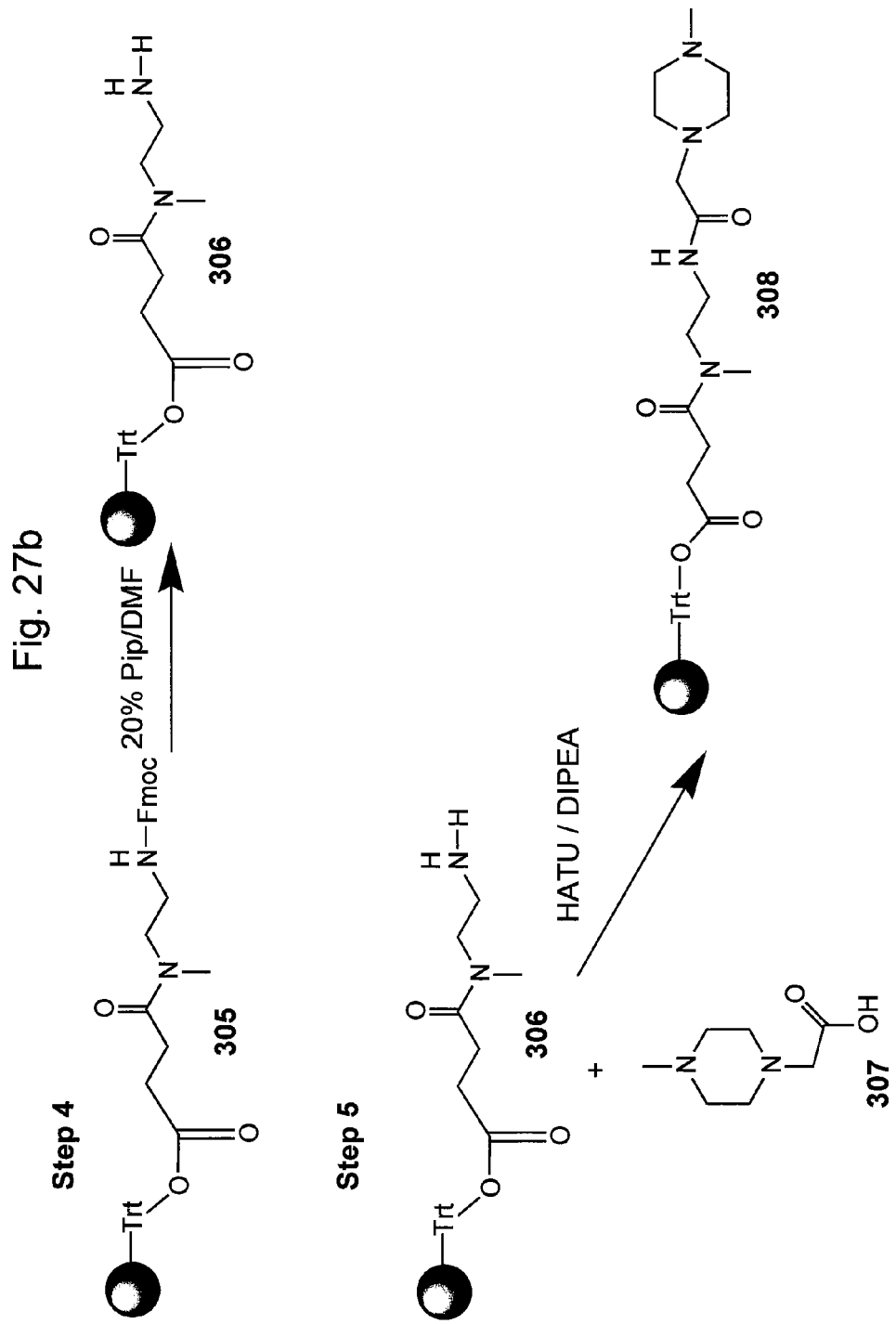
FIG. 27b is an illustration of Steps 4-5 of an exemplary synthesis of an exemplary labeling reagent.

With reference to FIGS. 7a and 7b as well as FIGS. 27a and 27b, Steps 2-4, the amine and acid functional groups of the amino acid product of Step 1 can be manipulated for purposes of producing a support bound moiety to which a compound comprising a reporter moiety can ultimately be linked. As illustrated in FIG. 7a, Step 2, a t-boc amine protecting group is exchanged for an Fmoc amine protecting group thereby producing the Fmoc protected compound 104. In Step 3 (FIG. 7a), the compound is immobilized to a support, via its carboxylic acid functional group, through a cleavable linker to thereby produce the support bound compound 105. The support to which the linker moiety is immobilized can comprise a sterically hindered cleavable linker. Numerous supports comprising cleavable linkers are well known to the ordinary practitioner. Non-limiting examples of sterically hindered solid supports include: Trityl chloride support (trityl-Cl, Novabiochem, P/N 01-64-0074), 2-Chlorotrityl chloride support (Novabiochem, P/N 01-64-0021), DHPP (Bachem, P/N Q-1755), MBHA (Applied Biosystems P/N 400377), 4-methyltrityl chloride support (Novabiochem, P/N 01-64-0075), 4-methoxytrityl chloride support (Novabiochem, P/N 01-64-0076), Hydroxy-(2-chorophenyl)methyl-PS (Novabiochem, P/N 01-64-0345), Rink Acid Support (Novabiochem P/Ns 01-64-0380, 01-64-0202) and NovaSyn TGT alcohol support (Novabiochem, P/N 01-64-0074). As illustrated in the Figure, a trityl chloride support can be used (See: Example 3).

As illustrated in FIG. 7b, Step 4, the protecting group of the terminal amine, of the support bound compound 105, can be removed to thereby facilitate the reaction of said amine, of the support bound product compound 106, with a compound comprising a reporter moiety.

Thus generally, the amine group of the amino acid product can be reacted with the compound comprising the reporter moiety to thereby form the reporter/linker combination. As indicated in FIGS. 7a-7c and FIGS. 27a-27c, in some embodiments, this reaction can be facilitated by immobilizing the linker moiety onto a solid support. It is to be understood however that albeit useful in some embodiments, immobilization of the linker moiety is not essential.

The compound comprising the reporter moiety generally comprises two features. One feature can be a substituted or unsubstituted N-alkylated acetic acid moiety wherein the carboxylic acid (or thiocarboxylic acid) group of the acetic acid moiety can be reacted with the amine group of the amino acid product to thereby form an amide bond (or thioamide bond). The second feature can be a nitrogen atom covalently linked to the methylene carbon of the acetic acid moiety. The moiety comprising the nitrogen atom can be a substituted secondary amine such as dimethylamine, diethylamine or propylamine. The moiety comprising the nitrogen atom can be a cyclic compound such as a substituted or unsubstituted piperidine, piperazine or morpholine. As illustrated in FIG. 7b, the nitrogen containing moiety is an N-methyl-piperazine.

With reference to FIGS. 20 and 21, the amino acid product (202 or 206, respectively), can be reacted with the compound comprising the reporter (i.e. compound 203). The product of this reaction can form the reporter/linker moiety (i.e. compounds 204 and 207, respectively).

With reference to FIG. 7b, Step 5, the terminal amine of compound 106 can be reacted with a substituted or unsubstituted N-alkyl piperazine acetic acid moiety (107) to thereby produce a support bound reporter/linker composition 108.

Of course the compound comprising the reporter moiety can comprise one or more isotopically enriched sites. For example, the substituted or unsubstituted N-alkyl piperazine or the N-alkylated acetic acid moiety of FIG. 7c can comprise one or more isotopically enriched sites (also see FIGS. 9a-9c and 10a-10c). Thus, the encoding of the reporter and linker can be controlled depending upon the encoding of the diamine, diacid (or anhydride) and compound comprising the reporter moiety (e.g. substituted or unsubstituted N-alkyl piperazine acetic acid).

In some embodiments, the carboxylic acid or thiocarboxylic acid group of molecule representing the reporter/linker can be in-situ activated to thereby facilitate labeling of an analyte. Thus, in some embodiments, no additional reaction is needed.

In some embodiments, the acid or thio acid group of the molecule representing the reporter/linker combination can be modified in a way that forms a reactive group capable of reacting with a functional group of an analyte. In some embodiments, this may involve reaction with one or more reagents that create a desired reactive group that can be reacted with a functional group of an analyte. In some embodiments, this may involve the conversion of the acid or thioacid group to an activated compound. For example, the carboxylic acid or thiocarboxylic acid group of the reporter/linker combination can be activated to thereby prepare an active ester comprising an alcohol or thiol leaving group wherein the active ester can react with a functional group of an analyte to thereby form a labeled analyte.

With reference to FIGS. 20 and 21, the compound representing the reporter/linker compound (compounds 204 and 207, respectively) can be modified to thereby produce the compound represented by I' or I", respectively. For example, the carboxylic acid or thiocarboxylic acid group can be converted to an active ester such as an N-hydroxysuccinimidyl ester.

With reference to FIG. 7c, Step 6, the reporter/linker compound can be cleaved from the support to thereby produce the intermediate 109. As illustrated, the intermediate comprises a carboxylic acid group that can be activated for reaction with a nucleophile, such as an amine group of a protein or peptide. Although the carboxylic acid can, in some embodiments, be activated in-situ as discussed previously, with reference to FIG. 7c, Step 7, the formation of an N-hydroxysuccinimidyl ester 111 by reaction with N-hydroxysuccinimidyl trifluoroacetate (110) is illustrated. Other methods suitable for forming active esters of the reporter/linker compound can be found in co-pending and co-owned United States Published Patent Application Serial No. US 2005-0148771 A1. Exemplary syntheses are illustrated in FIG. 8. The leaving groups of some exemplary active esters are illustrated as 7-19.

Figure 9C:
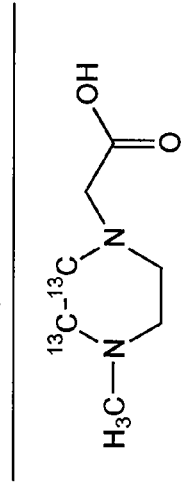
FIG. 9c is a Table illustrating the isotopically encoded source materials that can be used to prepare various isobaric compounds by practice of the invention(s) disclosed herein.
Figure 12B:
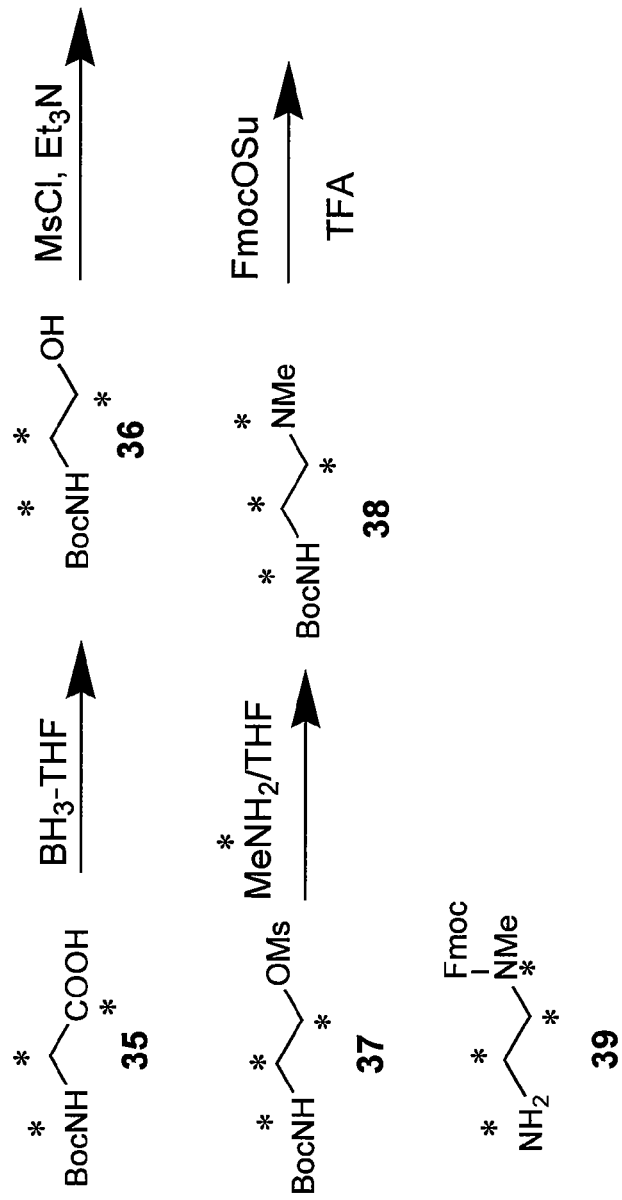
FIG. 12b is an illustration of one possible synthetic route to an encoded N-methyl ethylene diamine comprising four isotopically encoded sites.
Figure 12C:
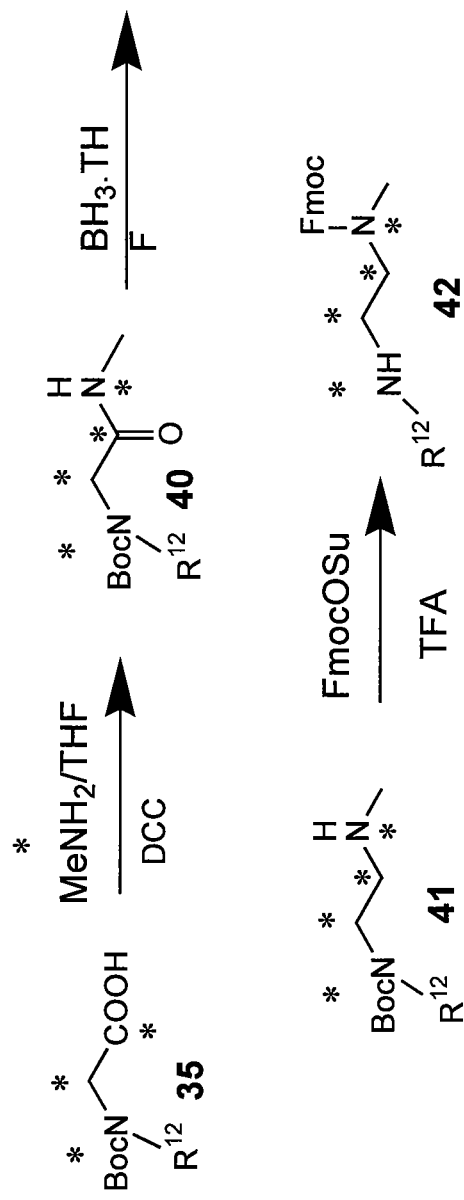
FIG. 12c is an illustration of one possible synthetic route to an encoded N-methyl ethylene diamine comprising four isotopically encoded sites.
Figure 12D:
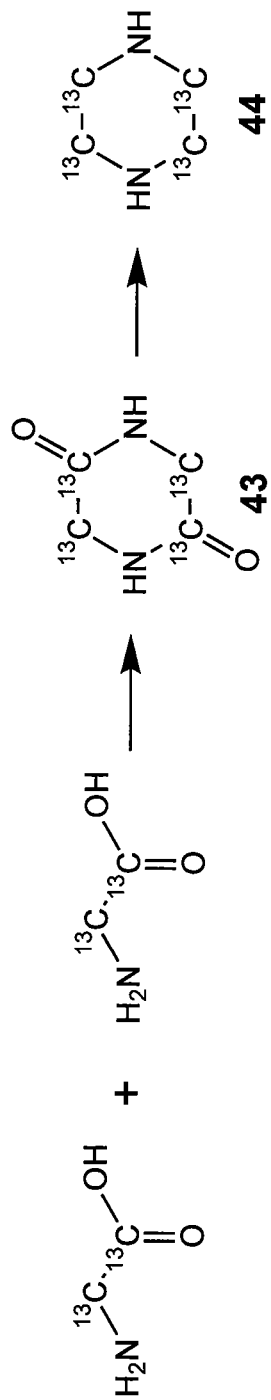
FIG. 12d is an illustration of one possible synthetic route to an encoded piperazine comprising four isotopically encoded sites.
Figure 12E:
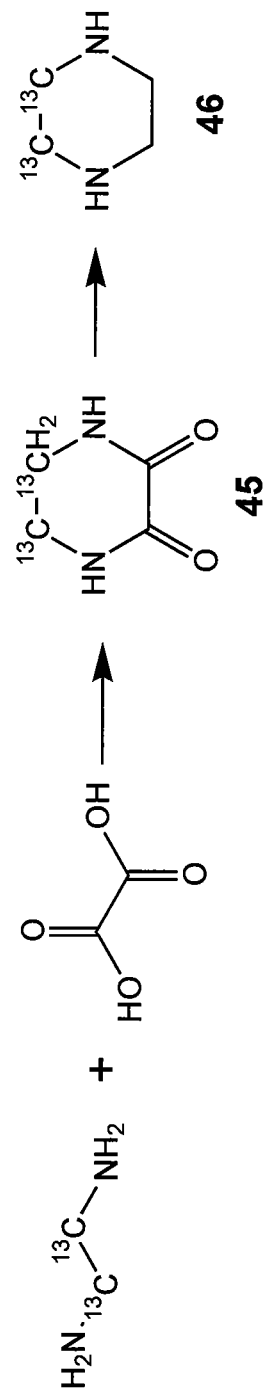
FIG. 12e is an illustration of one possible synthetic route to an encoded piperazine comprising two isotopically encoded sites.

FIGS. 9a-c illustrate possible source isotopically encoded starting materials that can be used with the illustrated methods to thereby produce compounds V'-XIII'. FIGS. 10a-c, wherein coded piperazine can be substituted for the derivatives of N-methyl ethylenediamine in FIGS. 7a-7c, illustrates possible source isotopically encoded starting materials that can be used to produce compounds XV'-XXIII'. Methods for the preparation of encoded piperazine from simple, readily available, starting materials such as encoded glycine and derivatives of glycine (e.g. sacrosine) are known in the art. For example, methods for the preparation of all the different flavors of encoded piperazine and N-alkyl piperazine compounds can be found in copending and commonly owned United States Published Patent Application Nos. US 2004-0219685 A1, US 2005-0147982, US 2005-0147985 and US 2005-1048774 A1. FIGS. 12*d* and 12*e* also illustrate examples of synthetic routes to encoded piperazine compounds that are illustrated in FIG. 10*c*. The synthetic routes illustrated in FIGS. 12*d* and 12*e* are based upon the methods for preparation of encoded piperazine compounds as described in the published patent applications.

As previously stated, encoded starting materials, such as encoded glycine, sarcosine and succinic anhydride, are available from various commercial sources such as Cambridge Isotope Laboratories, Andover, Mass. (See: list or "basic starting materials" at www.isotope.com) and Isotec (a division of Sigma-Aldrich). Cambridge Isotope Laboratories and Isotec will also prepare desired compounds under custom synthesis contracts. Id. References to the source and part numbers of various isotopically encoded starting materials can found throughout this disclosure, including in the Examples and Figures. However, these references are informational purposes only and are not intended to be limiting to the claimed invention or exhaustive of all possible commercial sources.

Figure 11A:
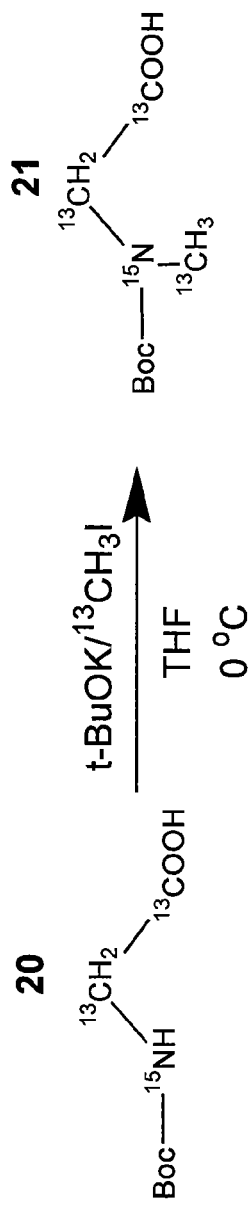
FIG. 11a is an illustration of one possible synthetic route to an encoded sarcosine derivative that can be used in the preparation of encoded N-methyl-piperazine derivatives.
Figure 11B:
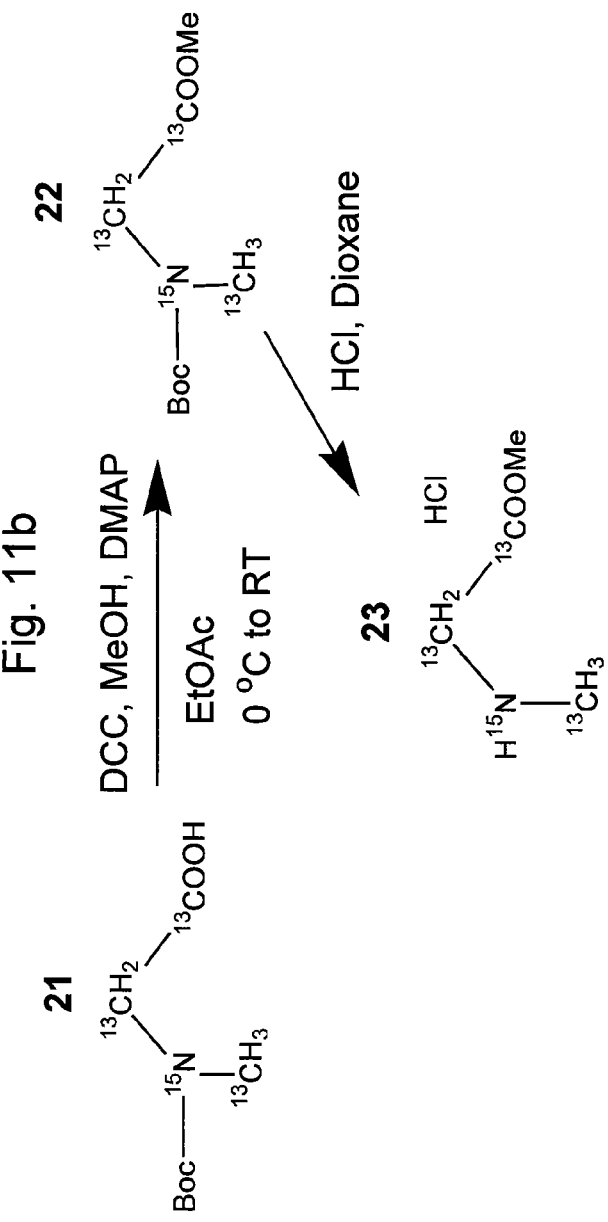
FIG. 11b is an illustration of one possible synthetic route to an encoded sarcosine derivative that can be used in the preparation of encoded N-methyl-piperazine derivatives.

With reference to FIGS. 11*a*, 11*b* and Examples 8 to 9, methods for the preparation of various encoded versions of N-methyl-glycine (i.e. sarcosine) are illustrated and described by adaptation of known synthetic reactions. For example, these encoded materials can be used in the preparation of encoded N-methyl piperazine acetic acid moieties used in reporters as described in various United States Published Patent Applications referenced in FIGS. 9*a-c* and 10*a-c*. It should therefore be apparent that these illustrations and Examples may be useful in the preparation of various encoded labeling reagents described herein from simple encoded materials that are commercially available.

With reference to FIGS. 12*a*, 12*b*, 12*c*, 28*a* and 29*a* various methods for the preparation of various encoded versions of N-methyl-ethylenediamine are illustrated by adaptation of known synthetic reactions. It should therefore be apparent that these illustrations may be useful in the preparation of various encoded labeling reagents described herein from simple encoded materials that are commercially available. For example, with reference to FIG. 12*c*, it is anticipated that the procedures described in Michel et al., *Structural study of bonding in thioamides. Synthesis and conformation of thioalanines and thioglycines. Canadian Journal of Chemistry*, 67(8): 1312-1318 (1989) can be used as a general guide to performing Step 1 of the illustrated reaction. Additionally, it is anticipated that the product literature provided by Callery Chemical (a BASF Company, Florham Park, N.J., USA) for Borane-Tetrahydrofuran Complex (and the references disclosed therein such as Amedia et al., *Syn. Comm.* 29: 2377 (1999)) can be used as a general guide to performing Step 2 of the illustrated reaction.

EXAMPLES

Aspects of the present teachings can be further understood in light of the following examples, which should not be construed as limiting the scope of the present teachings in any way.

Example 1

Synthesis of N-[2-(tert-Butoxycarbonyl-methyl-amino)-ethyl]-succinamic acid (103) (Step 1—FIG. 7*a*)

To a well stirred solution of N-(tert-Butoxycarbonyl)-N-methyl-ethylenediamine 101 (5.5 g, 0.032 mol) in dichloromethane ($CH_2Cl_2$, 30 mL) was added succinic anhydride 102 (3.2 g, 0.032 mol) in one portion. After stirring the reaction mixture for 1 hour at room temperature, a slurry resulted. This slurry was used in Step 2 without further work-up.

Note: If available, use of N-(9H-Fluoren-9-ylmethoxycarbonyl)-N-methyl-ethylenediamine would eliminate the need to perform Step 2. For this reason, FIGS. 9*a-c* suggest use of the Fmoc protected N-methyl ethylene diamine.

Example 2

Synthesis of N-{2-[(9H-Fluoren-9-ylmethoxycarbonyl)-methyl-amino]-ethyl}-succinamic acid (104) (Step 2—FIG. 7*a*)

To the slurry of compound 103 produced from Step 1 was added 20 mL of 80% trifluoroacetic acid (TFA) in $CH_2Cl_2$. The reaction mixture was then stirred at room temperature with thin layer chromatography (TLC) monitoring. After 2 hours, a TLC of the mixture indicated the complete disappearance of the starting material with the formation of a polar product. Excess solvent and TFA was then removed in a rotavapor and the residue was co-evaporated with tetrahydrofuran (THF, 30 mL×3). The remaining oily residue was then redissolved in acetone (50 mL), and the pH was made basic by carefully adding $NaHCO_3$ (aq.) solution. A solution of N-(9-Fluorenylmethoxycarbonyl-oxy)succinimide (Fmoc-Osu, 13.5 g, 0.0399 mol) in acetone (70 mL) was then added in one portion. The reaction mixture was then stirred at room temperature overnight. A TLC at this point confirmed the consumption of the starting material. Acetone/water was then removed in a rotavapor and the residue was diluted with water (50 mL) and washed with diethyl ether ($Et_2O$, 30 mL×3) in order to remove the nonpolar impurities. The aqueous layer was then acidified with 2 N HCl to a pH of ~2 and extracted with ethyl acetate (EtOAc, 100 mL×3). The combined organic portion was then washed with water (30 mL×4), brine (1×30 mL) and dried with sodium sulfate ($Na_2SO_4$). EtOAc was then removed in a rotavapor and the residue was kept under high vacuum overnight to furnish N-{2-[(9H-Fluoren-9-ylmethoxycarbonyl)-methyl-amino]-ethyl}-succinamic acid 104, as a hygroscopic white solid (10.5 g, 82%). MS: 397.2 (MH+)

Example 3

Synthesis of Support Bound N-{2-[(9H-Fluoren-9-ylmethoxycarbonyl)-methyl-amino]-ethyl}-succinamic acid (105) (Step 3—FIG. 7*a*)

To a solution of N-{2-[(9H-Fluoren-9-ylmethoxycarbonyl)-methyl-amino]-ethyl}-succinamic acid (104) (595 mg, 1.5 mmol) in $CH_2Cl_2$ was added (10 mL) of N,N-diisopropylethylamine (DIPEA, 776 mg, 6 mmol) followed by trityl chloride support (1 g, 1 mmol, P/N SC5028, Advanced Chemtech). The slurry was then agitated for 1.5 hour at room temperature and then washed with a solution of $CH_2Cl_2$/MeOH/DIPEA (17:2:1, 3×10 mL), $CH_2Cl_2$ (3×10 mL), N—N-dimethylformamide (DMF, 2×10 mL) and finally again with $CH_2Cl_2$ (2×10 mL). The loaded support (105) was dried under vacuum and a sample was analyzed for Fmoc-loading. The average loading was 0.5 mmol/g. This support was used in Step 4 without further workup.

Example 4

Synthesis of Support Bound N-(2-Methylamino-ethyl)-succinamic acid (106) (Step 4—FIG. 7*b*)

The support bound N-(Fmoc)-N-methyl ethylenediamine succinate (105) was treated with 20% piperidine/DMF (10 mL—applied and then allowed to drain). An additional amount of 20% piperidine/DMF (10 mL) was then added and the slurry was agitated for 10 minutes. The support was then washed with DMF (10 mL×2), $CH_2Cl_2$ (10 mL×2) and finally with DMF (10 mL×2). The deprotected support (106) was then immediately used in Step 5.

Example 5

Synthesis of Support Bound N-(2-{(Methyl-[2-(4-methyl-piperazin-1-yl)-acetyl]-amino}-ethyl)-succinamic acid (108) (Step 5—FIG. 7*b*)

(4-Methyl-piperazin-1-yl)-acetic acid bis trifluoroacetate 107 (965 mg, 2.5 mmol) was dissolved in anhydrous DMF (8 mL) and DIPEA (646 mg, 5 mmol). To this solution was added O-(7-azabenzotriazol-1-yl)-N,N, N',N'-tetramethyluronium hexafluorophosphate (HATU, 950 mg, 2.5 mmol). The mixture was vortexed for 1 minute and the support (106) was added to it. The slurry was agitated for 25 minutes, filtered, washed with DMF (10 mL×3), $CH_2Cl_2$ (10 mL×2) and DMF (10 mL×2). The support was then subjected to a second round of coupling (i.e. double coupling) using the same equivalents of reagents and then washed with DMF (10 mL×3) and $CH_2Cl_2$ (10 mL×3). The support (108) was then dried under vacuum and used in Step 6 without further workup.

Example 6

Synthesis of N-(2-{Methyl-[2-(4-methyl-piperazin-1-yl)-acetyl]-amino}-ethyl)-succinamic acid (109) (Step 6—FIG. 7*c*)

The support (108) was treated with TFA/$CH_2Cl_2$ (10 mL) and allowed to stand for 5 minutes. The solvent was then drained from the support and the support was again treated with TFA/$CH_2Cl_2$ (15 mL) and the solvent collected. Both portions of TFA/$CH_2Cl_2$ were mixed and then concentrated in a rotavapor. The residue was co-evaporated with THF (20 mL×3). Traces of TFA were removed under high vacuum. The residue was then triturated with anhydrous ether. A gummy mass resulted. This product was left under vigorous stirring using a stir bar overnight. The resulted white solid was separated by centrifugation, washed with ether (5 mL×3), and dried under high vacuum to furnish 109 as a white hygroscopic solid (320 mg, 59% overall yield). MS: 315 (MH+)

Example 7

Synthesis of the NHS Ester of N-(2-{Methyl-[2-(4-methyl-piperazin-1-yl)-acetyl]-amino}-ethyl)-succinamic acid (111) (Step 7—FIG. 7*c*)

To a solution of 109 (100 mg, 0.18 mmol) in anhydrous THF (2 mL) was added N-hydroxysuccinimidyl-trifluoroacetate 110 (48 mg, 0.22 mmol). The reaction mixture was stirred at room temperature for 2 hours. The THF was removed under rotavapor and traces of TFA were removed by coevaporation with additional THF (2 mL×2). The gummy residue was then allowed to stand on anhydrous ether overnight in a refrigerator. Ether was decanted out and the residue was kept under high vacuum to furnish 111 as a foam (110 mg, 93%). MS: 412 (MH+).

Example 8

Synthesis of Encoded N-(t-boc)-Sarcosine (21) (See: FIG. 11*a*)

Dry THF (100 mL) was transferred via cannula to a nitrogen flushed 500 mL round bottom flask containing Boc-$^{15}NH$-$^{13}CH_2$—$^{13}COOH$ (7 g, 39.29 mmol, 1 eqv., Cambridge Isotope Lab, P/N: CNLM-2412-0) and magnetic stirbar. The mixture was stirred at room temperature until a clear solution was obtained. The solution was then cooled to 0° C. using an ice bath. A septa attached graduated cylinder was flushed with nitrogen and potassium tert-butoxide (t-BuOK, 157 mL, 1 M in THF, 4 eqv.) solution was transferred to it. The t-BuOK solution was then added to the reaction mixture, while stirring at 0° C., using a cannula and pressure difference. Initially a gel formed which dissolved within approximately a minute. The reaction was stirred for another 10 minutes at 0° C.

Ampoules of $^{13}CH_3I$ (2×10 g, 140 mmol, 3.56 eqv., Cambridge Isotope Lab, P/N: CLM-287-10) were cooled in refrigerator ($^{13}CH_3I$ is highly volatile and should be opened only if cold) and opened under a blanket of nitrogen. The content was quickly transferred to the reaction mixture via a cannula. The reaction mixture then stirred vigorously for 1 hour at 0° C. A small aliquot (100 µL) of the reaction was treated with water (1 mL), acidified to pH 1 by the addition of 1 M HCl and extracted with EtOAc (2 mL). TLC analysis of the EtOAc layer showed that the reaction is complete ($R_f$ 20=0.51, $R_f$ 21=0.70; 1:4 MeOH—$CH_2Cl_2$—AcOH (10 µL/10 mL); TLC developed by heating with 3% (w/v) ninhydrin solution in ethanol (EtOH)).

The THF solvent was then removed under reduced pressure, the solid was dissolved in 100 mL water and then acidified with 1 M HCl to pH=1. The aqueous medium was extracted with EtOAc (300 mL×2). Combined EtOAc layers were treated with 2% (w/v) $NaHSO_3$ (50 mL)+brine (50 mL) solution and mixed vigorously to remove any 12 formed during the workup. EtOAc layer washed further with brine (50 mL) and dried over $Na_2SO_4$. EtOAc and any tert-butyl alcohol (t-BuOH) was then removed under reduced pressure to give compound 21 as thick colorless oil or low melting solid (7.42 g, 97% yield). ES-MS (Direct infusion in methanol (MeOH)) Calculated MNa+ ($C_5^{13}C_3H_{15}^{15}NO_4Na$)= 216.10, observed MNa+=216.10.

Example 9

Synthesis of Encoded Sarcosine Methyl Ester (23) (See FIG. 11*b*)

Boc-$^{15}N^{13}CH_3$—$^{13}CH_2$—$^{13}COOH$ (21, 7.42 g, 38.41 mmol), dimethylaminopyridine (DMAP, 470 mg, 3.41 mmol) and MeOH (7.8 mL, 5×38.41 mmol) were dissolved in EtOAc (200 mL) and cooled to 0° C. Dicyclohexylcarbodiimide (DCC, 8.32 g, 1.05×38.41 mmol) dissolved in EtOAc (30 mL) was then added to the reaction mixture. The reaction mixture was then stirred overnight while gradually warming up to RT. TLC analysis showed that the reaction was complete ($R_f$ 21=0.00, $R_f$ 22=0.50; 7:3 hexanes-EtOAc; TLC developed by heating with 3% (w/v) ninhydrin solution in EtOH). Dicyclohexylurea (DCU) precipitate was removed by filtration (Whatman #2 filter paper) and the filtrate concentrated to 50 mL. The concentrated solution was adsorbed in $SiO_2$-gel and purified by flash-chromatography (two runs; 120 g $SiO_2$ column Isco.; 85 mL/min, 0-5 min 10% EtOAc in hexanes, 5-20 min 25% EtOAc in hexanes).

Fractions containing the pure product 22 were combined and concentrated to 50 mL using a rotary evaporator at RT (b.p. of compound 22 is low and should not be subjected to high vacuum). To the concentrated solution, HCl solution was added (60 mL, 4 M HCl in dioxane) and stirred. Vigorous gas evolution was observed. After 30 min, TLC analysis showed complete t-Boc deprotection ($R_f$ 23=0.00, $R_f$ 22=0.50; 7:3 hexanes-EtOAc; TLC was developed by heating with 3% (w/v) ninhydrin solution in EtOH). Volatiles were removed under reduced pressure to give compound 23 as white hygroscopic solid (5.2 g, 94% yield over two steps). ES-MS (Direct infusion in MeOH) Calculated for 4 $MH^+$ ($C^{13}C_3H_{10}^{15}NO_2$)=108.09, observed MH+=108.08, calculated $M_2H^+$=215.18, observed $M_2H^+$=215.17.

Example 10

Synthesis of Support Bound [Glu¹]-Fibrinopeptide B Human

[Glu¹]-Fibrinopeptide B human [Glu-Fib, CAS#: 103213-49-6]: The peptide was assembled manually on trityl chloride resin (P/N: Novabiochem, 01-64-0074) using standard Fmoc-peptide synthesis protocol (Novabiochem catalog, 2004-2005) and the following amino acid derivatives: Fmoc-Arg (Pbf)-OH (P/N: Novabiochem, 04-12-1145), Fmoc-Glu (O'Bu)-OH (P/N: Novabiochem, 04-12-1020), Fmoc-Gly-OH (P/N: Novabiochem, 04-12-1001), Fmoc-Val-OH (P/N: Novabiochem, 04-12-1039), Fmoc-Asn(Trt)-OH (P/N: Novabiochem, 04-12-1089), Fmoc-Asp(Mpe)-OH (P/N: Bachem, B-3560), Fmoc-Phe-OH (P/N: Novabiochem, 04-12-1030), Fmoc-Ser(tBu)-OH (P/N: Novabiochem, 04-12-1033), Fmoc-Ala-OH (P/N: Novabiochem, 04-12-1006). Amino acid sequence of [Glu1]-Fibinopeptide B human: Seq ID. No. 1: Glu-Gly-Val-Asn-Asp-Asn-Glu-Glu-Gly-Phe-Phe-Ser-Ala-Arg.

Example 11

Synthesis of Fmoc-N(Me)-CH₂CH₂—N(Me)-CO—CH₂CH₂—COOH

A solution of NH(Me)-CH₂CH₂—NH(Me) (1.6 mL, 15 mmol, P/N: Alfa-Aesar, USLF006653,) in THF (15 mL) was added to trityl-chloride resin (P/N: Novabiochem, 01-64-0074, 1 g, 1.5 mmol) and the suspension was agitated for 1 h at ambient temperature. The resin was then filtered and washed with N-Methyl-2-pyrrolidinone (NMP, 15 mL×3), treated with MeOH-DMF-Diisopropylethylamine (DIPEA, 15 mL, 4:7:2 v/v, P/N: Aldrich, 387649,) for 15 min. The resin was finally filtered and washed with NMP (15 mL×3).

Succinic anhydride (P/N: Aldrich, 2399690, 1.5 g, 15 mmol) dissolved in DMF (10 mL) was then added to the resin followed by DIPEA (2.61 mL, 15 mmol), The resin was then agitated for 20 min at ambient temperature. The resin was then filtered and washed with NMP (15 ml×3) followed by acetonitrile (CH₃CN, 15×3 mL).

The resin was treated with TFA-DCM (20% v/v, 40 mL), filtered, and washed with additional TFA-DCM (20% v/v, 10 mL×5). The filtrate was concentrated under reduced pressure to an oily residue (TFA N(Me)-CH₂CH₂—N(Me)-CO—CH₂CH₂—COOH, 1.07 g), which was dissolved in saturated NaHCO₃ (pH 8-9). A solution of Fmoc-OSu (P/N: Advance ChemTech RC8015, 1.43 g, 4.24 mmol in acetone (20 mL)) was then added to the aqueous solution and stirred for 2 hours at ambient temperature. TLC analysis showed formation of a product ($R_f$=0.50; 9:1:0.01 DCM-MeOH—AcOH, UV 254 nm, TLC developed by heating with 3% (w/v) solution of ninhydrin in ethanol (EtOH)). The reaction mixture was then concentrated to remove acetone and the residue was then diluted with water (150 mL). Non-polar impurities were removed by extraction with Et₂O (100 mL×2). The aqueous layer was acidified (pH ~1, HCl, 1 M) and extracted with EtOAc (100 mL×2). The combined EtOAc layer was dried over Na₂SO₄ and concentrated to give 0.95 g of Fmoc-N(Me)-CH₂CH₂—N(Me)-CO—CH₂CH₂—COOH as colorless viscous oil. ES-MS (MeOH-direct infusion) Calculated $MH^+$ ($C_{22}H_{24}N_2O_5H^+$)=397.17, Observed $MH^+$ 397.16.

Example 12

Synthesis of Fmoc-NH—CH₂CH₂—NH—CO—CH₂CH₂—COOH. DIPEA

Fmoc-NH—CH₂CH₂—NH₂.HCl (P/N: Novabiochem, 01-63-0064, 1 equivalent (eqv.)) was reacted with succinic anhydride (1 eqv.) in presence of DIPEA (1 eqv.) in DCM to give the title compound.

Example 13

Synthesis of Fmoc-NH—CH₂CH₂—N(Me)-CO—CH₂CH₂—COOH

To a well stirred solution of Boc-NMe-CH₂CH₂—NH₂ (265 mg, 1.52 mmol) in acetone (15 mL) was added a solution of Fmoc-OSu (564 mg, 1.67 mmol in 15 mL acetone). The mixture was then stirred for 2 hours at ambient temperature. TLC analysis of the reaction mixture at this stage showed formation of Boc-NMe-CH₂CH₂—NH-Fmoc ($R_f$=0.35; 3:7 EtOAc:hexanes, UV 254 nm, TLC developed by heating with 3% (w/v) solution of ninhydrin in EtOH).

After evaporation of acetone the product was purified by flash-chromatography (40 g Isco-silica column, 40 mL/min, 254 nm, 3:7 EtOAc-hexanes, 18 mL fractions collected, fractions 15-24 had pure product) to give Boc-NMe-CH₂CH₂—NH-Fmoc as foam (520 mg, yield=86%).

Boc-NMe-CH₂CH₂—NH-Fmoc (520 mg, 1.31 mmol) was treated with TFA-water (15 ml, 95:5, v/v) for 1 hour at ambient temperature, when TLC analysis showed complete Boc-deprotection. TFA-water was removed under reduced pressure and the resulting oil dissolved in DCM (30 mL). To this solution, succinic anhydride (131 mg, 1.31 mmol) was added followed by DIPEA (to pH ~10 by moist pH paper). The mixture was then stirred for 30 min. The reaction mixture was then acidified (pH=1) with HCl (1 M) and extracted with EtOAc (100 mL×3). The combined EtOAc layers were washed with brine (100 mL×2) and dried over Na₂SO₄. The EtOAc was removed under reduced pressure to give the title compound as a colorless oil. ES-MS (MeOH-direct infusion) Calculated $MH^+$ ($C_{23}H_{26}N_2O_5H^+$)=411.10, Observed $MH^+$411.09.

Example 14

Synthesis of N-(Fmoc)-N'-succinyl-piperazine (FIG. 20)

To a solution of Boc-piperazine (P/N: Lancaster L13363, 500 mg, 2.68 mmol) in DCM (30 ml) was added succinic anhydride (269 mg, 2.68 mmol). The reaction was stirred for 2 hours at ambient temperature. TLC analysis showed formation of succinylated Boc-piperazine ($R_f$=0.50; 9:1:0.01 DCM-MeOH—AcOH, TLC developed by heating with 3% (w/v) solution of ninhydrin in EtOH). To this solution was added TFA (30 mL) and the mixture was then stirred for 1 h at ambient temperature. The volatile components of the mixture were removed under reduced pressure and the resulting oil dissolved in THF (30 mL) with minimum amount of water and adjustment of the pH to 9 by the addition of DIPEA. A solution of Fmoc-OSu (907 mg, 2.69 mmol) in THF (10 mL) was added and stirred for 1 h at ambient temperature. TLC analysis showed formation of a product ($R_f$=0.55; 9:1:0.01 DCM-MeOH—AcOH, UV 254 nm, TLC developed by heating with 3% (w/v) solution of ninhydrin in EtOH). The volatile components of the mixture were then removed under reduced pressure and the resulting oil was dissolved in minimum volume of saturated $NaHCO_3$. The aqueous solution was then extracted with $Et_2O$ (100 mL×2), acidified (pH ~1) with HCl (1 M) and re-extracted with EtOAc (150 mL×2). The combined EtOAc layers were dried over $Na_2SO_4$ and concentrated to give the product as colorless oil.

Example 15

Coupling of Succinylated Fmoc-Diamines and Piperazine Acetic Acid to Glu-Fib Peptide Approximately 10 mg of support bound [$Glu^1$]-Fibrinopeptide B human resin (See: Example 10) was treated with 20% (v/v) piperidine in DMF (2 mL×1 min, filtered, then 2 mL×5 min), filtered and washed (NMP). Succinylated Fmoc-diamines (or their DIPEA salts, as shown in the Examples 11-14 above [except for Fmoc-NH—$CH_2CH_2CH_2CH_2$—NH—CO—$CH_2CH_2$—COOH which was used to make compound 125 and which was available from in-house production of unrelated materials but which could be produced using methods disclosed herein], 10 eqv to Glu-Fib amount on the resin) were activated with HATU (P/N: Applied Biosystems 4317033, 9.5 eqv) and DIPEA (30 eqv) in NMP (~1 mL). The activated compounds were added to the resin and mixed for 30 min. The resin was then filtered, washed with NMP, and Fmoc group was removed by treatment with 20% (v/v) piperidine in DMF as discussed above. Piperazine acetic acid-TFA salt (10 eqv) was then activated using HATU (9.5 eqv) and DIPEA (60 eqv) in NMP (~1.5 mL). The solution of the activated compound was then added to the resin. After 30 minutes the resin washed with NMP followed by $CH_3CN$. Labeled peptides were then cleaved (and deprotected) from the resin using 95:5 TFA-water (200 μL, 2 hours) and precipitated using diethyl ether ($Et_2O$).

Data from MS analysis of the various labeled peptides (ES-MS, direct infusion in water)

Compound 120: (N-Methyl-piperazine)acetyl-N(Me)—$CH_2CH_2$—N(Me)-CO—$CH_2CH_2$—CO-Glu-Fib: Calculated $MH^+$=1880.9, Observed $MH^+$=1880.3
Compound 121: (N-Methyl-piperazine)acetyl—NH—$CH_2CH_2$—NH—CO—$CH_2CH_2$—CO-Glu-Fib: Calculated $MH^+$=1853.8, Observed $MH^+$=1853.8
Compound 122: (N-Methyl-piperazine)acetyl—NH—$CH_2CH_2$—N(Me)-CO—$CH_2CH_2$—CO-Glu-Fib: Calculated $MH^+$=1867.9, Observed $MH^+$=1867.9
Compound 123: (N-Methyl-piperazine)acetyl-N(Me)-$CH_2CH_2$—NH—CO—$CH_2CH_2$—CO-Glu-Fib: Calculated $MH^+$=1867.9, Observed $MH^+$=1867.9
Compound 124: (N-Methyl-piperazine)acetyl-piperazine-CO—$CH_2CH_2$—CO-Glu-Fib: Calculated $MH^+$=1879.9, Observed $MH^+$=1879.0
Compound 125: (N-Methyl-piperazine)acetyl-NH—$CH_2CH_2CH_2CH_2$—NH—CO—$CH_2CH_2$—CO-Glu-Fib: Calculated $MH^+$=1880.90, Observed $MH^+$=1880.94.

Example 16

Discussion of FIGS. 22a, 22b, 23a, 23b, 24a and 24b

Figure 22A:
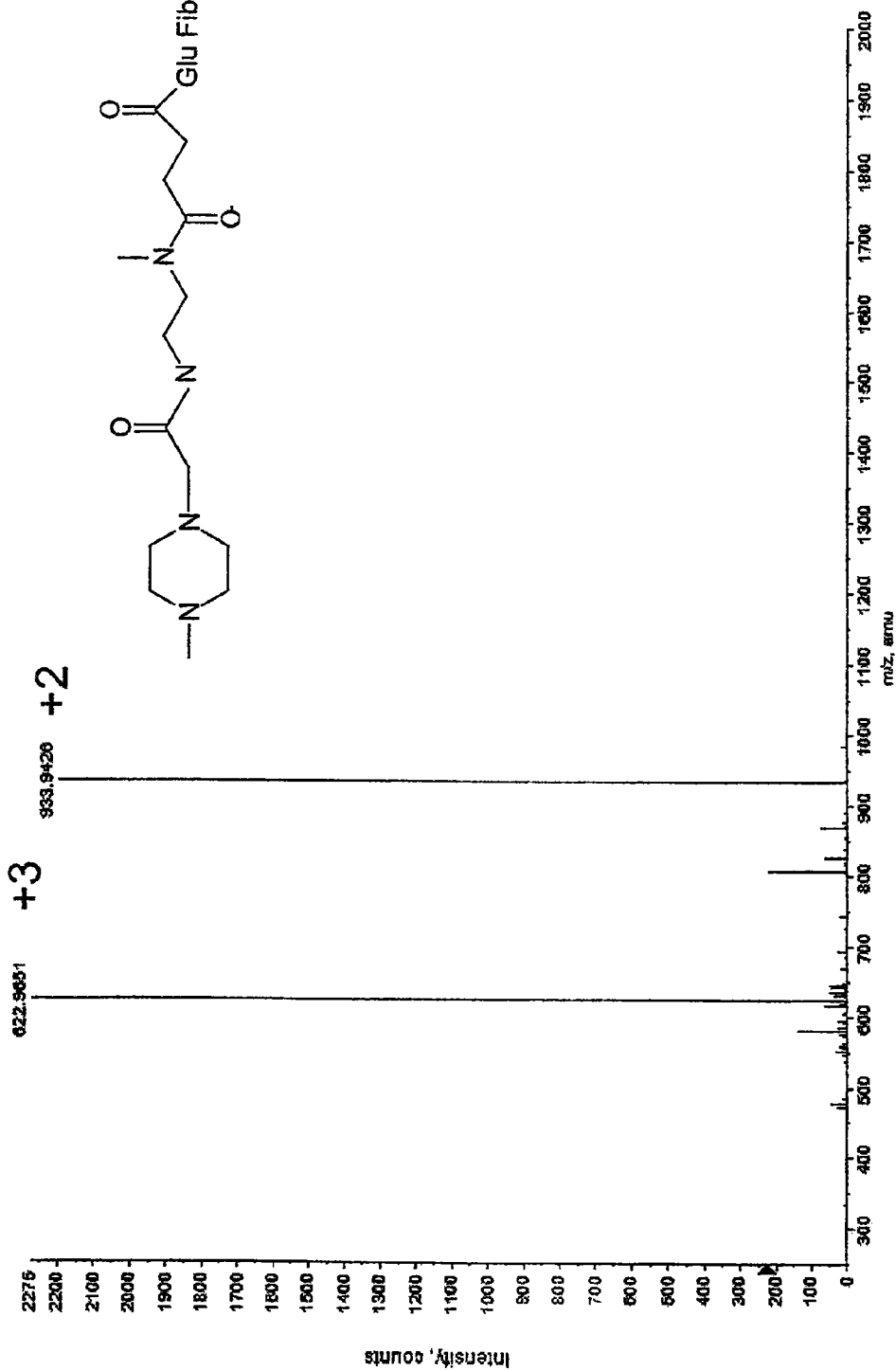
FIG. 22a is a plot of MS data for a peptide ([Glu1]-Fibinopeptide B human) labeled with an uncoded version of an exemplary labeling reagent described herein.
Figure 22B:
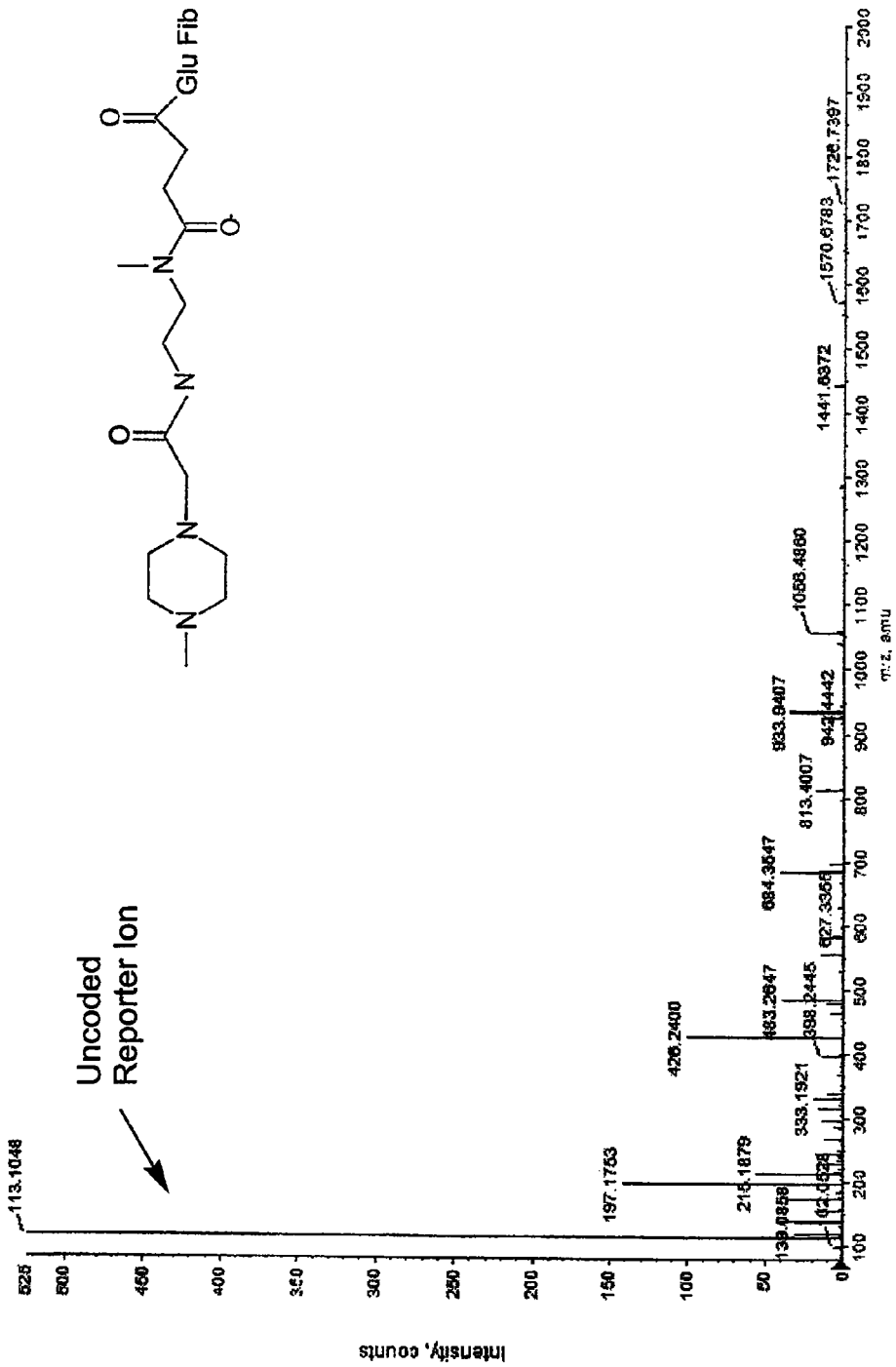
FIG. 22b is a plot of MS/MS data for a selected peak of the labeled peptide illustrated in FIG. 22a that was subject to CID fragmentation and reanalysis of the fragments.

FIG. 22a is the plot for MS analysis of compound 122. Strong peaks are observed for ions having charges of +2 and +3 for the labeled peptide. FIG. 22b is the plot for MS/MS analysis of the selection and fragmentation of the +2 peak observed in FIG. 22a. In addition to daughter fragment ions of the peptide, a strong signal for the uncoded reporter ion is observed at m/z of 113.10. This data suggests that encoded labeling reagents of the same general structure will fragment to produce reporter ions of unique mass that can be used in multiplex analysis of analytes.

Figure 23A:
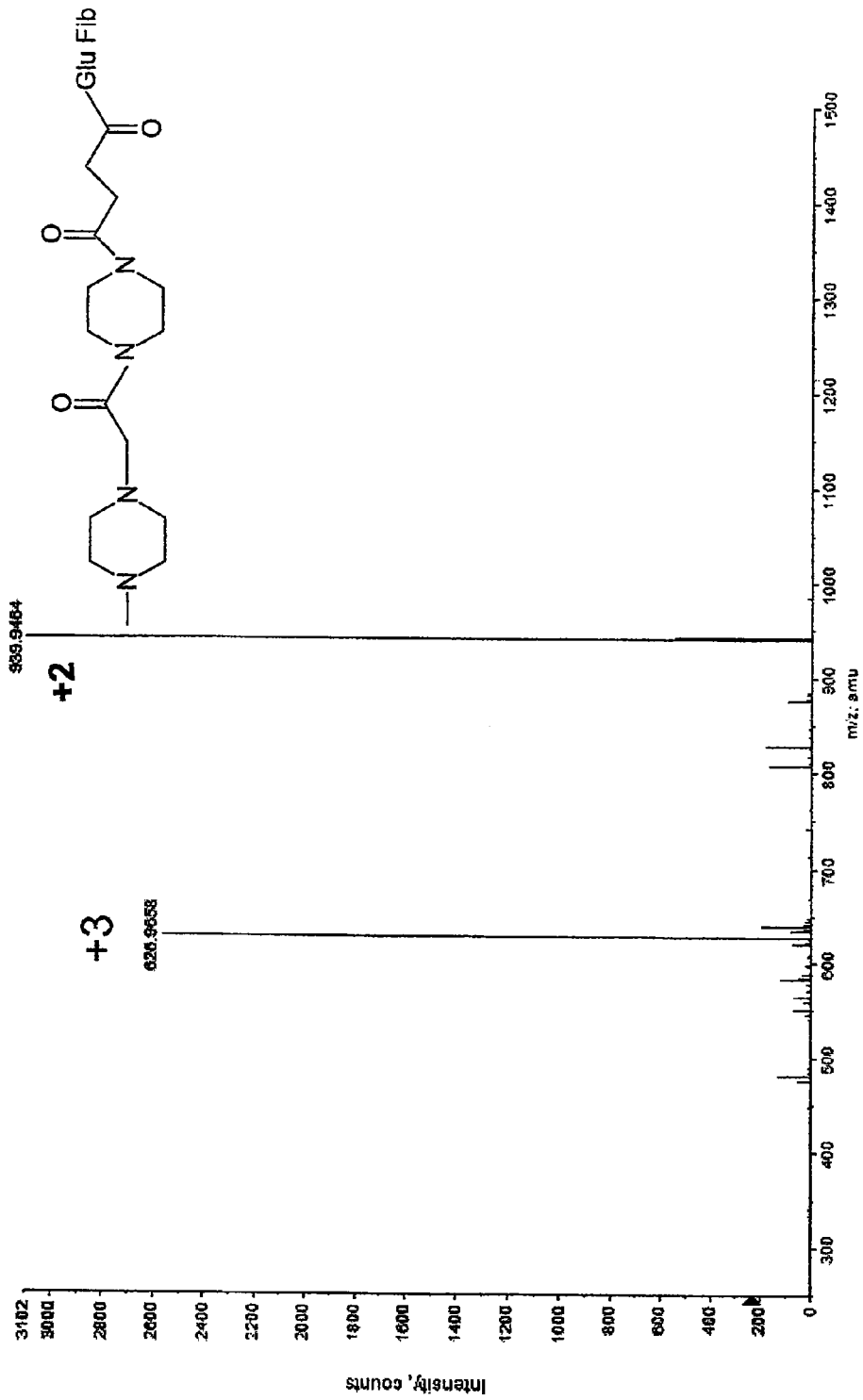
FIG. 23a is a plot of MS data for a peptide ([Glu1]-Fibinopeptide B human) labeled with an uncoded version of an exemplary labeling reagent described herein.
Figure 23B:
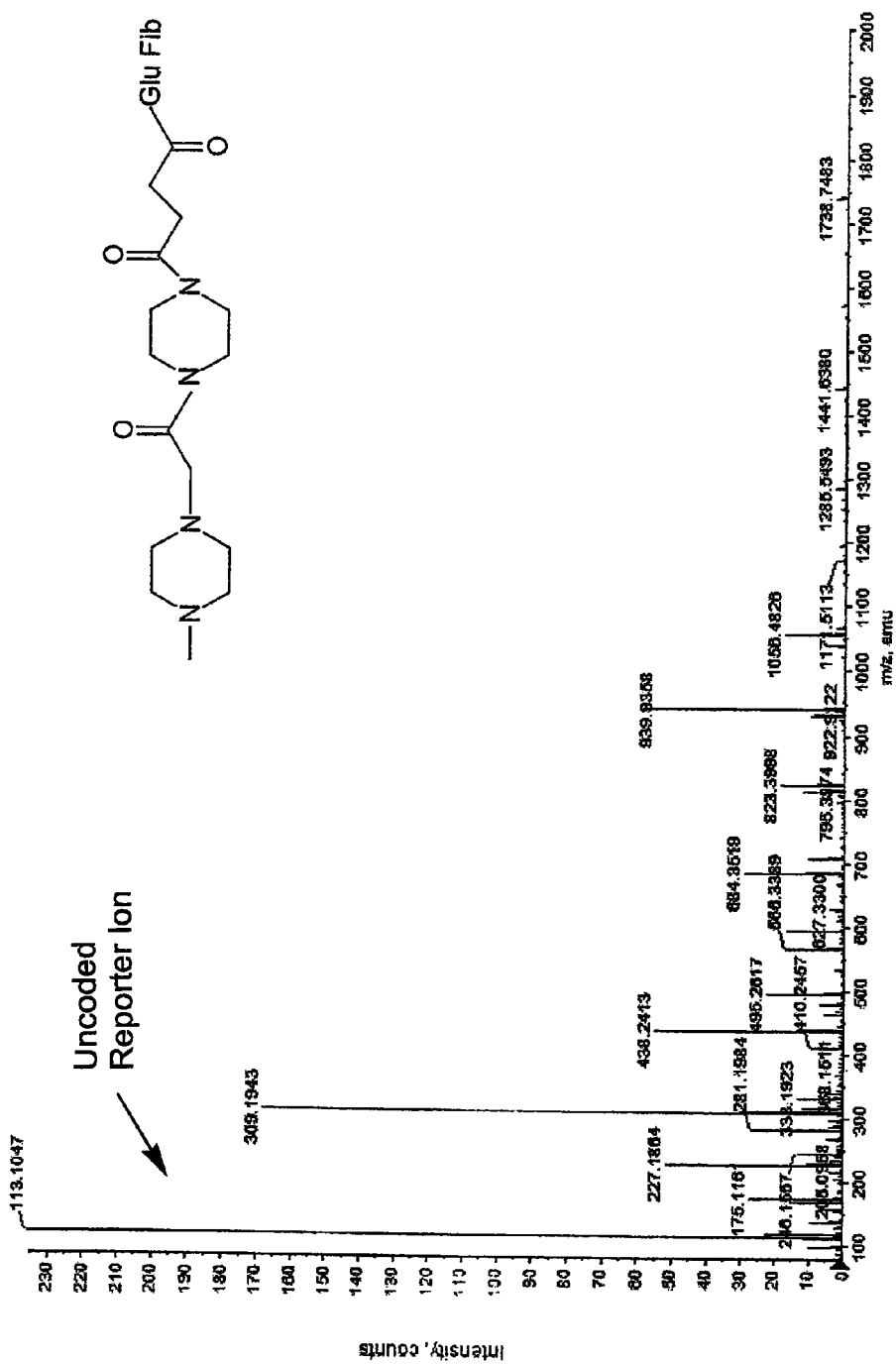
FIG. 23b is a plot of MS/MS data for a selected peak of the labeled peptide illustrated in FIG. 23a that was subject to CID fragmentation and reanalysis of the fragments.

FIG. 23a is the plot for MS analysis of compound 124. Strong peaks are observed for ions having charges of +2 and +3 for the labeled peptide. FIG. 23b is the plot for MS/MS analysis of the selection and fragmentation of the +2 peak observed in FIG. 23a. In addition to daughter fragment ions of the peptide, a strong signal for the uncoded reporter ion is observed at m/z of 113.10. This data suggests that encoded labeling reagents of the same general structure will fragment to produce reporter ions of unique mass that can be used in multiplex analysis of analytes.

Figure 24A:
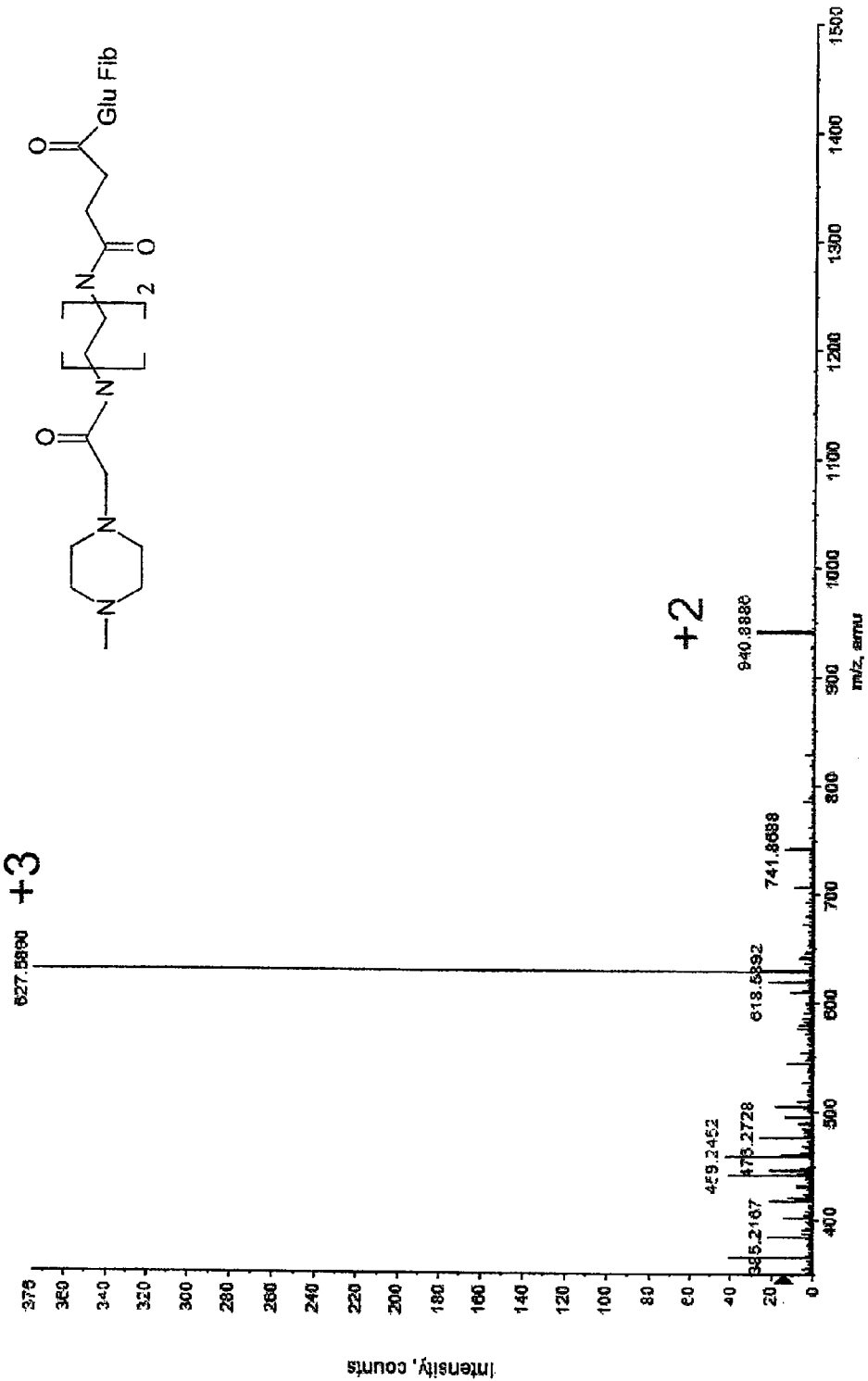
FIG. 24a is a plot of MS data for a peptide ([Glu1]-Fibinopeptide B human) labeled with an uncoded version of an exemplary labeling reagent described herein.
Figure 24B:
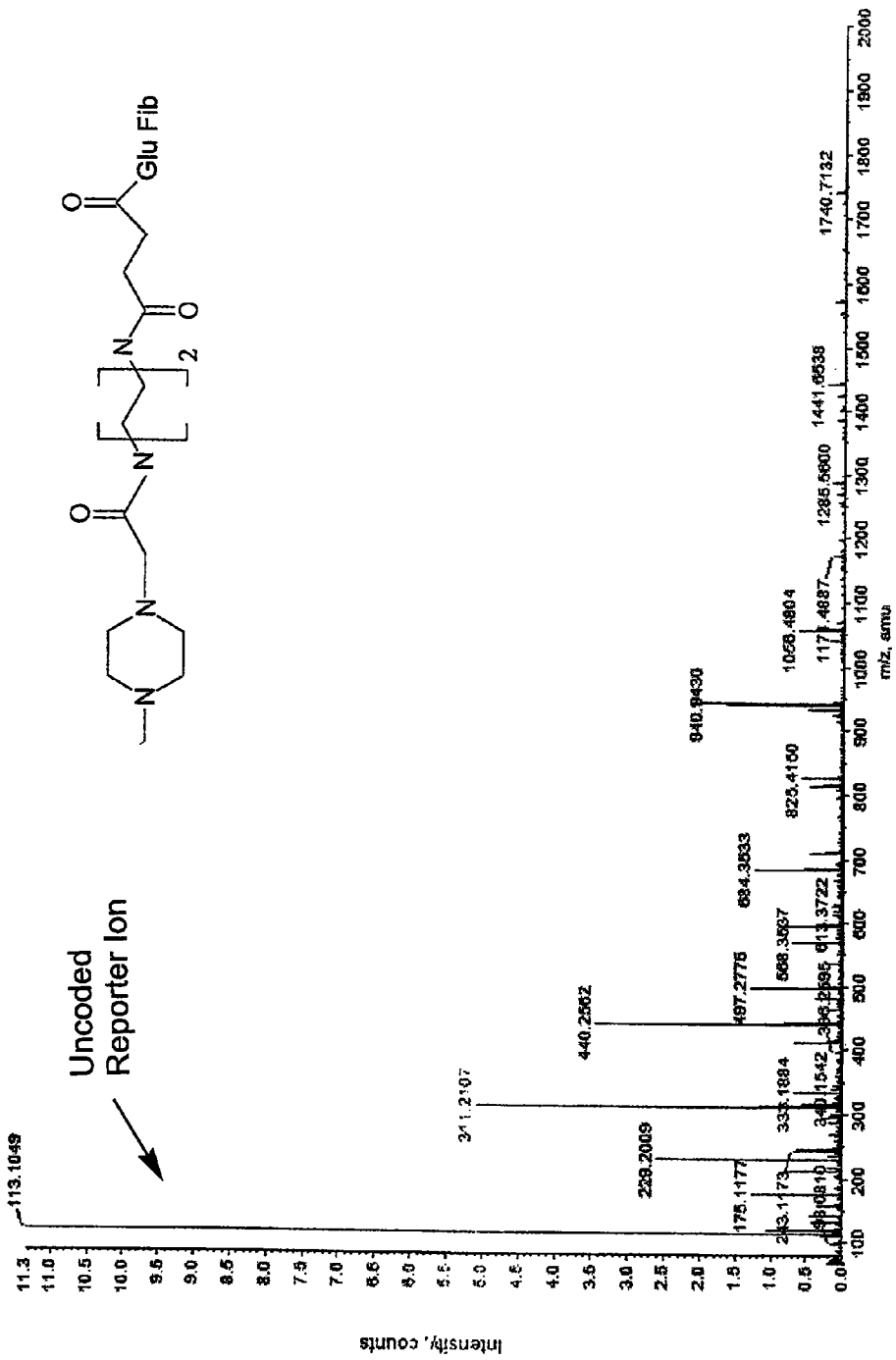
FIG. 24b is a plot of MS/MS data for a selected peak of the labeled peptide illustrated in FIG. 24a that was subject to CID fragmentation and reanalysis of the fragments.

FIG. 24a is the plot for MS analysis of compound 125. Peaks are observed for ions having charges of +2 and +3 for the labeled peptide. FIG. 23b is the plot for MS/MS analysis of the selection and fragmentation of the +2 peak observed in FIG. 24a. In addition to daughter fragment ions of the peptide, a strong signal for the uncoded reporter ion is observed at m/z of 113.10. This data suggests that encoded labeling reagents of the same general structure will fragment to produce reporter ions of unique mass that can be used in multiplex analysis of analytes.

Compounds 120, 121 and 123 also exhibited characteristics under MS and MS/MS analysis similar to those observed with compounds 122, 124 and 125. In all cases, reporter ions and daughter fragment ions were observed. The data therefore suggests that encoded labeling reagents of the same general structure will fragment to produce reporter ions of unique mass that can be used in multiplex analysis of analytes.

Example 17

Figure 28A:
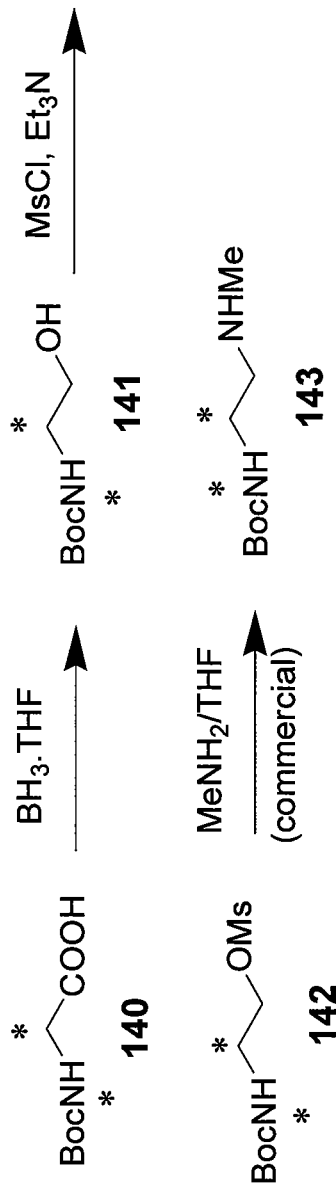
FIG. 28a is an illustration of one possible synthetic route to an encoded N-methyl ethylene diamine comprising two isotopically encoded sites.
Figure 28B:
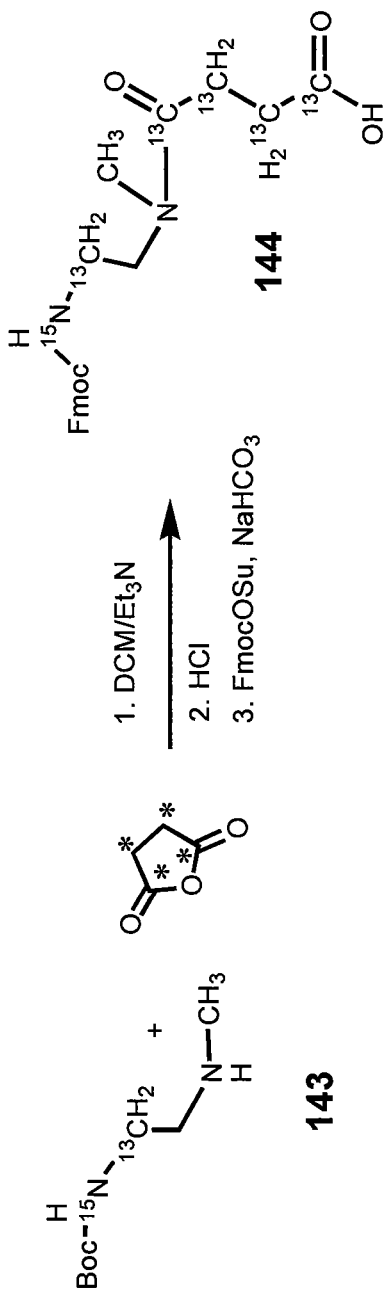
FIG. 28b is an illustration of the synthesis of Fmoc-NH—$CH_2CH_2$—N(Me)-CO—$CH_2CH_2$—COOH comprising six isotopically encoded sites.

Synthesis of Encoded N-(t-boc)-aminoethanol (FIG. 28a)

Step 1 (FIG. 28a):

To the ice-cooled solution of N-Boc-Sarcosine ($C_3$, $^{15}N$) 140 (10 g, 51.7 mmol) in anhydrous THF (200 mL), 1 M solution of $BH_3$. THF in THF (15.56 g, 181 mL, 181 mmol) was added dropwise using a cannula under argon pressure. Initially, the rate of addition was controlled to maintain a moderate effervescence. Once the effervescence stopped, the rate of addition was increased. After the addition, the mixture was stirred at 0° C. for about 1.5 hr. The completion of the reaction was confirmed by TLC analysis. The reaction was then quenched by the careful addition of methanol at 0° C. The reaction mixture was concentrated in a rotavap. The oily residue was then co-evaporated with an additional quantity of methanol (500 mL). The resulted oily residue was purified by flash chromatography using Combi-flash instrument to afford 8 g (90%) of N-Boc-N-Me-aminoethanol($^{13}$C, $^{15}$N) 141 as a colorless oil. MS (178, M+H)

Step 2, (FIG. 28a):

To an ice cold solution of 141 (7.8 g, 48 mmol), Et$_3$N (16.7 mL, 120 mmol) in DCM (700 mL) MsCI (P/N: Fluka 64260, 4.5 mL, 57.6 mmol) was added over 4 min while stirring. After another 15 min at 0° C. the reaction mixture was analyzed by TLC and showed formation of a new product (R$_f$2=0.20, R$_f$3=0.42; 1:1 hexanes-EtOAc; TLC developed by heating with 3% (w/v) ninhydrin solution in EtOH).

DCM evaporated and the yellow solid was dissolved in EtOAc (1.5 L). The EtOAc layer washed with HCl (1 M, 800 mL), followed by brine (400 mL×2), dried over Na$_2$SO$_4$ and concentrated to give yellow oil. The oil was purified by column chromatography (120 g SiO$_2$ column Isco (×2).; 40 mL/min, 0-5 min 35% EtOAc in hexanes, 5-15 min 40% EtOAc in hexanes. 18 mL-fractions collected; fractions 9-24 had pure product) to give Boc*NH*CH$_2$CH$_2$OMS 142 as colorless oil, which was immediately used for the next step (~11.5 g)

Step 3; FIG. 28a

Compound 142 (48 mmol, assuming 100% yield from previous reaction) was transferred to a Chem-Glass pressure vessel using minimum amount of THF (~60 ml) to which 500 mL of 2M solution of methyl amine ((P/N: Aldrich 395056, 31 g, 1000 mmol) was added, capped and heated (while stirring) at 40-45° C. for overnight (use safety shield). TLC analysis (1:1 EtOAc-hexanes) showed complete consumption of 142 and formation of a new product (R$_f$4=0.52; 1:1 DCM-MeOH+1% (v/v) Et$_3$N; TLC plate was heated first for 5 min to remove Et$_3$N then developed by heating with 3% (w/v) ninhydrin solution in EtOH). Reaction mixture was then concentrated in a rotavaopr and the residue was dissolved in methylene chloride (1.5 L) and transferred to a separatory funnel. 1 N NaOH (200 mL) and brine (200 mL) were added and extracted. The organic layer was further washed with 1 N NaOH (200 mL) and brine (200 mL). Dried over Na$_2$SO$_4$. The residue was purified by Combi Flash to afford 143 as a colorless oil (6.45 g, 76%). MS (177 M+H).

Example 18

Synthesis of Fmoc-NH—CH$_2$CH$_2$—N(Me)-CO—CH$_2$CH$_2$—COOH Comprising Six Isotopically Encoded Sites (FIG. 28b):

To a stirred solution of 143 (6.4 g, 36.5 mmol) in acetone (200 mL) succinic anhydride-$^{13}$C$_4$ (3.8 g. 36.5 mmol) was added in one shot. Triethyl amine (5 mL, 36.5 mmol) was then added dropwise and the reaction mixture was stirred at RT for 30 min. A TLC at this point confirmed the complete disappearance of the starting material. The reaction mixture was concentrated in a rotavapor and the residue was dissolved in methylene chloride (100 mL). 140 mL of 4M solution of HCl in dioxane was then added. A white precipitate was formed in 5 min. The supernatant was analyzed by TLC to confirm the complete disappearance of the starting material. The reaction mixture was concentrated in a rotavapor and the white solid residue was dissolved in saturated NaHCO$_3$ solution (pH 8-9). A solution of Fmoc-Osu (14.5 g, 43 mmol) in acetone (400 mL) was then added to the above solution and stirred at RT for 3 hr. A TLC at this point indicated the completion of the reaction. Reaction mixture was then concentrated in a rotavapor and the solid residue was transferred to a separatory flask using ether (200 mL) and water (200 mL). Ether layer was separated and the aqueous layer was extracted with ether (200 mL×3). The ether solution was then acidified with 6 M HCl to pH 2 and extracted with EtOAc (4×200 mL). The combined EtOAc extracts washed with brine (50 mL×3) and dried over Na$_2$SO$_4$. EtOAc was evaporated in a rotavapor to get a foam which on keeping at high vacuum afforded 144 as a white solid in 95% yield. MS (403, M=H)

Example 19

Synthesis of Encoded N-(Fmoc)-N'-(methyl)-ethylenediamine-HCl (FIG. 29a)

Step 1 (FIG. 29a):

To the ice-cooled solution of N-Boc-Sarcosine($^{13}$C$_3$, $^{15}$N) 150 (10 g, 51.7 mmol) in anhydrous THF (200 ml), 1 M solution of BH$_3$. THF in THF (15.56 g, 181 ml, 181 mmol) was added dropwise using a cannula under argon pressure. Initially, the rate of addition was controlled to maintain a moderate effervescence. Once the effervescence stopped, the rate of addition was increased. After the addition, the mixture was stirred at 0° C. for about 1.5 hr. The completion of the reaction was confirmed by TLC analysis. The reaction was then quenched by the careful addition of methanol at 0° C. The reaction mixture was concentrated in a rotavap. The oily residue was then co-evaporated with an additional quantity of methanol (500 ml). The resulted oily residue was purified by flash chromatography using Combi-flash instrument to afford 8 g (90%) of N-Boc-N-Me-aminoethanol ($^{13}$C$_3$, $^{15}$N) 151 as a colorless oil. MS (180, M+H).

Step 2 (FIG. 29a):

To a mixture of N-Boc-N-Me-aminoethanol ($^{13}$C$_3$, $^{15}$N) 151 (8 g, 44.6 mmol), Carbon tetrabromide (17.8 g, 53. 5 mmol) and sodium azide (8.7 g, 133.8 mmol), anhydrous DMF (240 ml) was added using a cannula under argon atmosphere and the resulted slurry was stirred for min. A solution of triphenylphosphine (14 g, 53.5 mmol) in anhydrous dimethylformamide (45 ml) was made in a separate flask and kept under argon. To the above slurry, the triphenylphosphine solution was added dropwise using a cannula under argon pressure. The flask was rinsed with additional DMF (5 ml) to ensure quantitative transfer. The reaction mixture got warmed up with the development of a bright yellow color. The mixture was then stirred for min at room temperature. An aliquot was taken out and a few drops of ether was added. The white solid was spun down and the supernatant was analyzed by TLC. The completion of the reaction was indicated by the disappearance of the starting alcohol (Rf: 0.24) with the formation of a less polar product (Rf: 0.65). Diethyl ether (1.5 L) was added to the reaction mixture to precipitate triphenylphosphonium oxide. The resulted slurry was then filtered through a sintered funnel with a celite pad. The white solid was thoroughly washed with additional quantity of ether (500 ml). The combined filtrate was then washed with brine (300 ml×4) and dried over Na$_2$SO$_4$, filtered and evaporated in a rotavapor at temperature below 25° C. under moderate vacuum. The residue was then purified by flash chromatography using the Combi-Fash instrument to afford the azide 152 as a colorless oil, which was immediately used for the next step without any analysis.

Step 3 (FIG. 29a):

The azide 152 resulted from the above step was dissolved in methanol (900 ml). Saturated ammonium chloride solution (180 ml) was then added and the reaction mixture was stirred at room temperature for 5 min. Zinc powder (8.7 g, 133.8 mmol) was then added to the reaction mixture in small portions. Evolution of nitrogen was observed. The reaction mixture was then stirred for 10 minutes at RT. An aliquot was analyzed by TLC and the completion of the reaction was confirmed by the disappearance of the starting material (Rf: 0.65). The solids (unreacted zinc and zinc hydroxide) were filtered off and washed with methanol (200 ml). The combined filtrates were concentrated in the rotavapor. The residue was dissolved in methylene chloride and extracted with 6N NaOH solution (800 mL). The aqueous layer was back-extracted with methylene chloride (800 ml). The combined methylene chloride extracts were dried over $Na_2SO_4$ and evaporated in a rotavapor to furnish the Boc-amine 153 as a faint yellow thick oil. The over-all yield from both steps 2 and 3 was 80% MS (179, M+H)

Step 4 (FIG. 29a):

To a solution of the N-Me-Boc-amine 153 (5.62 g, 31.5 mmol) in acetone (200 ml), a solution of Fmoc-Osu (10.64 g, 31.5 mmol) in acetone (200 ml) was added. After stirring the reaction mixture for 5 min. at RT, 80 mL of sat $NaHCO_3$ solution was added. The reaction mixture was continued stirring for 2 hr. A TLC at this point indicated the complete disappearance of the starting material with the formation of a less-polar product. Acetone was evaporated in a rotavapor. The semisolid residue was partitioned between EtOAc (2 L), 1 M HCl (125 ml), brine (125 mL) and water (250 mL). The EtOAc layer was further washed with 1 M HCl (100 mL), brine+water (150 mL+250 mL) and brine (250 mL×2). Dried over $Na_2SO_4$ and evaporated in a rotavapor to afford an off-white solid product (12.6 g), which was dissolved in methylene chloride (200 mL) and treated with 4N HCl (188 mL) for 30 min. to furnish the Fmoc amine hydrochloride salt 154 as a white solid (10.4 g). MS (301, M+H).

Example 20

Synthesis of Fmoc-NH—$CH_2CH_2$—N(Me)-CO—$CH_2CH_2$—COOH Comprising Eight Isotopically Encoded Sites (FIG. 29b):

To a suspension of the Fmoc-amine hydrochloride 154 (7.25 g, 21.5 mmol)) in methylene chloride (600 mL), succinic anhydride ($^{13}C_4$) was added in a single shot. $Et_3N$ (4.5 ml, 32.3 mmol) was then added dropwise. After stirring the reaction mixture for 30 min at RT, TLC analysis indicated the complete disappearance of the starting material. Methylene chloride was evaporated in a rotavap. The residue resulted was partitioned in EtOAc (2 L) and 1M HCl (350 mL). The organic layer was further washed with 1 M HCl (200 mL) and brine (200 mL×4), dried over $Na_2SO_4$ and evaporated to furnish a white foam, which on keeping under high vacuum for 48 hrs gave encoded Fmoc-NH—$CH_2CH_2$—N(Me)-CO—$CH_2CH_2$—COOH 155 as a white solid (7.5 g, 86%). MS (405, M+1)

Figure 25A:
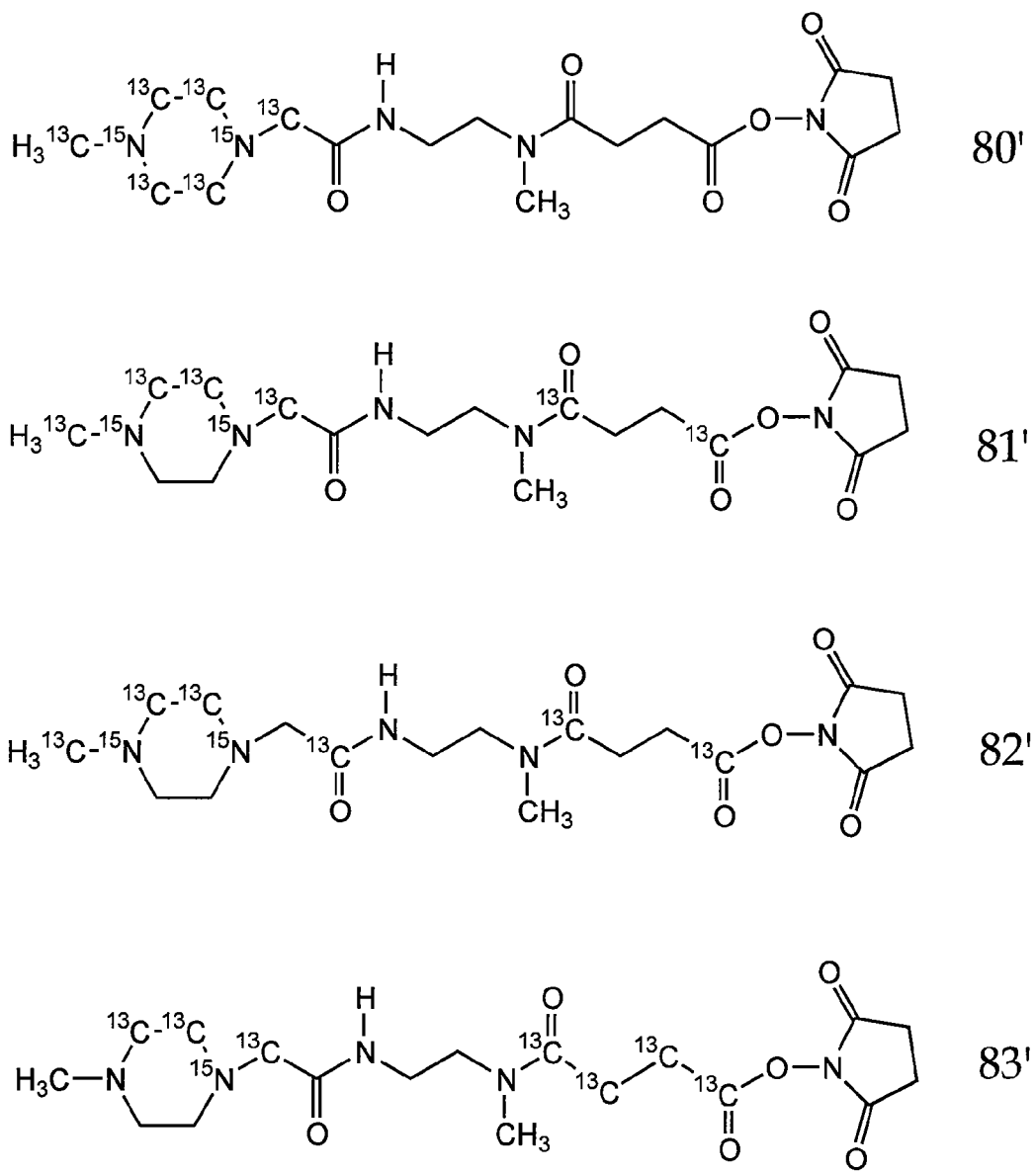
FIG. 25a is an illustration of various isobaric labeling reagents that, when considered with the compounds illustrated in FIG. 25b, can form an 8-plex set.
Figure 27C:
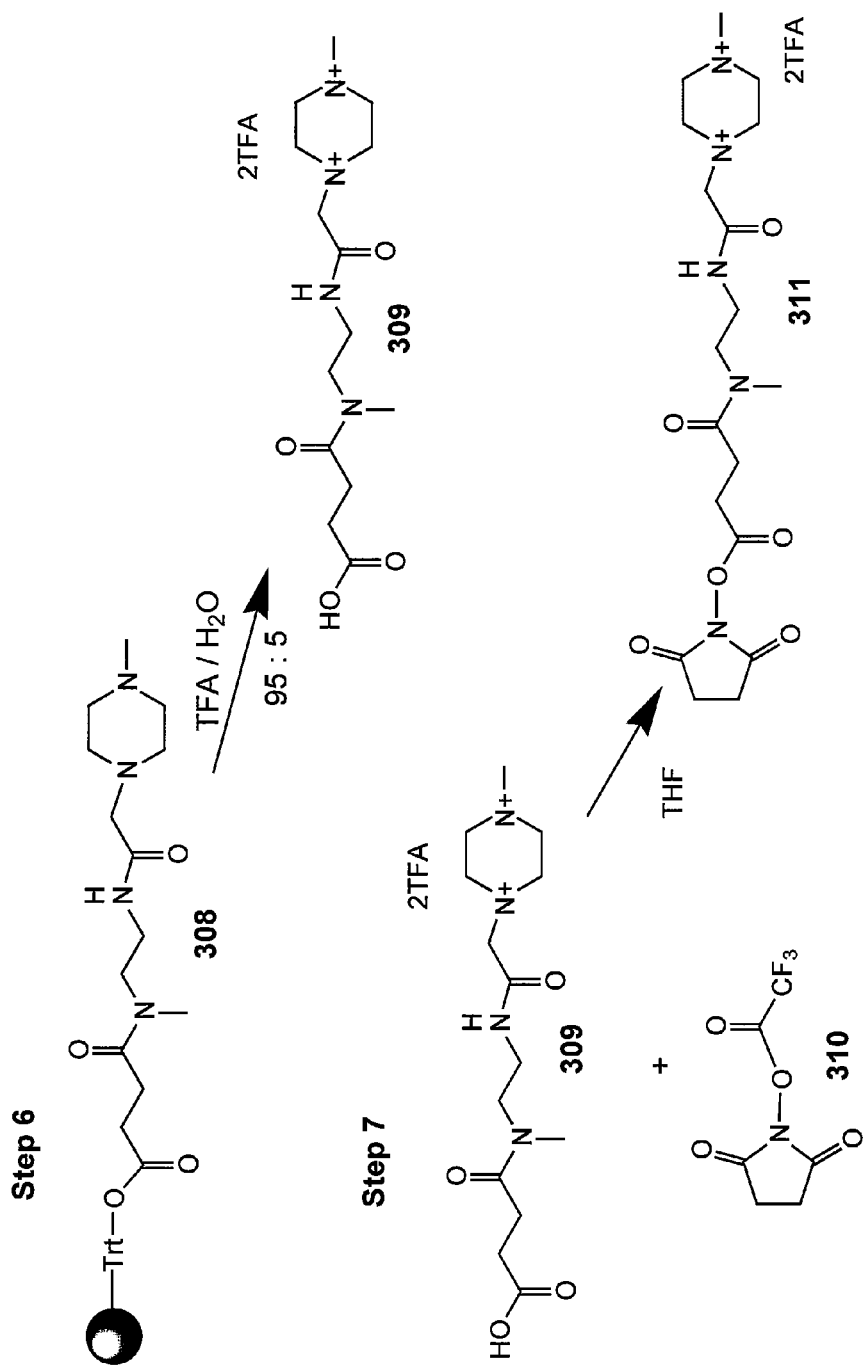
FIG. 27c is an illustration of Steps 6-7 of an exemplary synthesis of an exemplary labeling reagent.

The compositions prepared according to Examples 19 and 20 can be used in the synthesis of the encoded labeling reagents according to FIGS. 27a-27c using the synthetic protocol substantially as described in Examples 1-7, above (also see FIGS. 7a-7c). FIGS. 25a-25b illustrate some labeling reagents that can be prepared by the use of the general procedures disclosed herein. Furthermore, FIGS. 26a-26b illustrate some labeled analytes that can be prepared by use of the labeling reagents disclosed in FIGS. 25a-25c. Said labeled analytes will, upon fragmentation in a mass spectrometer, produce fragment ions and mixtures of fragment ions that can be used to quantify the analytes in various samples as discussed above.

It is also to be understood that through the choice of appropriate encoded starting materials, the procedures set forth above, in combination with no more than routing experimentation, can be used to prepare various other encoded compositions that can be used as labeling reagents according to the invention(s) disclosed herein. Thus, the examples set forth above are not intended to be limiting in any way.

While the present teachings are described in conjunction with various embodiments, it is not intended that the present teachings be limited to such embodiments. On the contrary, the present teachings encompass various alternatives, modifications and equivalents, as will be appreciated by those of skill in the art.

We claim:

1. A compound represented by formula I;

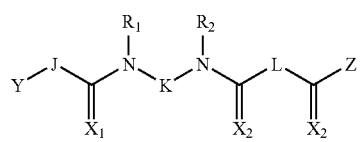

or a salt form thereof; wherein

Y is a piperazine moiety that may be substituted or unsubstituted and that may optionally be cleavably linked to a support, wherein the piperazine moiety comprises at least one ring nitrogen atom that is linked through a covalent bond to the group J;

J is a group represented by formula —$CJ'_2$-, wherein each J' is, independently of the other, hydrogen, deuterium, fluorine, chlorine, bromine, iodine, —$R_3$, —$OR_3$, —$SR_3$, —$R_3'OR_3$ or —$R_3'SR_3$;

K is a group represented by formula —$(CK'_2)_n$— or —$((CK'_2)_m$—$X_3(CK'_2)_m)_p$—, wherein n is an integer from 2 to 10, each m is, independently of the other, an integer from 1 to 5, p is 1 and each K' is, independently of the other, hydrogen, deuterium, fluorine, chlorine, bromine, iodine, —$R_4$, —$OR_4$, —$SR_4$, —$R_4'OR_4$ or —$R_4'SR_4$;

L is a group represented by formula —$(CL'_2)_q$- or —$((CL'_2)_m$-$X_3$—$(CL'_2)_m)_p$-, wherein q is an integer from 1 to 10, each m is, independently of the other, an integer from 1 to 5, p is 1 and each L' is, independently of the other, hydrogen, deuterium, fluorine, chlorine, bromine, iodine, —$R_5$, —$OR_5$, —$SR_5$, —$R_5'OR_5$ or —$R_5'SR_5$;

either

1) $R_1$ is hydrogen, deuterium or $R_6$ and $R_2$ is hydrogen, deuterium or $R_7$;

or

2) $R_1$ and $R_2$ taken together is a group represented by formula —$(CR'_2)_{q-or}$-$((CR'_2)_m$—$X_3$—$(CR'_2)_m)_p$ that forms a ring that bridges the two nitrogen atoms, wherein q is an integer from 1 to 10, each m is, independently of the other, an integer from 1 to 5, p is 1 and each R' is, independently of the other, hydrogen, deuterium, fluorine, chlorine, bromine, iodine, —$R_6$,—$OR_6$, —$SR_6$, —$R_6'OR_6$ or —$R_6'SR_6$;

$X_1$ is =O, =S, =NH or =NR$_7$;

each $X_2$ is, independently of the other, =O or =S;

each $X_3$ is, independently of the other, —O— or —S—; and

Z is —OH, —SH, —O$^{-V+}$, —S$^{-V+}$, wherein V$^+$ is a positively charged counterion;

each $R_3$, $R_4$, $R_5$, $R_6$ and/or $R_7$ is, independently of the other, alkyl, alkenyl, alkynyl, aryl, heteroaryl or arylalkyl; and each $R_3'$, $R_4'$, $R_5'$ and/or $R_6'$ is, independently of the other, alkylene, alkenylene, alkynylene, arylene or alkylarylene;

each X' is independently O or S; and each X" is independent of the other, —F, —Cl, —Br or I;

wherein the compound comprises at least one isotopically enriched site.

2. The compound of claim 1, wherein the group Y-J comprises at least one isotopically enriched site.

3. The compound of claim 1, wherein the group between J and Z comprises at least one isotopically enriched site.

4. The compound of claim 1, wherein the group represented by formula Y-J comprises at least one isotopically enriched site, and the group between J and Z comprises at least one isotopically enriched site.

5. The compound of claim 1, represented by formula III;

or a salt form thereof;

wherein s is an integer from 1 to 5 and t is an integer from 1 to 10;

$R_1$ is hydrogen, deuterium or $R_6$;

$R_2$ is hydrogen, deuterium or $R_7$;

$R_{11}$ is hydrogen, deuterium, methyl, —C(H)$_2$D, —C(H)D$_2$, —CD$_3$, other alkyl or —R'''; and each $R_9'$ is, independently of the other, alkylene, alkenylene, alkynylene, arylene or alkylarylene.

6. The compound of claim 5, wherein the compound is represented by formula:

-continued

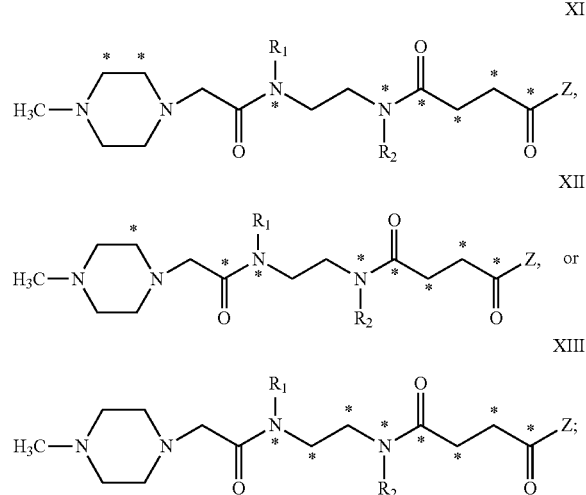

or a salt form thereof;
wherein
*indicates an isotopically enriched site comprising a $^{13}C$ substituted for $^{12}C$ and $^{15}N$ substituted for $^{14}N$, as appropriate;
$R_1$ is hydrogen or $R_6$; and
$R_2$ is hydrogen or $R_7$.

7. The compound of claim 5, wherein the compound is represented by formula:

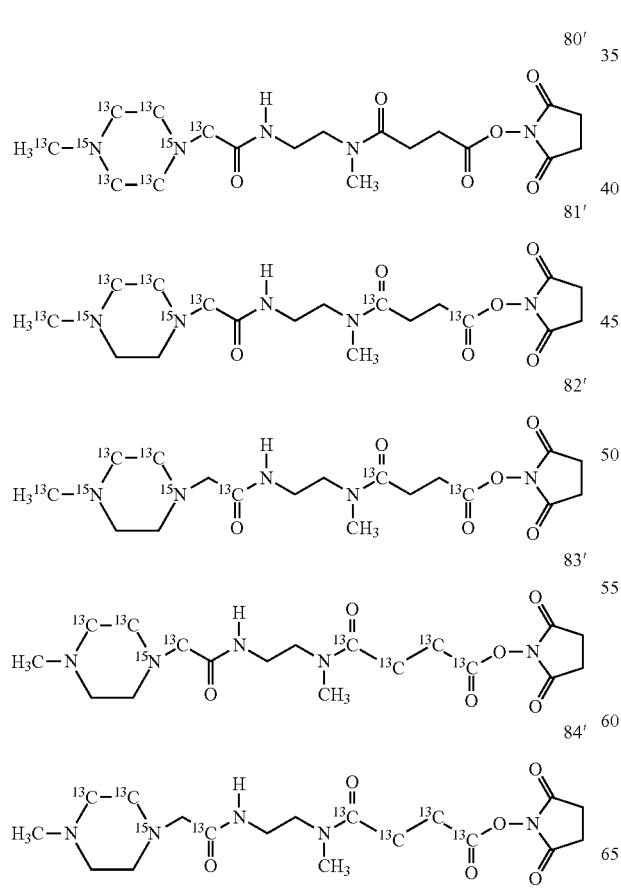

-continued

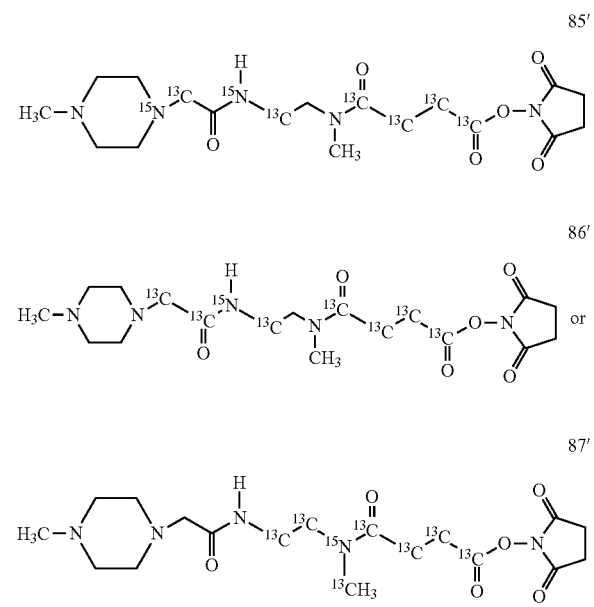

or a salt form thereof.

8. The compound of claim 1, represented by formula IV;

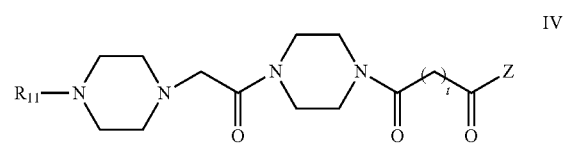

or a salt form thereof
wherein
t is an integer from 1 to 10;
$R_{11}$ is hydrogen, deuterium, methyl, —C(H)$_2$D, —C(H)D$_2$, —CD$_3$ or R'''
each $R_9$' is, independently of the other, alkylene, alkenylene, alkynylene, arylene or alkylarylene.

9. The compound of claim 8, wherein the compound is represented by formula:

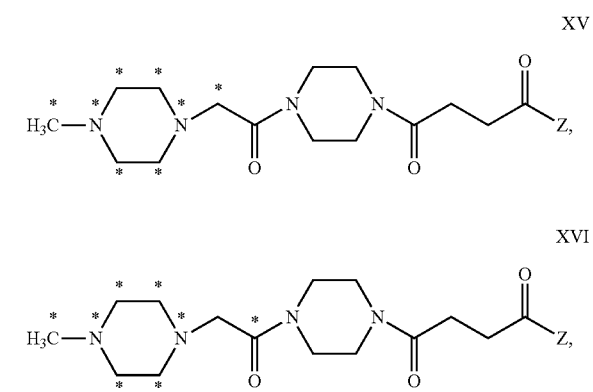

XVII

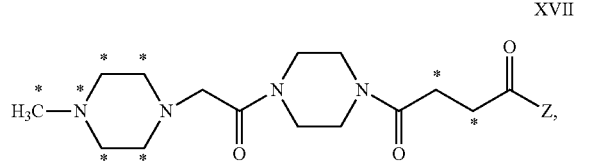

XVIII

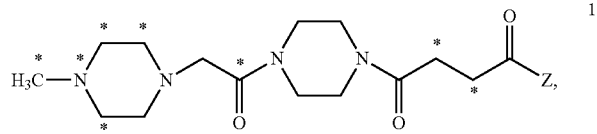

XIX

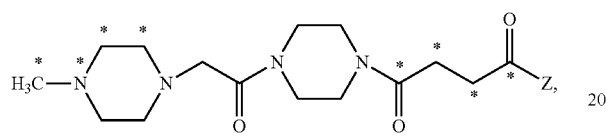

XX

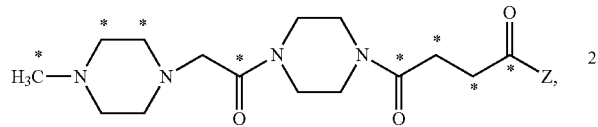

XXI

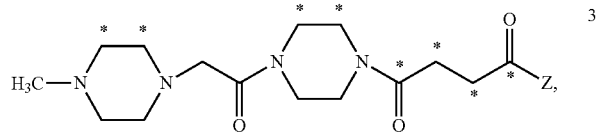

XXII

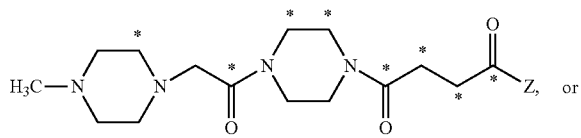

XXIII

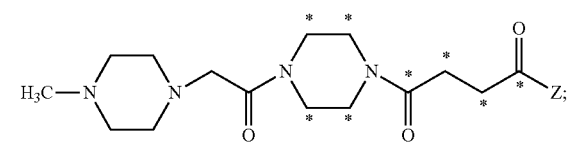

or a salt form thereof;

wherein

* indicates an isotopically enriched site comprising a $^{13}C$ substituted for $^{12}C$ and $^{15}N$ substituted for $^{14}N$, as appropriate.

10. The compound of claim 1, wherein the compound comprises two or more isotopically enriched sites.

11. The compound of claim 1, wherein Z is —OH.

12. The compound of claim 1, wherein Z is N-hydroxysuccinimide.

13. A kit comprising at least one compound according to claim 1.

14. The kit of claim 13, further comprising at least one additional reagent selected to perform an assay for quantifying one or more analytes in two or more different samples by differentially labeling the samples.

* * * * *